United States Patent
Mannick et al.

(10) Patent No.: US 10,596,165 B2
(45) Date of Patent: Mar. 24, 2020

(54) COMBINATION THERAPIES

(71) Applicant: resTORbio, Inc., Boston, MA (US)

(72) Inventors: Joan Mannick, Weston, MA (US); Chen Schor, Boston, MA (US); Grace Teo, Boston, MA (US)

(73) Assignee: RESTORBIO, INC., Boston, MA (US)

(*) Notice: Subject to any disclaimer, the term of this patent is extended or adjusted under 35 U.S.C. 154(b) by 0 days.

(21) Appl. No.: 16/273,919

(22) Filed: Feb. 12, 2019

(65) Prior Publication Data

US 2019/0247386 A1 Aug. 15, 2019

Related U.S. Application Data

(60) Provisional application No. 62/629,636, filed on Feb. 12, 2018, provisional application No. 62/765,006, filed on Aug. 17, 2018, provisional application No. 62/751,263, filed on Oct. 26, 2018.

(51) Int. Cl.
| | |
|---|---|
| *A61K 31/7048* | (2006.01) |
| *A61K 31/4745* | (2006.01) |
| *A61K 31/436* | (2006.01) |
| *A61K 31/5377* | (2006.01) |
| *A61P 1/16* | (2006.01) |
| *A61P 25/16* | (2006.01) |
| *A61K 31/5375* | (2006.01) |
| *A61K 31/435* | (2006.01) |

(52) U.S. Cl.
CPC ........ *A61K 31/4745* (2013.01); *A61K 31/436* (2013.01); *A61K 31/5377* (2013.01); *A61P 1/16* (2018.01); *A61P 25/16* (2018.01)

(58) Field of Classification Search
CPC ............ A61K 31/7048; A61K 31/5375; A61K 31/435
USPC ...................................... 514/31, 231.5, 293
See application file for complete search history.

(56) References Cited

U.S. PATENT DOCUMENTS

| | | | |
|---|---|---|---|
| 3,929,992 A | 12/1975 | Sehgal et al. | |
| 5,665,772 A | 9/1997 | Cottens et al. | |
| 5,741,677 A | 4/1998 | Kozlowski et al. | |
| 6,015,815 A | 1/2000 | Mollison | |
| 6,440,458 B1 | 8/2002 | Yamashita et al. | |
| 7,091,213 B2 | 8/2006 | Metcalf, III et al. | |
| 7,667,039 B2 | 2/2010 | Garcia-Echeverria et al. | |
| 7,994,170 B2 | 8/2011 | Garcia-Echeverria et al. | |
| 8,431,592 B2 | 4/2013 | Garcia-Echeverria et al. | |
| 8,436,177 B2 | 5/2013 | Stowasser et al. | |
| RE44,768 E | 2/2014 | Skotnicki et al. | |
| 9,358,229 B2 | 6/2016 | Vannucchi et al. | |
| 9,358,236 B2 | 6/2016 | Murphy et al. | |
| 9,370,508 B2 | 6/2016 | Garcia-Echeverria et al. | |
| 10,004,803 B2 | 6/2018 | Mannick et al. | |
| 10,286,069 B2 | 5/2019 | Mannick et al. | |
| 10,441,584 B2 | 10/2019 | Mannick et al. | |
| 2004/0228917 A1 | 11/2004 | Oshlack et al. | |
| 2005/0101624 A1 | 5/2005 | Betts et al. | |
| 2006/0264453 A1 | 11/2006 | Mudumba et al. | |
| 2007/0036857 A1 | 2/2007 | Becker | |
| 2007/0265294 A1 | 11/2007 | Kleinman | |
| 2008/0206322 A1 | 8/2008 | Becker | |
| 2009/0082387 A1 | 3/2009 | Czarnik | |
| 2009/0088373 A1 | 4/2009 | Gallo et al. | |
| 2009/0270515 A1 | 10/2009 | Gruber | |
| 2010/0087474 A1 | 4/2010 | Kaushal et al. | |
| 2010/0129357 A1 | 5/2010 | Garcia-Martinez | |
| 2010/0150829 A1 | 6/2010 | Garcia-Martinez | |
| 2010/0152147 A1 | 6/2010 | Fugue et al. | |
| 2010/0196311 A1 | 8/2010 | Kim et al. | |
| 2010/0196365 A1 | 8/2010 | Garcia-Echeverria et al. | |
| 2010/0233733 A1 | 9/2010 | Fantl | |
| 2010/0260858 A1 | 10/2010 | Ruddy | |
| 2010/0305093 A1 | 12/2010 | Anand et al. | |
| 2011/0020338 A1 | 1/2011 | Garcia-Echeverria et al. | |
| 2011/0129496 A1 | 6/2011 | Ahmed et al. | |
| 2011/0230476 A1 | 9/2011 | Niu et al. | |
| 2012/0148552 A1 | 6/2012 | Jensen | |
| 2012/0207751 A1 | 8/2012 | Garcia-Echeverria et al. | |
| 2012/0282252 A1 | 11/2012 | Garcia-Echeverria et al. | |
| 2013/0178479 A1 | 7/2013 | Chen et al. | |
| 2013/0245061 A1 | 9/2013 | Cao et al. | |
| 2013/0289064 A1 | 10/2013 | Stowasser et al. | |
| 2013/0296316 A1 | 11/2013 | Pollastri et al. | |
| 2013/0309258 A1 | 11/2013 | June | |
| 2013/0331388 A1 | 12/2013 | Murphy et al. | |
| 2014/0038920 A1 | 2/2014 | Ballabio et al. | |
| 2014/0206678 A1 | 7/2014 | Shenk et al. | |
| 2014/0242162 A1 | 8/2014 | Diederich et al. | |
| 2014/0243396 A1 | 8/2014 | Griffin et al. | |

(Continued)

FOREIGN PATENT DOCUMENTS

| | | |
|---|---|---|
| CN | 1195289 A | 10/1998 |
| CN | 101862297 A | 10/2010 |

(Continued)

OTHER PUBLICATIONS

AlDakheel et al., "Pathogenesis-targeted, disease-modifying therapies in Parkinson disease," Neurotherapeutics, vol. 11, No. 1, Jan. 2014 (pp. 6-23).
Alvero et al., "Targeting the mitochondria activates two independent cell death pathways in ovarian cancer stem cells," Molecular Cancer Therapeutics, vol. 10, No. 8, Aug. 2011 (pp. 1385-1393).
Apsel et al., "Targeted polypharmacology: discovery of dual inhibitors of tyrosine and phosphoinositide kinases," Nature Chemical Biology, vol. 4, No. 11, Nov. 2008 (pp. 691-699).
Berge et al., "Pharmaceutical Salts," Journal of Pharmaceutical Sciences, vol. 66, No. 1, Jan. 1977 (1-19).
Bibb et al., "Severe deficiencies in dopamine signaling in presymptomatic Huntington's disease mice," Proceedings of the National Academy of Sciences of the United States of America, vol. 97, No. 12, Jun. 2000 (pp. 6809-6814).

(Continued)

*Primary Examiner* — Raymond J Henley, III
(74) *Attorney, Agent, or Firm* — Andrea L. C. Reid; Dechert LLP

(57) ABSTRACT

The present invention provides methods and pharmaceutical compositions for the treatment or prevention of autophagy-related diseases, disorders, or conditions.

16 Claims, 16 Drawing Sheets

(56) References Cited

U.S. PATENT DOCUMENTS

| | | |
|---|---|---|
| 2015/0000744 A1 | 1/2015 | Park et al. |
| 2015/0051266 A1 | 2/2015 | Kochenderter |
| 2015/0079155 A1 | 3/2015 | Jensen |
| 2015/0140036 A1 | 5/2015 | Mannick et al. |
| 2015/0157645 A1 | 6/2015 | Hirawat et al. |
| 2016/0045441 A1 | 2/2016 | Diederich et al. |

FOREIGN PATENT DOCUMENTS

| | | |
|---|---|---|
| CN | 101969931 A | 2/2011 |
| CN | 102138903 A | 8/2011 |
| CN | 102199152 | 9/2011 |
| CN | 102292078 A | 12/2011 |
| DE | 2347682 | 4/1974 |
| EP | 0868911 | 10/1998 |
| JP | H-11509223 | 8/1999 |
| JP | 2003530340 | 10/2003 |
| JP | 2004035547 | 2/2004 |
| JP | 2004354394 A | 12/2004 |
| JP | 2006188539 A | 7/2006 |
| JP | 2009102341 | 5/2009 |
| TW | 550091 B | 9/2003 |
| WO | WO-1994/009010 | 4/1994 |
| WO | WO 1994/009010 | 4/1994 |
| WO | WO-1995/014023 | 5/1995 |
| WO | WO 1995/014023 | 5/1995 |
| WO | WO-1995/016691 | 6/1995 |
| WO | WO 1995/016691 | 6/1995 |
| WO | WO-1996/041807 | 12/1996 |
| WO | WO 1996/041807 | 12/1996 |
| WO | WO-1998/002441 | 1/1998 |
| WO | WO 1998/002441 | 1/1998 |
| WO | WO 1999/015530 | 4/1999 |
| WO | WO-1999/015530 | 4/1999 |
| WO | WO 2001/014387 | 3/2001 |
| WO | WO-2001/014387 | 3/2001 |
| WO | WO 2004/089925 | 10/2004 |
| WO | WO-2004/089925 | 10/2004 |
| WO | WO-2005/034916 A1 | 4/2005 |
| WO | WO-2006/094507 | 9/2006 |
| WO | WO 2006/122806 | 11/2006 |
| WO | WO-2006/122806 | 11/2006 |
| WO | WO 2007/044813 | 4/2007 |
| WO | WO-2007/044813 | 4/2007 |
| WO | WO 2007/061737 | 5/2007 |
| WO | WO-2007/061737 | 5/2007 |
| WO | WO 2007/133249 | 11/2007 |
| WO | WO-2007/133249 | 11/2007 |
| WO | WO 2007/136940 | 11/2007 |
| WO | WO-2007/136940 | 11/2007 |
| WO | WO-2008/014446 | 1/2008 |
| WO | WO 2008/014446 | 1/2008 |
| WO | WO-2008/016633 A2 | 2/2008 |
| WO | WO-2008/032162 | 3/2008 |
| WO | WO 2008/032162 | 3/2008 |
| WO | WO-2008/064093 | 5/2008 |
| WO | WO-2008/070740 | 6/2008 |
| WO | WO 2008/070740 | 6/2008 |
| WO | WO-2008/103636 A1 | 8/2008 |
| WO | WO-2009/013305 A1 | 1/2009 |
| WO | WO-2009/118324 A1 | 10/2009 |
| WO | WO-2009/143313 | 11/2009 |
| WO | WO 2009/143313 | 11/2009 |
| WO | WO-2009/153597 | 12/2009 |
| WO | WO 2009/153597 | 12/2009 |
| WO | WO-2010/056754 A2 | 5/2010 |
| WO | WO-2010/049481 A1 | 6/2010 |
| WO | WO 2010/062571 | 6/2010 |
| WO | WO-2010/062571 | 6/2010 |
| WO | WO 2010/106211 | 9/2010 |
| WO | WO-2010/106211 | 9/2010 |
| WO | WO 2010/110685 | 9/2010 |
| WO | WO-2010/110685 | 9/2010 |
| WO | WO 2010/114484 | 10/2010 |
| WO | WO-2010/114484 | 10/2010 |
| WO | WO-2010/118419 A2 | 10/2010 |
| WO | WO-2010/129622 A1 | 11/2010 |
| WO | WO-2011/031896 A2 | 3/2011 |
| WO | WO-2012/006619 A2 | 1/2012 |
| WO | WO-2012/007926 | 1/2012 |
| WO | WO 2012/007926 | 1/2012 |
| WO | WO-2012/047775 A1 | 4/2012 |
| WO | WO-2012/075253 A2 | 6/2012 |
| WO | WO 2012/097039 | 7/2012 |
| WO | WO 2015/051043 | 4/2015 |
| WO | WO 2017/139616 | 8/2017 |

OTHER PUBLICATIONS

Burbulla et al., "Dopamine oxidation mediates mitochondrial and lysosomal dysfunction in Parkinson's disease," Science, vol. 357, No. 6357, Sep. 2017 (pp. 1255-1261).
Chang et al., "Novel Phosphoinositide 3-Kinase/mTOR Dual Inhibitor, NVP-BGT226, Displays Potent Growth-Inhibitory Activity against Human Head and Neck Cancer Cells in Vitro and in Vivo," Clinical Cancer Research, vol. 17, No. 22, Nov. 2011 (pp. 7116-7126).
Chen et al., "A53T Human α-Synuclein Overexpression in Transgenic Mice Induces Pervasive Mitochondria Macroautophagy Defects Preceding Dopamine Neuron Degeneration," The Journal of Neuroscience, vol. 35, No. 3, Jan. 2015 (pp. 890-905).
Chen et al., "Age-dependent Motor Deficits and Dopaminergic Dysfunction in DJ-1 Null Mice," Journal of Biological Chemistry, vol. 280, No. 22, Mar. 2005 (pp. 21418-21426).
Cheng et al., "Self-renewing endodermal progenitor lines generated from human pluripotent stem cells," Cell Press: Cell Stem Cell, vol. 10, No. 4, Apr. 2012 (pp. 371-384).
Chresta et al., "AZD8055 Is a Potent, Selective, and Orally Bioavailable ATP-Competitive Mammalian Target of Rapamycin Kinase Inhibitor with in vitro and in vivo Antitumor Activity," Cancer Research, vol. 70, No. 1, Jan. 2010 (pp. 288-298).
Connolly and Lang, "Pharmacological treatment of Parkinson disease: a review," JAMA, vol. 311, No. 16, Apr. 2014 (pp. 1670-1683).
Cooper et al., "Pharmacological rescue of mitochondrial deficits in iPSC-derived neural cells from patients with familial Parkinson's disease," Science Translational Medicine, vol. 4, No. 141, Jul. 2012 (pp. 1-25).
Davies et al., "Formation of Neuronal Intranuclear Inclusions Underlies the Neurological Dysfunction in Mice Transgenic for the HD Mutation," Cell, vol. 90, No. 3, Aug. 1997 (pp. 537-548).
de Serres, "Alpha-1 Antitrypsin Deficiency Is Not a Rare Disease but a Disease That Is Rarely Diagnosed," Environmental Health Perspectives, vol. 111, No. 16, Dec. 2003 (pp. 1851-1854).
de Serres, "Worldwide racial and ethnic distribution of alphal-antitrypsin deficiency: summary of an analysis of published genetic epidemiologic surveys," Chest, vol. 122, No. 5, Nov. 2002 (pp. 1818-1829).
DeMeo and Silverman, "Alpha1-antitrypsin deficiency. 2: genetic aspects of alpha(1)-antitrypsin deficiency: phenotypes and genetic modifiers of emphysema risk," Thorax, vol. 59, No. 3, Mar. 2004 (pp. 259-264).
Domingues et al., "Lumbar puncture in patients using anticoagulants and antiplatelet agents," Arquivos de Neuro-Psiquiatria, vol. 74, No. 8, Aug. 2016 (pp. 679-686).
Dryanovski et al., "Calcium entry and α-synuclein inclusions elevate dendritic mitochondrial oxidant stress in dopaminergic neurons," Journal of Neuroscience, vol. 33, No. 24, Jun. 2013 (pp. 10154-10164).
Duda et al., "Novel antibodies to synuclein show abundant striatal pathology in Lewy body diseases," Annals of Neurology, vol. 52, No. 2, Aug. 2002 (pp. 205-210).
Fagerhol and Laurell, "The polymorphism of "prealbumins" and alpha-1-antitrypsin in human sera," Clinica Chimica Acta, vol. 16, No. 2, May 1967 (pp. 199-203).
Fregonese and Stolk, "Hereditary alpha-1-antitrypsin deficiency and its clinical consequences," Orphanet Journal of Rare Diseases, vol. 3, No. 16, Jun. 2008 (9 pages).

(56) References Cited

OTHER PUBLICATIONS

Galimberti et al, "EphA4 Signaling in Juveniles Establishes Topographic Specificity of Structural Plasticity in the Hippocampus," Neuron, vol. 65, No. 5, Mar. 2010 (pp. 627-642).

Galimberti et al., "Long-term rearrangements of hippocampal mossy fiber terminal connectivity in the adult regulated by experience," Neuron, vol. 50, No. 5, Jun. 2006 (pp. 749-763).

Garcia-Martinez et al., "Ku-0063794 is a specific inhibitor of the mammalian target of rapamycin (mTOR)," Biochemical Journal, vol. 421, No. 1, Jun. 2009 (pp. 29-42).

Gogolla et al., "Preparation of organotypic hippocampal slice cultures for long-term live imaging," Nature Protocols, vol. 1, No. 3, Sep. 2006 (pp. 1165-1171).

Gross et al., "Abstract 4484: AR-mTOR-26—A potent, selective mTORC 1/2 kinase inhibitor for the treatment of malignancy," 101st Animal Meeting of the American Association of Cancer Research (AACR), Apr. 17-21, 2010, Washington, D.C. (2 pages).

Gupta et al., "Identification of Selective Inhibitors of Cancer Stem Cells by High-Throughput Screening," Cell, vol. 138, No. 4, Aug. 2009 (pp. 645-659).

Guzman et al., "Oxidant stress evoked by pacemaking in dopaminergic neurons is attenuated by DJ-1," Nature, vol. 468, No. 7324, Dec. 2010 (pp. 696-700).

Indge and Childs, "A new method for deriving steady-state rate equations suitable for manual or computer use," Biochemical Journal, vol. 155, No. 3, Jun. 1976 (pp. 567-570).

International Search Report and Written Opinion issued by the United States Patent and Trademark Office as International Searching Authority for International Application No. PCT/US2019/017688, dated Apr. 25, 2019 (9 pages).

Kashiyama et al., "Antitumor Activity and Induction of TP53-Dependent Apoptosis toward Ovarian Clear Cell Adenocarcinoma by the Dual PI3K/mTOR Inhibitor DS-7423," PLoS One, vol. 9, No. 2, Feb. 2014 (12 pages).

Kaushik and Cuervo, "Methods to monitor chaperone-mediated autophagy," Methods in Enzymology, vol. 452, No Month Listed 2009 (pp. 297-324).

Kovalevich and Langford, "Considerations for the use of SH-SY5Y neuroblastoma cells in neurobiology," Methods in Molecular Biology, vol. 1078, Nov. 2013 (pp. 9-21).

Kriks et al., "Dopamine neurons derived from human ES cells efficiently engraft in animal models of Parkinson's disease," Nature, vol. 480, No. 7378, Nov. 2011 (pp. 547-551).

Lee et al., "Abstract C270: In vitro and in vivo antitumor activity of DCBCI0901, a potent PI3K/mTORC1/mTORC2 inhibitor," Molecular Cancer Therapeutics, vol. 12, No. 11 (Supp), Nov. 2013 (2 pages).

Lee et al., "Efficient generation of midbrain and hindbrain neurons from mouse embryonic stem cells," Nature Biotechnology, vol. 18, No. 6, Jun. 2000 (pp. 675-679).

Lee et al., "Improved intracellular delivery of glucocerebrosidase mediated by the HIV-1 TAT protein transduction domain," Biochemical and Biophysical Research Communications, vol. 337, No. 2, Nov. 2005 (pp. 701-707).

Lin et al., "Leucine-Rich Repeat Kinase 2 Regulates the Progression of Neuropathology Induced by Parkinson's-Disease-Related Mutant a-synuclein," Neuron, vol. 64, No. 6, Dec. 2009 (pp. 807-827).

Luisetti and Seersholm, "Alpha1-antitrypsin deficiency, 1: epidemiology of alpha 1-antitrypsin deficiency," Thorax, vol. 59, No. 2, No Month Listed 2004 (pp. 164-169).

Luthi-Carter et al., "Decreased expression of striatal signaling genes in a mouse model of Huntington's disease," Human Molecular Genetics, vol. 9, No. 9, May 2000 (pp. 1259-1271).

Lynch-Day et al., "The role of autophagy in Parkinson's disease," Cold Spring Harbor Perspectives in Medicine, vol. 2, No. 4, Apr. 2012 (pp. 1-13).

Mazzulli et al., "Gaucher disease glucocerebrosidase and α-synuclein form a bidirectional pathogenic loop in synucleinopathies," Cell, vol. 146, No. 1, Jul. 2011 (pp. 37-52).

Miller, "mTORC1/mTORC2 selective inhibitors: Identification and characterization of novel small molecules with anti-tumor activity," European Journal of Cancer Supplements, vol. 6, No. 12, Abstract 322, Poster, Oct. 2008 (pp. 102-103).

Navarro et al., "Targeting Tumor Mitochondrial Metabolism Overcomes Resistance to Antiangiogenics," Cell Reports, vol. 15, No. 12, Jun. 2016 (pp. 2705-2718).

Nussbaum and Ellis, "Alzheimer's disease and Parkinson's disease," New England Journal of Medicine, vol. 348, No. 14, Apr. 2003 (pp. 1356-1364).

Olanow and Tatton, "Etiology and pathogenesis of Parkinson's disease," Annual Review of Neuroscience, vol. 22, Mar. 1999 (pp. 123-144).

Riva and Kohane, "SNPper: retrieval and analysis of human SNPs," Bioinformatics, vol. 18, No. 12, Dec. 2002 (pp. 1681-1685).

Schildknecht et al., "The human dopaminergic neuronal cell line LUHMES as in vitro model for Parkinson's disease," Journal of Neurochemistry, vol. 110, supp. 1, Jul. 2009 (1 page).

Sidransky and Lopez, "The link between the GBA gene and parkinsonism," The Lancet Neurology, vol. 11, No. 11, Nov. 2012 (pp. 986-998).

Sidransky et al., "Multicenter analysis of glucocerebrosidase mutations in Parkinson's disease," New England Journal of Medicine, vol. 361, No. 17, Oct. 2009 (pp. 1651-1661).

Somers et al., "Generation of transgene-free lung disease-specific human induced pluripotent stem cells using a single excisable lentiviral stem cell cassette," Stem Cells, vol. 28, No. 10, Oct. 2010 (pp. 1728-1740).

Spillantini et al., "Alpha-synuclein in Lewy bodies," Nature, vol. 388, No. 6645, Aug. 1997 (pp. 839-840).

Stoppini et al., "A simple method for organotypic cultures of nervous tissue," Journal of Neuroscience Methods, vol. 37, No. 2, Apr. 1991 (pp. 173-182).

Takahashi et al., "Induction of pluripotent stem cells from adult human fibroblasts by defined factors," Cell, vol. 131, No. 5, Nov. 2007 (pp. 861-872).

The Huntington's Disease Collaborative Research Group, "A novel gene containing a trinucleotide repeat that is expanded and unstable on Huntington's disease chromosomes," Cell, vol. 72, No. 6, Mar. 1993 (pp. 971-983).

Travis and Salvesen, "Human plasma proteinase inhibitors," Annual Review of Biochemistry, vol. 52, No Month Listed 1983 (pp. 655-709).

Trocoli and Djavaheri-Mergny, "The complex interplay between autophagy and NF-κB signaling pathways in cancer cells," American Journal of Cancer Research, vol. 1, No. 5, Apr. 2011 (pp. 629-649).

Wallace et al., "Abstract B267: AR-mTOR-1: A potent, selective mTORC 1/2 kinase inhibitor for the treatment of malignancy," AACR, International Conference: Molecular Targets and Cancer Therapeutics, Nov. 15-19, 2009, Boston, Massachusetts (2 pages).

Wilson et al., "Emergence of a stage-dependent human liver disease signature with directed differentiation of alpha-1 antitrypsin-deficient iPS cells," Stem Cell Report, vol. 4, No. 5, May 2015 (pp. 873-885).

Wilson et al., "Sustained expression of alpha1-antitrypsin after transplantation of manipulated hematopoietic stem cells," American Journal of Respiratory Cell and Molecular Biology, vol. 39, No. 2, Aug. 2008 (pp. 133-141).

Woodward et al., "iPSC-derived dopamine neurons reveal differences between monozygotic twins discordant for Parkinson's disease," Cell Reports, vol. 9, No. 4, Nov. 2014 (pp. 1173-1182).

Yu et al., "Biochemical, Cellular, and in vivo Activity of Novel ATP-Competitive and Selective Inhibitors of the Mammalian Target of Rapamycin," Cancer Research, vol. 69, No. 15, Aug. 2009 (pp. 6232-6240).

Araki et al., "The role of mTOR in memirt if CD8+ T-cell differentation," Immunological Reviews, vol. 235, No. 1, May 2010 (pp. 234-243).

Ballou et al., "Rapamycin and mTOR kinase inhibitors," Journal of Chemical Biology, vol. 1, No. 1-4, Nov. 2008 (pp. 27-36).

(56) References Cited

OTHER PUBLICATIONS

Berg et al., "The role of CD8 T cells in innate immunity and in antigen non-specific protection," Current Opinion in Immunology, vol. 18, No. 3, Jun. 2006 (pp. 338-343).
Bitto et al., "Transient rapamycin treatment can increase lifespan and healthspan in middle-aged mice," Elife, Aug. 2016 (17 pages).
Boraschi et al., "The Gracefully Aging Immune System," Science Translational Medicine, vol. 5, No. 185, May 2013 (10 pages).
Cai et al., "Rapamycin, Autophagy, and Alzheimer's Disease," Journal of Biochemical and Pharmacological Research, vol. 1, No. 2, Jun. 2013 (pp. 84-90).
Chen et al., "mTOR regulation and therapeutic rejuvenation of aging hematopoietic stem cells," Science Signaling, vol. 2, No. 98, Nov. 2009 (16 pages).
Chi, "Regulation and function of mTOR signalling in T cell fate decisions," Nature Reviews Immunology, vol. 12, No. 5, Apr. 2012 (pp. 325-338).
Clegg et al., "Frailty in elderly people," Lancet, vol. 381, No. 9868, Mar. 2013 (pp. 752-762).
Dello Russo et al., "Involvement of mTOR kinase in cytokine-dependent microglial activation and cell proliferation," Biochemical Pharmacology, vol. 78, No. 9, Nov. 2009 (pp. 1242-1251).
Dominick et al., "Regulation of mTOR activity in Snell dwarf and GH receptor gene-disrupted mice," Endocrinology, vol. 156, No. 2, Feb. 2015 (pp. 565-575).
Ewald et al., "Dauer-independent insulin/IGF-1-signalling implicates collagen remodelling in longevity," Nature, vol. 519, No. 7541, Mar. 2015 (pp. 97-101).
Feldman et al., "Active-site inhibitors of mTOR target rapamycin-resistant outputs of mTORC1 and mTORC2," PLoS Biology, vol. 7, No. 2, Feb. 2009 (13 pages).
Flynn et al., "Late-life rapamycin treatment reverses age-related heart dysfunction," Aging Cell, vol. 12, No. 5, Oct. 2013 (pp. 851-862).
Golden-Mason et al., "Upregulation of PD-1 Expression on Circulating and Intrahepatic Hepatitis C Virus-Specific CD8+ T Cells Associated with Reversible Immune Dysfunction," Journal of Virology, vol. 81, No. 17, Sep. 2007 (pp. 9249-9258).
Harari et al., "A robust type I interferon gene signature from blood RNA defines quantitative but not qualitative differences between three major IFNβ drugs in the treatment of multiple sclerosis," Human Molecular Genetics, vol. 24, No. 11, Jun. 2015 (pp. 3192-3205).
Harrison et al., "Rapamycin fed late in life extends lifespan in genetically heterogeneous mice," Nature, vol. 406, No. 7253, Jul. 2009 (pp. 392-395).
Huye et al., "Combining mTor inhibitors with rapamycin-resistant T cells: a two-pronged approach to tumor elimination," Molecular Therapy, vol. 19, No. 12, Dec. 2011 (pp. 2239-2248).
International Search Report and Written Opinion issued by the European Patent Office as International Searching Authority for International Application No. PCT/EP2012/069541, dated Dec. 10, 2012 (9 pages).
International Search Report and Written Opinion issued by the European Patent Office as International Searching Authority for International Application No. PCT/IB2012/050669, dated Jun. 13, 2012 (14 pages).
International Search Report and Written Opinion issued by the European Patent Office as International Searching Authority for International Application No. PCT/IB2014/059965, dated Jun. 23, 2014 (8 pages).
International Search Report and Written Opinion issued by the European Patent Office as International Searching Authority for International Application No. PCT/IB2016/052980, dated Sep. 16, 2016 (14 pages).
International Search Report and Written Opinion issued by the European Patent Office as International Searching Authority for International Application No. PCT/IB2017/001579, dated Nov. 22, 2017 (10 pages).
International Search Report and Written Opinion issued by the European Patent Office as International Searching Authority for International Application No. PCT/US2014/065408, dated May 6, 2015 (15 pages).
Iob et al., "Evidence of increased clinical protection of an MF59-adjuvant influenza vaccine compared to a non-adjuvant vaccine among elderly residents of long-term care facilities in Italy," Epidemiology & Infection, vol. 133, No. 4, Aug. 2005 (pp. 687-693).
Keating et al., "The kinase mTOR modulates the antibody response to provide cross-protective immunity to lethal infection with influenza virus," Nature Immunology, vol. 14, No. 12, Dec. 2013 (pp. 1266-1276).
Kumar et al., "Age-related decline in immunity: implications for vaccine responsiveness," Expert Review of Vaccines, vol. 7, No. 4, May 2008 (pp. 467-479).
Lamming et al., "Depletion of Rictor, an essential protein component of mTORC2, decreases male lifespan," Aging Cell, vol. 13, No. 5, Oct. 2014 (pp. 911-917).
Lamming et al., "Rapamycin-induced insulin resistance is mediated by mTORC2 loss and uncoupled from longevity," Science, vol. 335, No. 6076, Mar. 2012 (pp. 1638-1643).
Laplante et al., "mTOR signaling in growth control and disease," Cell, vol. 149, No. 2, Apr. 2012 (pp. 274-293).
Lichterfeld et al., "Telomerase activity of HIV-1-specific CD8+ T cells: constitutive up-regulation in controllers and selective increase by blockade of PD ligand 1 in progressors," Blood, vol. 112, No. 9, Nov. 2008 (pp. 3679-3687).
Lievesley, Ed., "Ageism and age discrimination in secondary health care in the United Kingdom: A review of the literature," Department of Health, Centre for Policy on Ageing. Dec. 2009.
Mannick et al., "mTOR inhibition improves immune function in the elderly," Science Translational Medicine, vol. 6, No. 268, Dec. 2014 (8 pages).
McMichael et al., "Influenza vaccines: mTOR inhibition surprisingly leads to protection," Nature Immunology, vol. 14, No. 12, Dec. 2013 (pp. 1205-1207).
McNab, et al., "Type I interferons in infectious disease," Nature Review Immunology, vol. 15, No. 2, Feb. 2015 (pp. 87-103).
Murray et al., "Inhibition of influenza A virus replication by antagonism of a PI3K-AKT-mTOR pathway member identified by gene-trap insertional mutagenesis," Antiviral Chemistry and Chemotherapy, vol. 22, No. 5, May 2012 (pp. 205-215).
Nunes et al., "Expansion of a CD8+PD-1+ Replicative Senescence Phenotype in Early Stage CLL Patients is Associated with Inverted CD4:CD8 Ratios and Disease Progression," Clinical Cancer Research, vol. 18, No. 3, Feb. 2012 (pp. 678-687).
Nyfeler et al., "RAD001 enhances the potency of BEZ235 to inhibit mTOR signaling and tumor growth," PLoS One, vol. 7, No. 11, Nov. 2012 (9 pages).
Nyfeler et al., "Relieving autophagy and 4EBP1 from rapamycin resistance," Molecular and Cellular Biology, vol. 31, No. 14, Jul. 2011 (pp. 2867-2876).
Passacantilli et al., "Combined Therapy with RAD001 e BEZ235 overcomes resistance of PET immortalized cell lines to mTOR inhibition," Oncotarget, vol. 5, No. 14, Jul. 2014 (pp. 5381-5391).
Pollizzi et al., "Equivalent benefit of mTORCI blockade and combined PI3K-mTOR blockade in a mouse-model of tuberous sclerosis," Molecular Cancer, vol. 8, No. 38, Jun. 2009 (9 pages).
Sarkar et al., "A rational mechanism for combination treatment of Huntington's disease using lithium and rapamycin," Human Molecular Genetics, vol. 17, No. 2, Jan. 2008 (pp. 170-178).
Sarkar et al., "Rapamycin and mTOR-independent autophagy inducers ameliorate toxicity of polyglutamine-huntingtin and related proteinopathies," Cell Death and Differentiation, vol. 16, No. 1, Jan. 2009 (pp. 46-56).
Serra et al., "NVP-BEZ235, a dual PI3K/mTOR inhibitor, prevents PI3K signaling and inhibits the growth of cancer cells with activating PI3K mutations," Cancer Research, vol. 68, No. 19, Oct. 2008 (pp. 8022-8030).
Shimatani et al., "PD-1+ memory phenotype CD4+ T cells expressing C/EBP underlie T cell immunodepression in senescence and

(56) References Cited

OTHER PUBLICATIONS leukemia," Proceedings of the National Academy of Sciences of the United States of America, vol. 106, No. 37, Sep. 2009 (pp. 15807-15812).

U.S. Appl. No. 16/361,822 of Mannick et al., filed Mar. 22, 2019.

United States Securities and Exchange Commission "Form 8-K: Current Report Pursuant to Section 13 or 15(d) of the Securities Exchange Act of 1934: RESTORBIO, INC." Jul. 25, 2018.

Watanabe et al., "Abstract A167: A phase I study of single-agent BEZ235 (SDS sachet), once- or twice-daily, in Japanese patients with advanced solid tumors," Proceedings of the AACR-NCI-EORTC International Conference: Molecular Targets and Cancer Therapeutics, Oct. 19-23, 2013, Boston, MA. Philadelphia (PA): AACR; Molecular Cancer Therapeutics 2013, vol. 12, No. 11 Suupl (2 pages).

Weinberger et al., "Biology of Immune Responses to Vaccines in Elderly Persons," Clinical Infectious Diseases, vol. 46, No. 7, Apr. 2008 (pp. 1078-1084).

Wilkinson et al., "Rapamycin slows aging in mice," Aging Cell, vol. 11, No. 4, Aug. 2012 (pp. 675-682).

Withers et al., "S6 Kinase and Ageing," Abstract, British Society for Research on Ageing, Annual Scientific Meeting, Sep. 2-4, 2013, University of East Anglia, Norwich.

Zhang et al., "Aging Leads to Disturbed Homeostasis of Memory Phenotype CD8+ Cells," Journal of Experimental Medicine, vol. 195, No. 3, Feb. 2002 (pp. 283-293).

Zhou et al., "Updates of mTOR inhibitors," Anticancer Agents in Medicinal Chemistry, vol. 10, No. 7, Sep. 2010 (pp. 571-581).

| Day/Week | Screening | Baseline | Treatment | | | | | | | End of Study |
|---|---|---|---|---|---|---|---|---|---|---|
| | D -28 to -1 | Day 0 | Week 1 | Week 2 | Week 4 | Week 6 | Week 8 | Week 12 | | Week 13 |
| Visit Window (relative to previous visit) | | | ± 3 days | ± 5 days | ± 5 days | ± 5 days | ± 5 days | ± 5 days | | ± 5 days |
| Study treatment period | | | $X^1$ (Cohort 1-5 Treatment – up to 12 weeks) | | | | | | | |
| Informed Consent | X | | | | | | | | | |
| Incl./ Excl. Criteria | X | $X^2$ | | | | | | | | |
| Med. History/ Current med. conditions | X | $X^2$ | | | | | | | | |
| Mod.Hoehn and Yahr assessment | X | | | | | | | | | X |
| Demography | X | | | | | | | | | |
| Physical exam | X | $X^3$ | $X^3$ | $X^3$ | $X^3$ | $X^3$ | $X^3$ | $X^3$ | | X |
| Day/Week | D -28 to -1 | Day 0 | Week 1 | Week 2 | Week 4 | Week 6 | Week 8 | Week 12 | | Week 13 |
| Visit Window (relative to previous visit) | | | ± 3 days | ± 3 days | ± 3 days | ± 5 days | ± 5 days | ± 5 days | | ± 5 days |
| HIV/Hep (B and C), HBsAg screen | X | | | | | | | | | |
| Pregnancy test[4] | $X^{5a}$ | $X^{5b}$ | $X^{5b}$ | $X^{5b}$ | $X^{5b}$ | $X^{5b}$ | $X^{5b}$ | $X^{5b}$ | | $X^{5b}$ |
| Randomization | | X | | | | | | | | |

FIG 4

| Day/Week | Screening | Baseline | Treatment | | | | | | End of Study |
|---|---|---|---|---|---|---|---|---|---|
| | D -28 to -1 | Day 0 | Week 1 | Week 2 | Week 4 | Week 6 | Week 8 | Week 12 | Week 13 |
| Visit Window (relative to previous visit) | | | ± 3 days | ± 5days | ± 5 days | ± 5 days | ±5 days | ±5 days | ±5 days |
| Dispense/Return study drug | | X[6] | X[6a] | X[6a] | X[6a] | X[6a] | X[6a] | X[6b] | |
| Body height | X | | | | | | | | |
| Body weight | X | X | X | X | X | X | X | X | X |
| Respiratory rate | X | X | X | X | X | X | X | X | X |
| Body temp.[7] | X | X | X | X | X | X | X | X | X |
| Blood pressure / Pulse rate[8] | X | X | X | X | X | X | X | X | X |
| ECG eval. | X | | | X | X | | | | X |
| Hematology, Blood chemistry, Urinalysis | X | X | X | X | X | X | X | X | X |
| Coagulation, Lipid profile, Glucose (serum), HbA1c | X | | | | X | | X | | |
| Montreal Cognitive Assessment | | X | | | | | | X | |
| Day/Week | D -28 to -1 | Day 0 | Week 1 | Week 2 | Week 4 | Week 6 | Week 8 | Week 12 | Week 13 |
| Visit Window (relative to previous visit) | | | ± 3 days | ± 5 days | ± 5 days | ±5 days | ±5 days | ±5 days | ±5 days |

FIG. 5A

| | Screening | Baseline | Treatment | | | | | | | End of Study |
|---|---|---|---|---|---|---|---|---|---|---|
| Timed Up and Go Test (TUG) | | X | | | | | | | X | |
| Wearable device measurements | X | X | | | | | X | | X | |
| Prior and Concomitant Medications | | | | | X | | | | | |
| Adverse Events | | | As applicable | | | | | | | |
| Serious Adverse Events | | | As applicable | | | | | | | |
| UPDRS (part 1-4) | | X | | | | | | | X | |
| Parkinson's Disease Quality of Life – 39 (PDQ-39) | | X | | | | | | | X | |
| Epworth Sleepness Scale (ESS) | | X | | | | | | | X | |
| Day/Week | D -28 to -1 | Day 0 | Week 1 | Week 2 | Week 4 | Week 6 | Week 8 | | Week 12 | Week 13 |
| Visit Window | | | ± 3 days | ± 3 days | ± 3 days | ± 5 days | ± 5 days | | ± 5 days | ± 5 days |
| PK draw (dactolisib - plasma and sirolimus – whole blood) | | X[9] | X[9] | X[9] | X[9] | X[9] | X[9] | | X[9] | |
| CSF draw (dactolisib and sirolimus) | | X[10] | | | | | | | X[10] | |

FIG. 5B

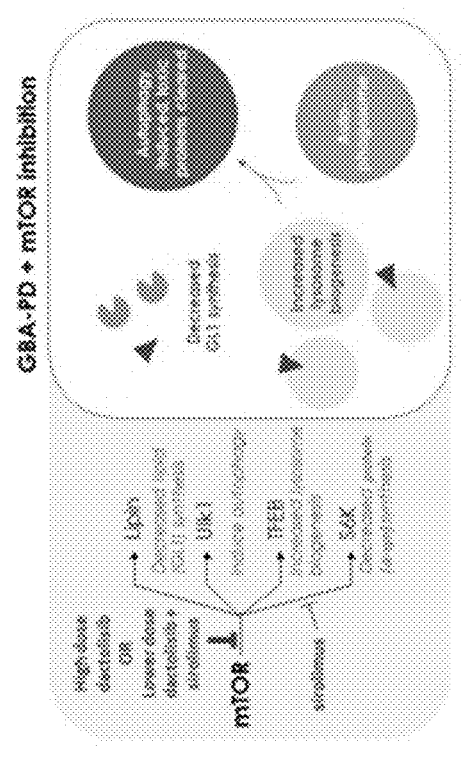
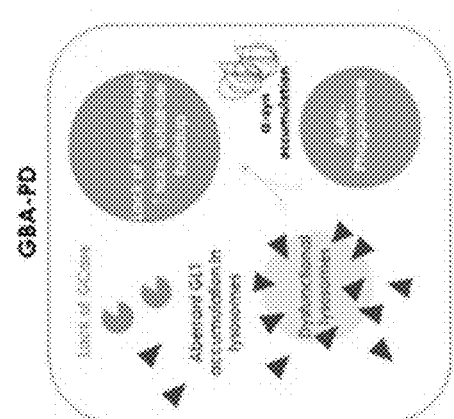
FIG. 9

| Pre-Treatment Period | | | Treatment Period | | | | End of Study |
|---|---|---|---|---|---|---|---|
| Visit Number | 1 | 2 | 3 | 4 | 5 | 6 | 7 |
| Visit Name | Screening | Baseline | Day 0 | Week 1 | Week 2 | Week 3 | Week 4 |
| Visit Window (Relative to previous visit) | Days -21 to -8 | Day -7 | +3 days | ± 3 days | ± 3 days | ± 3 days | ± 3 days |
| Informed Consent | X | | | | | | |
| Inclusion/Exclusion criteria | X | X$^1$ | X$^1$ | | | | |
| Medical History/Current medical conditions | X | X$^1$ | X$^1$ | | | | |
| Demography | X | | | | | | |
| Prior and Concomitant Medications | X | X | X | X | X | X | X |
| Physical examination | X | X$^2$ | X$^2$ | X | X$^2$ | X$^2$ | X |
| Modified Hoehn and Yahr (mH&Y) assessment | X | | | | | | |
| Body height | X | X | X | X | X | X | X |
| Body weight | X | | | | | | X |

FIG. 12A

| | Pre-Treatment Period | | Treatment Period | | | | | End of Study |
|---|---|---|---|---|---|---|---|---|
| Body temperature,[3] Respiratory rate, Blood pressure (BP), Pulse rate (HR)[4] | X | X | X | X | X | X | X | X |
| Orthostatic vital signs (supine and standing BP and HR) | X | X | X[5] | X | | X | X | X |
| ECG evaluation | X | | | X | | X | | X |
| HIV/Hepatitis (B and C), HBsAg screen | X | | | | | | | |
| Pregnancy test[6] | X[6a] | X[6b] | X[6b] | X[6b] | X[6b] | X[6b] | X[6b] | X[6b] |
| Hematology, Blood chemistry, Urinalysis | X | | X | X | X | X | X | X |
| Coagulation, Lipid profile,[7] HbA1c | X | | | | X | | | X |
| Randomization | | | X | | | | | |
| Dispense/Return study drug (IP) | | | X[8a] | X[8b] | X[8b] | | X[8c] | |
| Wearable device activity | | X[9a] | X[9b] | | | | X[9a] | X[9b] |
| Adverse Events & Serious Adverse Events | | | | | X | | | |

FIG. 12B

| Pre-Treatment Period | | Treatment Period | | | End of Study |
|---|---|---|---|---|---|
| UPDRS (part 1-4) | X | | | | X |
| Columbia Suicide Severity Rating Scale (C-SSRS) | X | X | X | | X |
| Parkinson's Disease Quality of Life – 39 (PDQ-39) | X | | | | X |
| Epworth Sleepiness Scale (ESS) | X | | | | X |
| PK draw (dactolisib: plasma; sirolimus: whole blood)[10] | | X (minus 1h; 1h; 2h; 4h) | X (8h) | X (24h) | X (minus 1h; 1h; 2h; 4h) | X (Trough) |
| Exploratory biomarkers[11] | X | | | X | |
| CSF draw (PK and exploratory biomarkers)[12] | X | | | X (4h post dose) | |

COMBINATION THERAPIES

CROSS-REFERENCE TO RELATED APPLICATIONS

This application claims the benefit under 35 U.S.C. § 119(e) of U.S. Provisional Application No. 62/629,636, filed on Feb. 12, 2018, U.S. Provisional Application No. 62/765,006, filed Aug. 17, 2018, and U.S. Provisional Application No. 62/751,263, filed Oct. 26, 2018, the contents of all of which are incorporated herein in their entireties by reference thereto.

TECHNICAL FIELD OF THE INVENTION

The present invention provides methods and pharmaceutical compositions for the treatment or prevention of autophagy-related diseases, disorders, or conditions.

BACKGROUND OF THE INVENTION

Autophagy is the process wherein cells transport intracellular constituents such as proteins, lipids, and organelles, to the lysosome for degradation and recycling. The degradation and recycling of damaged organelles and toxic aggregation prone proteins is essential for maintaining cellular homeostasis.

In recent years, studies have shown that the dysregulation of autophagy plays an important role in various diseases, such as, for example, cancer and neurodegenerative disorders, infectious, cardiovascular, pulmonary, hepatic, metabolic and inflammatory diseases. In many of these diseases toxic protein aggregates accumulate, interfering with normal cellular function. Re-establishing normal autophagy or the enhancement of autophagy may provide a valuable means for treating such diseases characterized by abnormal autophagy and/or abnormal aggregation of, e.g., toxic protein aggregates. Accordingly, there remains a need for new treatments that ameliorate abnormal autophagy and/or restore normal autophagy.

BRIEF DESCRIPTION OF THE DRAWINGS

FIG. 4 FIG. 5A and FIG. 5B depict the assessment schedule for treating patients with glucocerebrosidase gene (GBA) mutations-associated Parkinson's disease (HIV=human immunodeficiency virus; RNA=ribonucleic acid; CSF=cerebrospinal fluid; [1]Study Drug treatment period starts at Day 0 up to Week 12; [2]Review of inclusion/exclusion criteria and current medical conditions is required at baseline evaluation; [3]Targeted Physical exams may be performed at Day 0, and Weeks 1, 2, 4, 6, 8, and 12; [4]Women of child bearing potential only; [5a]Pregnancy test at screening will be a serum test (hCG); [5b]Pregnancy test at Day 0, and Weeks 1, 2, 4, 6, 8, 12 and 13 will be urine pregnancy tests (hCG); [6]Study drugs are dispensed at Day 0 and the first dose is administered at the site (in the case of lost or damaged IP, IP can be dispensed at any site visit); [6a]Patients will not be dispensed new study drug at these visits. They will just bring their remaining supply of study drug to the site for pill count; [6b]At treatment completion, the final IP accountability will be performed; [7]Body temperature may be oral or tympanic; [8]Seated blood pressure and pulse measurements are required for all visits; [9]PK time points will include minus-1 hour (±30 min), 1 hour (±15 min), 2 hours (±30 minutes), 4 hours (±30 minutes), 8 hours (±30 minutes), 12 hours (±30 minutes), 24 hours (±1 hour) (Time points will be distributed over visits at weeks 2, 4, 6, 8 and 12); [10]CSF draw at Day 0 pre-dose and Week 12 at Tmax).

FIG. 9 summarizes the potential impact of mTOR inhibition in GBA-PD.

FIG. 12A, FIG. 12B, and FIG. 12C depict the assessment schedule for treating patients with Parkinson's disease. HIV=human immunodeficiency virus; ECG=electrocardiogram; HbA1C=hemoglobin A1C; IP=investigational product (study drug); UPDRS=Unified Parkinson's Disease Rating Scale; PK=pharmacokinetic; CSF=cerebrospinal fluid; [1]A review of inclusion/exclusion criteria and current medical conditions is required at Screening, Baseline and Treatment Period Day 0 evaluations prior to any additional testing, evaluations, or drug administration being performed at these visits; [2]Targeted Physical exams may be performed at Baseline, Day 0, and Weeks 2, 3 and 4 visits. A Full exam should be done at Screening, Week 1 and End of Study visits; [3]Body temperature may be oral or tympanic; [4]Seated or supine blood pressure and pulse measurements are required for all visits; [5]Orthostatic vital signs at this visit should be collected at least 4 hours post first study drug dose on this day; [6]Women of child bearing potential only; [6a]Pregnancy test at Screening will be a serum test (hCG); [6b]Pregnancy test at Baseline, Day 0, and Weeks 1, 2, 3, and 4 will be urine pregnancy tests (hCG); [7]These lipid profiles are not required to be collected while fasting. However, fasting lipid profiles should be added/drawn under the appropriate conditions. This fasting lipid profile may be drawn at an unscheduled visit or at the next scheduled visit; [8a]Study drugs are dispensed at Treatment Day 0 and the first dose is administered at the site (in the case of lost or damaged IP, IP can be dispensed at any site visit); [8b]Patients will not be dispensed new study drug at these visits. They will just bring their remaining supply of study drug to the site for pill count; [8c]At treatment completion, the final IP accountability will be performed; [9a]Wearable device sent home with patient; [9b]Wearable device returned to site and data uploaded; [10]PK time points in hours (h) . pre-dose, −1 hour±30 mins; post dose, 1 hour±15 min; post dose, 2 hours±30 mins; post dose, 4 hours±30 mins; post dose, 8 hours±60 mins; and post dose, 24 hours±2hours. Trough (may be anytime >4 days following last dose at Week 4 visit); [11]See Example 8 for biomarkers; [12]CSF should at drawn at Baseline visit, and at Week 4 visit at Tmax (4 h post on-site dose ±30 mins).

Figure 1:
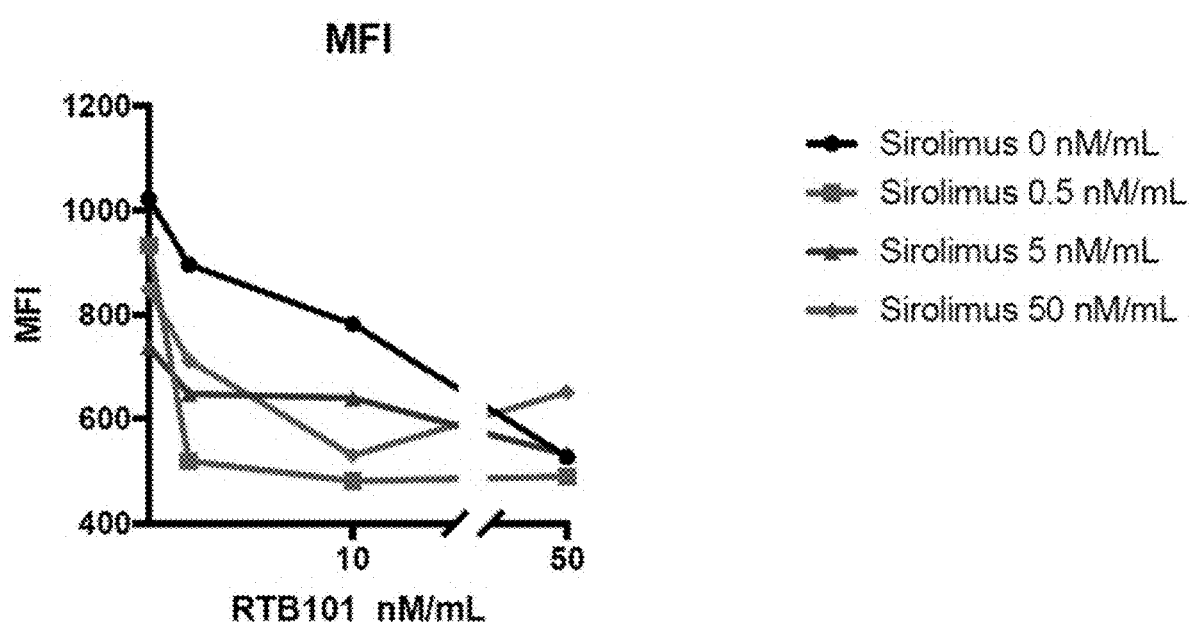
FIG. 1 shows the mean fluorescence of patient derived human alpha-1 anti-trypsin deficient (Pizz) hepatocytes treated with combinations of RTB101 and sirolimus in a FACS assay for intracellular AAT.

DETAILED DESCRIPTION OF CERTAIN EMBODIMENTS mTOR Inhibitors

In mammalian cells, the target of rapamycin (mTOR) kinase exists as a multiprotein complex described as the mTORC1 complex or mTORC2 complex, which senses the availability of nutrients and energy and integrates inputs from growth factors and stress signaling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: S6 kinase, which in turn phosphorylates ribosomal protein S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as S6K1 from accessing mTOR and being phosphorylated. Rapamycin and rapalogues such as everolimus have gained clinical relevance by inhibiting hyperactivation of mTOR associated with both benign and malignant proliferation disorders. Exemplary such rapalogues are known to those of skill in the chemical and medical arts.

RAD001 is otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone and the chemical structure according to Formula I:

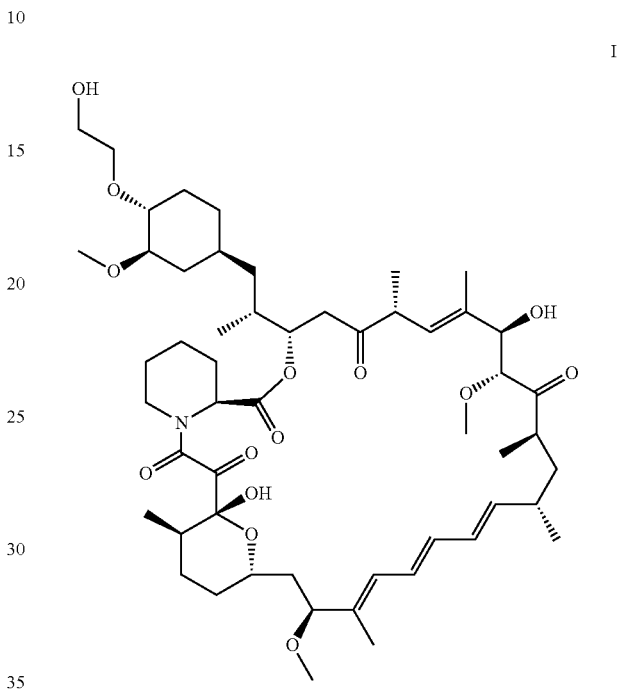

Everolimus is an FDA approved drug for the treatment of advanced kidney cancer and is still being investigated in several other phase III clinical trials in oncology. Preclinical studies have shown that everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely S6 kinase (S6K) and the downstream S6K substrate S6. However, everolimus (and other rapamycin analogues) has little or no effect at inhibiting the priming phosphorylation events in 4EBP1 (T37/46), which is implicated as a key driver in tumorigenesis and maintenance. Allosteric mTOR inhibitors like everolimus (and other rapamycin analogues) have little or no effect at inhibiting the mTORC2 pathway, or its resulting activation of Akt signaling. Further examples of allosteric mTOR inhibitors include sirolimus (rapamycin, AY-22989), 40-[3-hydroxy-2-(hydroxymethyl)-2-methyl-propanoate]-rapamycin (also called temsirolimus or CCI-779) and deforolimus (AP-23573/MK-8669).

Alternatively, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

As used herein, "RAD001" and "everolimus" are equivalent and used interchangeably.

RTB101 (also known as BEZ235 and dactolisib) is a catalytic mTOR inhibitor, having the chemical name 2-methyl-2-[4-(3-methyl-2-oxo-8-quinolin-3-yl-2,3-dihydro-imidazo[4,5-c]quinolin-1-yl)-phenyl]-propionitrile and the chemical structure according to Formula II:

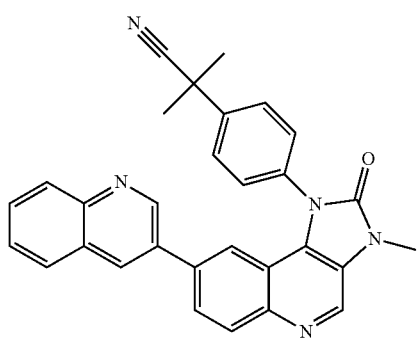

RTB101 may also be used in its monotosylate salt form. The synthesis of RTB101 is described in WO 2006/122806.

As a catalytic mTOR inhibitor RTB101 is capable of shutting down the complete function of mTORC1 complex, including both the rapamycin sensitive (phosphorylation of S6K, and subsequently phosphorylation of S6) and rapamycin insensitive (phosphorylation of 4EBP1) functions. RTB101 has a differential effect according to the drug concentration used, whereby mTOR inhibition predominates at a low concentration (less than 100 nmol/L) but dual PI3K/mTOR inhibition at relatively higher concentrations (approximately 500 nmol/L) (V. Serra et al., Cancer Res. 68(19): 8022-30 (2008)).

As used herein, "RTB101", "BEZ235", and "dactolisib" are equivalent and used interchangeably.

A further catalytic mTOR inhibitor described in the literature is CCG168 (otherwise known as AZD-8055; C. M. Chresta et al., Cancer Res. 70(1): 288-98 (2010)) which has the chemical name {5-[2,4-bis-((S)-3-methyl-morpholin-4-yl)-pyrido[2,3-d]pyrimidin-7-yl]-2-methoxy-phenyl}-methanol and the chemical structure according to Formula III:

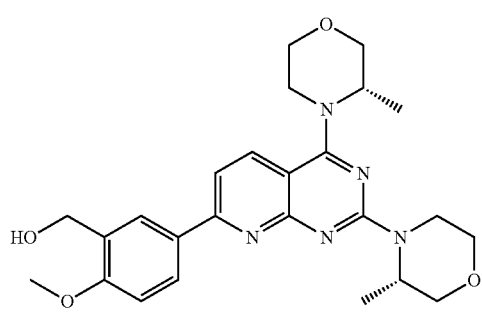

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO 2006/122806), Ku-0063794 (J. M. Garcia-Martinez et al., Biochem J. 421(1): 29-42 (2009)) and WYE-354 (K. Yu et al., Cancer Res. 69(15): 6232-40 (2009)).

Parkinson's Disease

Parkinson's disease (PD) is the second most common neurodegenerative condition, impacting approximately 0.3% of the world's population as a whole and 1% of persons older than 65 (R. L. Nussbaum & C. E. Ellis, N. Engl. J. Med. 348(14): 1356-64 (2003)). Hallmark pathological features of the disease include degeneration and loss of dopaminergic neurons in the substantia nigra pars compacta and the presence of intracytoplasmic inclusions known as Lewy bodies (C. W. Olanow & W. G. Tatton, Annu. Rev. Neurosci. (22(1): 123-44 (1999)).

Numerous attempts have been made over the years, however, there are still no reliable disease-modifying or neuroprotective treatments for PD available (A. AlDakheel et al., Neurotherapeutics 11(1): 6-23 (2014)). While diagnostic and therapeutic options have become more widely available and accessible, there is no cure and most therapies focus on ameliorating symptoms (B. S. Connolly & A. E. Lang, JAMA 311(16):1670-83 (2014)). Dopamine replacement therapies, such as levodopa, provide improvement for most patients. However, long-term treatment using L-DOPA inevitably results in the development of dyskinesia and declining motor function.

A substantial component of PD's characteristic Lewy bodies is misfolded α-synuclein (M. G. Spillantini et al., Nature 388(6645): 839-40 (1997)). In Parkinson's disease, misfolded α-synuclein has been shown to interfere with normal chaperone-mediated autophagy (CMA) facilitating accumulation and aggregation of Lewy bodies (M. A. Lynch-Day et al., Cold Spring Harbor Perspectives in Medicine. 2(4), a009357. http://doi.org/10.1101/cshperspect.a009357 (2012)).

Further, between 3-30% of patients with PD have mutations in the glucocerebrosidase gene (GBA) (E. Sidransky & G. Lopez, Neurology 11(11): 986-98 (2012)). The presence of a GBA mutation is correlated with a higher risk of developing PD and becoming symptomatic at a younger age, even if the individual is heterozygous for the mutation (E. Sidransky et al., N. Engl. J. Med. 361(17): 1651-61 (2009)). Lose of function mutations of GBA reduce or eliminate glucocerebrosidase (GCase) activity, resulting in the accumulation of glucosylceramide (GL1) within lysosomes. This lysosomal dysfunction contributes to aberrant autophagy, and may contribute to the accumulation of protein aggregates, include alpha synuclein containing Lewy bodies.

The inhibition of mTORC1 has been shown to increase autophagy (A. Trocoli & M. Djavaheri-Mergny, Am. J. Cancer Res. 1(5): 629-49 (2011)). Without wishing to be bound by any particular theory, inducing or augmenting autophagy by inhibiting mTOR may decrease Lewy body accumulation and be useful for treating or preventing a disease, disorder, or condition associated therewith.

Huntington's Disease

Huntington's disease (HD) is characterized by selective neuronal cell death in cortex and striatum which leads to progressive dementia, motor impairment, and personality changes. A major molecular feature in HD is the gradual appearance of cytosolic and nuclear polyQ inclusions which runs in parallel to disease onset and progression. In the striatum, medium-sized spiny neurons (MNs) exhibit a gradual increase of polyQ inclusions, decrease of DARPP-32 and global axonal degeneration. (The Huntington's Disease Collaborative Research Group (1993), S. W. Davies et al., Cell 90(3): 537-48 (1997), J. A. Bibb et al., Proc. Natl. Acad. Sci. U.S.A. 97(12): 6809-14 (2000), and R. Luthi-Carter et al., Hum. Mol. Genet. 9(9): 1259-71 (2000)).

To follow striatal degeneration, an ex vivo model for Huntington's disease has been developed using corticostriatal slice cultures from the R6/2 mouse model. This approach is based on the interface method and yields slice cultures that can be maintained for several weeks (I. Galimberti, et al., Neuron 50(5): 749-63 (2006), N. Gogolla et al., Nat. Protoc. 1(3): 1165-71 (2006), and I. Galimberti et al., Neuron 65(5): 627-42 (2010)). When the R6/2 slices were investigates at different weeks in vitro, a gradual increase of polyQ inclusions, a decrease of DARPP-32, and global neurofilament loss in the striatum was observed.

Studies in R6/2 slices were initiated to investigate whether the clearance of mutant Huntingtin (mHtt) is sufficient to preserve striatal degeneration. In particular, autophagy was induced by inhibiting the mTOR pathway from 14 to 21 days in vitro (DIV). mTOR inhibition induced autophagy, reduced polyQ inclusions and preserved DARPP-32 and neurofilament loss in striatum. Interestingly, a low-dose combination of an allosteric mTOR inhibitor (everolimus) and a catalytic mTOR inhibitor (RTB101 or CCG168) worked synergistically compared to 250 nM everolimus and 50 nM RTB101 single treatment. Moreover, the combinatorial mTOR inhibition of 250 nM everolimus/30 nM RTB101 preserved striatal degeneration at a 10-fold lower RTB101 concentration. Thus, the results described herein suggest that low-dose combinations of an allosteric mTOR inhibitor and a catalytic mTOR inhibitor reduce striatal degeneration in R6/2 slices and represent a therapeutic opportunity for HD treatment. This unexpected synergistic interaction allows a reduction in the required dose, leading to fewer side effects and enhancement of clinical effectiveness.

Alpha-1 Antitrypsin Related Diseases

Alpha-1 Antitrypsin (AAT) is a serine protease inhibitor in the serpin superfamily secreted mainly by liver hepatocytes, with the lung epithelial and phagocytes as secondary sources (N. Luisetti & N. Seersholm, Thorax 59(2):164-69 (2004)). The main role of AAT is the inhibition of serine proteases, in particular human neutrophil elastase (HNE) (J. Travis & G. S. Salvensen, Annu. Rev. Biochem. 52:655-709 (1983)).

AAT deficiency is a misleadingly common hereditary disease (F. J. de Serres, Environ. Health Perspect. 111(6): 1851-54 (2003); F. J. de Serres, Chest 122(5): 1818-29 (2002)). Persons having decreased levels of AAT are predisposed to developing various conditions such as, for example, chronic obstructive pulmonary disease (COPD) (D. L. DeMeo & E. K. Silverman, Thorax 59(3): 259-64 (2004)), panacinar emphysema, and cirrhosis (A. A. Wilson et al., Am. J. Respire. Cell Mol. Biol. 39(2): 133-41 (2008)). Normal serum levels of AAT vary between about 20 to 40 µM (C. B. Laurell & S. Eriksson, Clin. Chim. Acta. 16(2): 199-203 (1967)). However, the gene locus coding for AAT is highly polymorphic with the amount of serum AAT depending on the specific mutation(s) present (A. Riva & I. S. Kohane, Bioinformatics 18(12): 1681-85 (2002); L. Fregonese & J. Stolk, Orphanet. J. Rare Dis. 3(16). doi:10.1186/1750-1172-3-16 2008)). Persons possessing the PiZZ (Z-AAT) mutation suffer from severe serum AAT deficiency and a predisposition to developing liver diseases, disorders, or conditions due to AAT misfolding, polymerization, and aggregation in the endoplasmic reticulum (ER) of hepatocytes. Individuals possessing the PiNull, PiSZ, and PiZZ mutations are in significant risk of developing lung disease such as emphysema and COPD.

Z AAT aggregate accumulation has been shown to activate the unfolded protein response (UPR), increasing autophagosome formation and efflux in an effort to clear the intracellular aggregates (A. A. Wilson et al., Stem Cell Reports 4(5): 873-85 (2015)). Further, augmentation of autophagic flux has been shown to ameliorate the accumulation of Z AAT aggregates. Without wishing to be bound by any particular theory, inducing or augmenting autophagy by inhibiting mTOR may be useful in treating diseases, disorders, or conditions associated with AAT deficiency, for instance a disease, disorder, or condition as described below and herein.

Provided Methods

In some embodiments, the present invention provides a method for the treatment or prevention of an autophagy-related disease, disorder, or condition in a subject in need thereof, comprising administering to the subject an effective amount of a combination of an allosteric mTOR inhibitor and a catalytic mTOR inhibitor. Exemplary such autophagy-related diseases, disorders, or conditions include, but are not limited to, cancer, Amyotrophic Lateral Sclerosis (ALS), Alzheimer's disease, Huntington's disease, Parkinson's disease, static encephalopathy of childhood with neurodegeneration in adulthood (SENDA), bacterial infections, viral infections, Tuberculosis, Crohn's disease, systemic lupus erythematosus, cardiovascular diseases, metabolic diseases (e.g., Paget's disease, insulin resistance and diabetes), pulmonary diseases (e.g., COPD, cystic fibrosis, asthma, emphysema, idiopathic pulmonary fibrosis), Vici syndrome, and diseases, disorders, or conditions associated with alpha-1 antitrypsin deficiency (e.g., cirrhosis, hepatitis, hepatomegaly, jaundice, and liver failure).

In some embodiments, the present invention provides a method for the treatment or prevention of an autophagy-related disease, disorder, or condition, in a subject in need thereof, comprising administering to the subject an effective amount of a combination of an allosteric mTOR inhibitor and a catalytic mTOR inhibitor wherein the allosteric mTOR inhibitor is selected from everolimus, sirolimus, temsirolimus, zotarolimus, umirolimus and deforolimus, and the catalytic mTOR inhibitor is selected from RTB101, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In some embodiments, the present invention provides a method for the treatment or prevention of an autophagy-related disease, disorder, or condition, in a subject in need thereof, comprising administering to the subject an effective amount of a combination of everolimus or sirolimus and RTB101.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor is selected from everolimus, sirolimus, temsirolimus, zotarolimus, umirolimus and deforolimus, and the catalytic mTOR inhibitor is selected from RTB101, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of everolimus or sirolimus and RTB101.

In some embodiments, the present invention provides a method for the treatment or prevention of an autophagy-related disease, disorder, or condition, in a subject in need thereof, comprising administering to the subject an effective amount of a combination of everolimus or Sirolimus and RTB101 wherein the everolimus or sirolimus is administered at a dose of about 1.5 mg/kg/day and the RTB101 is administered at a dose of about 2.5 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 1.4 and 1.6 mg/kg/day and the RTB101 is administered at a dose of between 2.4 and 2.6 mg/kg/day; the everolimus or sirolimus is administered at a dose of between about 1.3 and 1.7 mg/kg/day and the RTB101 is administered at a dose of between about 2.3 and 2.7 mg/kg/day; the everolimus or sirolimus is administered at a dose of between about 1.2 and 1.8 mg/kg/day and the RTB101 is administered at a dose of between about 2.2 and 2.8 mg/kg/day; the everolimus or sirolimus is administered at a dose of between about 1.1 and 1.9 mg/kg/day and the RTB101 is administered at a dose of between about 2.1 and 2.9 mg/kg/day; the everolimus or sirolimus is administered at a dose of between about 1.0 and 2.0 mg/kg/day and the RTB101 is administered at a dose of between about 2.0 and 3.0 mg/kg/day; the everolimus or sirolimus is administered at a dose of between about 0.8 and 2.2 mg/kg/day and the RTB101 is administered at a dose of between about 1.8 and 2.6 mg/kg/day; the everolimus or sirolimus is administered at a dose of between about 0.6 and 2.4 mg/kg/day and the RTB101 is administered at a dose of between about 1.6 and 2.8 mg/kg/day; the everolimus or sirolimus is administered at a dose of between about 0.4 and 2.6 mg/kg/day and the RTB101 is administered at a dose of between about 1.4 and 3.0 mg/kg/day; the everolimus or sirolimus is administered at a dose of between about 0.2 and 2.8 mg/kg/day and the RTB101 is administered at a dose of between about 1.0 and 3.5 mg/kg/day; the everolimus or sirolimus is administered at a dose of between about 0.01 and 3.0 mg/kg/day and the RTB101 is administered at a dose of between about 0.5 and 4.0 mg/kg/day; the everolimus or sirolimus is administered at a dose of between about 0.01 and 5.0 mg/kg/day and the RTB101 is administered at a dose of between about 0.01 and 5.0 mg/kg/day; or the everolimus or sirolimus is administered at a dose of between about 0.01 and 10.0 mg/kg/day and the RTB101 is administered at a dose of between about 0.01 and 10.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 0.01 and 20.0 mg/kg/day and the RTB101 is administered at a dose of between about 0.01 and 100.0 mg/kg/day; the everolimus or sirolimus is administered at a dose of between about 0.01 and 30.0 mg/kg/day and the RTB101 is administered at a dose of between about 0.01 and 200.0 mg/kg/day; the everolimus or sirolimus is administered at a dose of between about 0.01 and 40.0 mg/kg/day and the RTB101 is administered at a dose of between about 0.01 and 300.0 mg/kg/day; or the everolimus or sirolimus is administered at a dose of between about 0.01 and 50.0 mg/kg/day and the RTB101 is administered at a dose of between about 0.01 and 400.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.001 and 100.0 mg/kg/day and the RTB101 is administered at a dose of between about 0.01 and 500.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 100.0 mg/kg/day and the RTB101 is administered at a dose of between about 0.01 and 400.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 50.0 mg/kg/day and the RTB101 is administered at a dose of between about 0.01 and 400.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of about 1.5 mg/kg/week and the RTB101 is administered at a dose of about 2.5 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 1.4 and 1.6 mg/kg/week and the RTB101 is administered at a dose of between 2.4 and 2.6 mg/kg/week; the everolimus or sirolimus is administered at a dose of between about 1.3 and 1.7 mg/kg/week and the RTB101 is administered at a dose of between about 2.3 and 2.7 mg/kg/week; the everolimus or sirolimus is administered at a dose of between about 1.2 and 1.8 mg/kg/week and the RTB101 is administered at a dose of between about 2.2 and 2.8 mg/kg/week; the everolimus or sirolimus is administered at a dose of between about 1.1 and 1.9 mg/kg/week and the RTB101 is administered at a dose of between about 2.1 and 2.9 mg/kg/week; the everolimus or sirolimus is administered at a dose of between about 1.0 and 2.0 mg/kg/week and the RTB101 is administered at a dose of between about 2.0 and 3.0 mg/kg/week; the everolimus or sirolimus is administered at a dose of between about 0.8 and 2.2 mg/kg/week and the RTB101 is administered at a dose of between about 1.8 and 2.6 mg/kg/week; the everolimus or sirolimus is administered at a dose of between about 0.6 and 2.4 mg/kg/week and the RTB101 is administered at a dose of between about 1.6 and 2.8 mg/kg/week; the everolimus or sirolimus is administered at a dose of between about 0.4 and 2.6 mg/kg/week and the RTB101 is administered at a dose of between about 1.4 and 3.0 mg/kg/week; the everolimus or sirolimus is administered at a dose of between about 0.2 and 2.8 mg/kg/week and the RTB101 is administered at a dose of between about 1.0 and 3.5 mg/kg/week; the everolimus or sirolimus is administered at a dose of between about 0.01 and 3.0 mg/kg/week and the RTB101 is administered at a dose of between about 0.5 and 4.0 mg/kg/week; the everolimus or sirolimus is administered at a dose of between about 0.01 and 5.0 mg/kg/week and the RTB101 is administered at a dose of between about 0.01 and 5.0 mg/kg/week; the everolimus or sirolimus is administered at a dose of between about 0.01 and 10.0 mg/kg/week and the RTB101 is administered at a dose of between about 0.01 and 10.0 mg/kg/week; the everolimus or sirolimus is administered at a dose of between about 0.01 and 20.0 mg/kg/week and the RTB101 is administered at a dose of between about 0.01 and 100.0 mg/kg/week; the everolimus or sirolimus is administered at a dose of between about 0.01 and 30.0 mg/kg/week and the RTB101 is administered at a dose of between about 0.01 and 200.0 mg/kg/week; the everolimus or sirolimus is administered at a dose of between about 0.01 and 40.0 mg/kg/week and the RTB101 is administered at a dose of between about 0.01 and 300.0 mg/kg/week; or the everolimus or sirolimus is administered at a dose of between about 0.01 and 50.0 mg/kg/week and the RTB101 is administered at a dose of between about 0.01 and 400.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.001 and 100.0 mg/kg/week and the RTB101 is administered at a dose of between about 0.01 and 500.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 100.0 mg/kg/week and the RTB101 is administered at a dose of between about 0.01 and 400.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 50.0 mg/kg/week and the RTB101 is administered at a dose of between about 0.01 and 400.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between at least about 2 to at least about 6 mg/week and the RTB 101 is administered at a dose of at least about 300.0 mg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 2 to about 6 mg/week and the RTB 101 is administered at a dose of at least about 300.0 mg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of about 2 mg/week and the RTB 101 is administered at a dose of about 300.0 mg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of about 4 mg/week and the RTB101 is administered at a dose of about 300.0 mg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of about 6 mg/week and the RTB101 is administered at a dose of about 300.0 mg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of about 1.5 mg/kg/week and the RTB 101 is administered at a dose of about 2.5 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 1.4 and 1.6 mg/kg/week and the RTB101 is administered at a dose of between 2.4 and 2.6 mg/kg/day; the everolimus or sirolimus is administered at a dose of between about 1.3 and 1.7 mg/kg/week and the RTB101 is administered at a dose of between about 2.3 and 2.7 mg/kg/day; the everolimus or sirolimus is administered at a dose of between about 1.2 and 1.8 mg/kg/week and the RTB101 is administered at a dose of between about 2.2 and 2.8 mg/kg/day; the everolimus or sirolimus is administered at a dose of between about 1.1 and 1.9 mg/kg/week and the RTB101 is administered at a dose of between about 2.1 and 2.9 mg/kg/day; the everolimus or sirolimus is administered at a dose of between about 1.0 and 2.0 mg/kg/week and the RTB101 is administered at a dose of between about 2.0 and 3.0 mg/kg/day; the everolimus or sirolimus is administered at a dose of between about 0.8 and 2.2 mg/kg/week and the RTB101 is administered at a dose of between about 1.8 and 2.6 mg/kg/day; the everolimus or sirolimus is administered at a dose of between about 0.6 and 2.4 mg/kg/week and the RTB101 is administered at a dose of between about 1.6 and 2.8 mg/kg/day; the everolimus or sirolimus is administered at a dose of between about 0.4 and 2.6 mg/kg/week and the RTB101 is administered at a dose of between about 1.4 and 3.0 mg/kg/day; the everolimus or sirolimus is administered at a dose of between about 0.2 and 2.8 mg/kg/week and the RTB101 is administered at a dose of between about 1.0 and 3.5 mg/kg/day; the everolimus or sirolimus is administered at a dose of between about 0.01 and 3.0 mg/kg/week and the RTB101 is administered at a dose of between about 0.5 and 4.0 mg/kg/day; the everolimus or sirolimus is administered at a dose of between about 0.01 and 5.0 mg/kg/week and the RTB101 is administered at a dose of between about 0.01 and 5.0 mg/kg/day; or the everolimus or sirolimus is administered at a dose of between about 0.01 and 10.0 mg/kg/week and the RTB101 is administered at a dose of between about 0.01 and 10.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 0.01 and 20.0 mg/kg/week and the RTB101 is administered at a dose of between about 0.01 and 100.0 mg/kg/day; the everolimus or sirolimus is administered at a dose of between about 0.01 and 30.0 mg/kg/week and the RTB101 is administered at a dose of between about 0.01 and 200.0 mg/kg/day; the everolimus or sirolimus is administered at a dose of between about 0.01 and 40.0 mg/kg/week and the RTB101 is administered at a dose of between about 0.01 and 300.0 mg/kg/day; or the everolimus or sirolimus is administered at a dose of between about 0.01 and 50.0 mg/kg/week and the RTB101 is administered at a dose of between about 0.01 and 400.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.001 and 100.0 mg/kg/week and the RTB101 is administered at a dose of between about 0.01 and 500.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 100.0 mg/kg/week and the RTB101 is administered at a dose of between about 0.01 and 500.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 50.0 mg/kg/week and the RTB101 is administered at a dose of between about 0.01 and 400.0 mg/kg/day.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of about 1.5 mg/kg/day and the RTB101 is administered at a dose of about 2.5 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 1.4 and 1.6 mg/kg/day and the RTB101 is administered at a dose of between 2.4 and 2.6 mg/kg/week; the everolimus or sirolimus is administered at a dose of between about 1.3 and 1.7 mg/kg/day and the RTB101 is administered at a dose of between about 2.3 and 2.7 mg/kg/week; the everolimus or sirolimus is administered at a dose of between about 1.2 and 1.8 mg/kg/day and the RTB101 is administered at a dose of between about 2.2 and 2.8 mg/kg/week; the everolimus or sirolimus is administered at a dose of between about 1.1 and 1.9 mg/kg/day and the RTB101 is administered at a dose of between about 2.1 and 2.9 mg/kg/week; the everolimus or sirolimus is administered at a dose of between about 1.0 and 2.0 mg/kg/day and the RTB101 is administered at a dose of between about 2.0 and 3.0 mg/kg/week; the everolimus or sirolimus is administered at a dose of between about 0.8 and 2.2 mg/kg/day and the RTB101 is administered at a dose of between about 1.8 and 2.6 mg/kg/week; the everolimus or sirolimus is administered at a dose of between about 0.6 and 2.4 mg/kg/day and the RTB101 is administered at a dose of between about 1.6 and 2.8 mg/kg/week; the everolimus or sirolimus is administered at a dose of between about 0.4 and 2.6 mg/kg/day and the RTB101 is administered at a dose of between about 1.4 and 3.0 mg/kg/week; the everolimus or sirolimus is administered at a dose of between about 0.2 and 2.8 mg/kg/day and the RTB101 is administered at a dose of between about 1.0 and 3.5 mg/kg/week; the everolimus or sirolimus is administered at a dose of between about 0.01 and 3.0 mg/kg/day and the RTB101 is administered at a dose of between about 0.5 and 4.0 mg/kg/week; the everolimus or sirolimus is administered at a dose of between about 0.01 and 5.0 mg/kg/day and the RTB101 is administered at a dose of between about 0.01 and 5.0 mg/kg/week; or the everolimus or sirolimus is administered at a dose of between about 0.01 and 10.0 mg/kg/day and the RTB101 is administered at a dose of between about 0.01 and 10.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein: the everolimus or sirolimus is administered at a dose of between about 0.01 and 20.0 mg/kg/day and the RTB101 is administered at a dose of between about 0.01 and 100.0 mg/kg/week; the everolimus or sirolimus is administered at a dose of between about 0.01 and 30.0 mg/kg/day and the RTB101 is administered at a dose of between about 0.01 and 200.0 mg/kg/week; the everolimus or sirolimus is administered at a dose of between about 0.01 and 40.0 mg/kg/day and the RTB101 is administered at a dose of between about 0.01 and 300.0 mg/kg/week; or the everolimus or sirolimus is administered at a dose of between about 0.01 and 50.0 mg/kg/day and the RTB101 is administered at a dose of between about 0.01 and 400.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.001 and 100.0 mg/kg/day and the RTB101 is administered at a dose of between about 0.01 and 500.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 100.0 mg/kg/day and the RTB101 is administered at a dose of between about 0.01 and 400.0 mg/kg/week.

In some embodiments, the present invention provides a method for the treatment or prevention of an autophagy-related disease, disorder, or condition, in a subject in need thereof, comprising administering to the subject an effective amount of a combination of everolimus or sirolimus and RTB101 wherein the everolimus or sirolimus is administered at a dose of between about 0.01 and 50.0 mg/kg/day and the RTB101 is administered at a dose of between about 0.01 and 400.0 mg/kg/week.

In some embodiments, a provided method is any of those described above and herein, wherein the autophagy-related disease, disorder, or condition is Parkinson's disease. In some such embodiments, a provided method comprises administering to a subject in need thereof an effective amount of a combination of everolimus or sirolimus and RTB101 wherein the everolimus or sirolimus is administered at a dose of between about 0.01 and 50.0 mg/kg/week and the RTB101 is administered at a dose of between about 0.01 and 500.0 mg/kg/day. In some such embodiments, the everolimus or sirolimus is administered at a dose of between about 0.1 and 50.0 mg/kg/week and the RTB101 is administered at a dose of between about 0.1 and 500.0 mg/kg/day. In some such embodiments, the everolimus or sirolimus is administered at a dose of between about 1 and 50,0 mg/kg/week and the RTB101 is administered at a dose of between about 1 and 500.0 mg/kg/day. In some such embodiments, the everolimus or sirolimus is administered at a dose of between about 2 and 45.0 mg/kg/week and the RTB101 is administered at a dose of between about 1 and 450.0 mg/kg/day. In some such embodiments, the everolimus or sirolimus is administered at a dose of between about 5 and 40.0 mg/kg/week and the RTB101 is administered at a dose of between about 10 and 450.0 mg/kg/day. In some such embodiments, the everolimus or sirolimus is administered at a dose of between about 5 and 40.0 mg/kg/week and the RTB101 is administered at a dose of between about 25 and 400.0 mg/kg/day. In some embodiments, a provided method for treating or preventing Parkinson's disease is any of those described above, wherein the amount of everolimus or sirolimus is an amount as described above but is administered biweekly, and wherein the RTB101 is administered in an amount described above daily.

In some embodiments, the autophagy-related disease, disorder, or condition is Parkinson's Disease and the everolimus or sirolimus is administered at a dose of about 5, 10, 15, 20, 25, 30, 35, 40, 45, 50, 55, 60, 65, 70, 75, 80, 85, 90, 95, or 100 mg/kg/week. In some embodiments, the autophagy-related disease, disorder, or condition is Parkinson's disease and the everolimus or sirolimus is administered at a dose of about 5, 10, 15, 20, 25, 30, 35, 40, 45, 50, 55, 60, 65, 70, 75, 80, 85, 90, 95, or 100 mg/kg/biweekly. In some such embodiments, the everolimus or sirolimus is administered at a dose of about 5, 10, 15, 20, 25, 30, 35, or 40 mg/kg/week.

In some such embodiments, the everolimus or sirolimus is administered at a dose of about 5, 10, 15, 20, 25, 30, 35, or 40 mg/kg/biweekly.

In some embodiments, the autophagy-related disease, disorder, or condition is Parkinson's Disease and RTB101 is administered at a dose of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg/kg/day.

In some embodiments, a provided method is any of those described above and herein, wherein the autophagy-related disease, disorder, or condition is Parkinson's disease. In some embodiments, a provided method comprises administering to a subject in need thereof an effective amount of a combination of everolimus or sirolimus and RTB101, wherein the everolimus or sirolimus is administered at a dose of between at least about 2 to at least about 6 mg/week and the RTB101 is administered at a dose of at least about 300 mg/week. In some such embodiments, the everolimus or sirolimus is administered at a dose of between about 2 to about 6 mg/week and the RTB101 is administered at a dose of about 300 mg/week. In some such embodiments, the everolimus or sirolimus is administered at a dose of between about 2 mg/week and the RTB101 is administered at a dose of about 300 mg/week. In some such embodiments, the everolimus or sirolimus is administered at a dose of between about 4 mg/week and the RTB101 is administered at a dose of about 300 mg/week. In some such embodiments, the everolimus or sirolimus is administered at a dose of between about 6 mg/week and the RTB101 is administered at a dose of about 300 mg/week.

In some embodiments, the autophagy-related disease, disorder, or condition is Parkinson's Disease and the everolimus or Sirolimus is administered at a dose of about 2, 2.5, 3, 3.5, 4, 4.5, 5, 5.5, or 6 mg/week.

In some embodiments, the autophagy-related disease, disorder, or condition is Parkinson's Disease and RTB101 is administered at a dose of about 300 mg/week.

In some embodiments, a provided method is any of those described above and herein, wherein the autophagy-related disease, disorder, or condition is GBA-related Parkinson's disease. In some such embodiments, a provided method comprises administering to a subject in need thereof an effective amount of a combination of everolimus or sirolimus and RTB101 wherein the everolimus or sirolimus is administered at a dose of between about 0.01 and 50.0 mg/kg/week and the RTB101 is administered at a dose of between about 0.01 and 500.0 mg/kg/day. In some such embodiments, the everolimus or sirolimus is administered at a dose of between about 0.1 and 50.0 mg/kg/week and the RTB101 is administered at a dose of between about 0.1 and 500.0 mg/kg/day. In some such embodiments, the everolimus or sirolimus is administered at a dose of between about 1 and 50.0 mg/kg/week and the RTB101 is administered at a dose of between about 1 and 500.0 mg/kg/day. In some such embodiments, the everolimus or sirolimus is administered at a dose of between about 2 and 45.0 mg/kg/week and the RTB101 is administered at a dose of between about 1 and 450.0 mg/kg/day. In some such embodiments, the everolimus or sirolimus is administered at a dose of between about 5 and 40.0 mg/kg/week and the RTB101 is administered at a dose of between about 10 and 450.0 mg/kg/day. In some such embodiments, the everolimus or sirolimus is administered at a dose of between about 5 and 40.0 mg/kg/week and the RTB101 is administered at a dose of between about 25 and 400.0 mg/kg/day. In some embodiments, a provided method for treating or preventing Parkinson's disease is any of those described above, wherein the amount of everolimus or sirolimus is an amount as described above but is administered biweekly, and wherein the RTB101 is administered in an amount described above daily.

In some embodiments, the autophagy-related disease, disorder, or condition is GBA-related Parkinson's Disease and the everolimus or sirolimus is administered at a dose of about 5, 10, 15, 20, 25, 30, 35, 40, 45, 50, 55, 60, 65, 70, 75, 80, 85, 90, 95, or 100 mg/kg/week. In some embodiments, the autophagy-related disease, disorder, or condition is Parkinson's disease and the everolimus or sirolimus is administered at a dose of about 5, 10, 15, 20, 25, 30, 35, 40, 45, 50, 55, 60, 65, 70, 75, 80, 85, 90, 95, or 100 mg/kg/biweekly. In some such embodiments, the everolimus or sirolimus is administered at a dose of about 5, 10, 15, 20, 25, 30, 35, or 40 mg/kg/week. In some such embodiments, the everolimus or sirolimus is administered at a dose of about 5, 10, 15, 20, 25, 30, 35, or 40 mg/kg/biweekly.

In some embodiments, the autophagy-related disease, disorder, or condition is GBA-related Parkinson's Disease and RTB101 is administered at a dose of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg/kg/day.

In some embodiments, the present invention provides a method for the treatment or prevention of an autophagy-related disease, disorder, or condition, in a subject in need thereof, comprising administering RTB101 in an amount of about 100 mg/week to about 500 mg/week, about 150 mg/week to about 450 mg/week, about 200 mg/week to about 400 mg/week, about 250 mg/week to about 350 mg/week, about 275 mg/week to about 325 mg/week, about 280 mg/week to about 320 mg/week, about 285 mg/week to about 315 mg/week, about 290 mg/week to about 310 mg/week, or about 295 mg/week to about 305 mg/week. In some such embodiments, a provided method further comprises administration of everolimus or sirolimus in any amount described above and herein.

In some embodiments, the present invention provides a method for the treatment or prevention of an autophagy-related disease, disorder, or condition, in a subject in need thereof, comprising administering RTB101 in an amount of about 200 mg/week, about 210 mg/week, about 220 mg/week, about 230 mg/week, about 240 mg/week, about 250 mg/week, about 260 mg/week, about 270 mg/week, about 280 mg/week, about 290 mg/week, about 300 mg/week, about 310 mg/week, about 320 mg/week, about 330 mg/week, about 340 mg/week, about 350 mg/week, about 360 mg/week, about 370 mg/week, about 380 mg/week, about 390 mg/week, or about 400 mg/week. In some such embodiments, a provided method further comprises administration of everolimus or sirolimus in any amount described above and herein.

In some embodiments, the present invention provides a method for the treatment or prevention of an autophagy-related disease, disorder, or condition, in a subject in need thereof, comprising administering RTB101 in an amount of about 300 mg/week. In some such embodiments, a provided method further comprises administration of sirolimus in an amount described above and herein. For instance, in some embodiments a provided method comprises administering RTB101 in an amount of about 300 mg/week and everolimus or sirolimus in an amount of about two mg/week to about six mg/week.

In some embodiments, RTB101 is administered in any amount contemplated herein in one or more unit dosage forms. In some embodiments, RTB101 is administered in one unit dose. In some embodiments, RTB101 is administered in two unit doses. In some embodiments, RTB101 is administered in three unit doses. For example, in some embodiments a provided method comprises administering RTB101 in an amount of about 300 mg/week in three unit doses.

In some embodiments, the present invention provides a method for the treatment or prevention of an autophagy-related disease, disorder, or condition, in a subject in need thereof, comprising administering everolimus or sirolimus in an amount of about 0.5 mg/week to about 8 mg/week, about 1 mg/week to about 7 mg/week, about 1.5 mg/week to about 6.5 mg/week, or about 2 mg/week to about 6 mg/week. In some such embodiments, a provided method further comprises administration of RTB101 in any amount described above and herein.

In some embodiments, the present invention provides a method for the treatment or prevention of an autophagy-related disease, disorder, or condition, in a subject in need thereof, comprising administering everolimus or sirolimus in an amount of about 0.5 mg/week, about 1 mg/week, about 1.5 mg/week, about 2 mg/week, about 2.5 mg/week, about 3 mg/week, about 3.5 mg/week, about 4 mg/week, about 4.5 mg/week, about 5 mg/week, about 5.5 mg/week, about 6 mg/week, about 6.5 mg/week, about 7 mg/week, about 7.5 mg/week, or about 8 mg/week. In some such embodiments, a provided method further comprises administration of RTB101 in any amount described above and herein.

In some embodiments, the present invention provides a method for the treatment or prevention of an autophagy-related disease, disorder, or condition, in a subject in need thereof, comprising administering everolimus or sirolimus in an amount of about 2 mg/week, about 4 mg/week, or about 6 mg/week. In some such embodiments, a provided method further comprises administration of RTB101 in an amount described above and herein. For instance, in some embodiments a provided method comprises administering everolimus or sirolimus in an amount of about 2 mg/week to about 6 mg/week and RTB101 in an amount of about 300mg/week.

In some embodiments, everolimus or sirolimus is administered in any amount contemplated herein in one or more unit dosage forms. In some embodiments, everolimus or sirolimus is administered in one unit dose. In some embodiments, everolimus or sirolimus is administered in two unit doses. In some embodiments, everolimus or sirolimus is administered in three unit doses. For example, in some embodiments a provided method comprises administering everolimus or sirolimus in an amount of about 2 mg/week in one unit dose, about 4 mg/week in two unit doses, or 6 mg/week in three unit doses.

In some embodiments, RTB101 is administered orally once weekly to a patient in need thereof for at least about twelve weeks. In some embodiments, RTB101 is administered orally once weekly for at least about one week, at least about two weeks, at least about three weeks, at least about four weeks, at least about five weeks, at least about six weeks, at least about seven weeks, at least about eight weeks, at least about nine weeks, at least about ten weeks, at least about eleven weeks, or at least about twelve weeks.

In some embodiments, RTB101 is administered orally once weekly to a patient in need thereof for up to about twelve weeks. In some embodiments, RTB101 is administered orally once weekly for about one week, about two weeks, about three weeks, about four weeks, about five weeks about six weeks, about seven weeks, about eight weeks, about nine weeks, about ten weeks, about eleven weeks, or about twelve weeks. In some embodiments, RTB101 is administered orally once weekly to a patient in need thereof for at least twelve weeks. In some embodiments, RTB101 is administered orally once weekly to a patient in need thereof for the duration of the patient's life.

In some embodiments, everolimus or sirolimus is administered orally once weekly to a patient in need thereof for at least about twelve weeks. In some embodiments, everolimus or sirolimus is administered orally once weekly for at least about one week, at least about two weeks, at least about three weeks, at least about four weeks, at least about five weeks, at least about six weeks, at least about seven weeks, at least about eight weeks, at least about nine weeks, at least about ten weeks, at least about eleven weeks, or at least about twelve weeks.

In some embodiments, everolimus or sirolimus is administered orally once weekly to a patient in need thereof for up to about twelve weeks. In some embodiments, everolimus or sirolimus is administered orally once weekly for about one week, about two weeks, about three weeks, about four weeks, about five weeks about six weeks, about seven weeks, about eight weeks, about nine weeks, about ten weeks, about eleven weeks, or about twelve weeks. In some embodiments, RAD101 is administered orally once weekly to a patient in need thereof for at least twelve weeks. In some embodiments, RAD101 is administered orally once weekly to a patient in need thereof for the duration of the patient's life.

In some embodiments, RTB101 and everolimus or sirolimus are co-administered orally once weekly to a patient in need thereof for up to about twelve weeks. In some embodiments, RTB101 and everolimus or sirolimus are administered orally once weekly for about one week, about two weeks, about three weeks, about four weeks, about five weeks about six weeks, about seven weeks, about eight weeks, about nine weeks, about ten weeks, about eleven weeks, or about twelve weeks. In some embodiments, RTB101 and everolimus or sirolimus are co-administered orally once weekly to a patient in need thereof for at least twelve weeks. In some embodiments, RTB101 and everolimus or sirolimus are co-administered orally once weekly to a patient in need thereof for the duration of the patient's life.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of about 1.5 mg/kg/day and the RTB101 is administered at a dose of about 2.5 mg/kg/day.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein: the everolimus or sirolimus is administered at a dose of between about 1.4 and 1.6 mg/kg/day and the RTB101 is administered at a dose of between 2.4 and 2.6 mg/kg/day; the everolimus or sirolimus is administered at a dose of between about 1.3 and 1.7 mg/kg/day and the RTB101 is administered at a dose of between about 2.3 and 2.7 mg/kg/day; the everolimus or sirolimus is administered at a dose of between about 1.2 and 1.8 mg/kg/day and the RTB101 is administered at a dose of between about 2.2 and 2.8 mg/kg/day; the everolimus or sirolimus is administered at a dose of between about 1.1 and 1.9 mg/kg/day and the RTB101 is administered at a dose of between about 2.1 and 2.9 mg/kg/day; the everolimus or sirolimus is administered at a dose of between about 1.0 and 2.0 mg/kg/day and the RTB101 is administered at a dose of between about 2.0 and 3.0 mg/kg/day; the everolimus or sirolimus is administered at a dose of between about 0.8 and 2.2 mg/kg/day and the RTB101 is administered at a dose of between about 1.8 and 2.6 mg/kg/day; the everolimus or sirolimus is administered at a dose of between about 0.6 and 2.4 mg/kg/day and the RTB101 is administered at a dose of between about 1.6 and 2.8 mg/kg/day; the everolimus or sirolimus is administered at a dose of between about 0.4 and 2.6 mg/kg/day and the RTB101 is administered at a dose of between about 1.4 and 3.0 mg/kg/day; the everolimus or sirolimus is administered at a dose of between about 0.2 and 2.8 mg/kg/day and the RTB101 is administered at a dose of between about 1.0 and 3.5 mg/kg/day; the everolimus or sirolimus is administered at a dose of between about 0.01 and 3.0 mg/kg/day and the RTB101 is administered at a dose of between about 0.5 and 4.0 mg/kg/day; the everolimus or sirolimus is administered at a dose of between about 0.01 and 5.0 mg/kg/day and the RTB101 is administered at a dose of between about 0.01 and 5.0 mg/kg/day; the everolimus or sirolimus is administered at a dose of between about 0.01 and 5.0 mg/kg/day and the RTB101 is administered at a dose of between about 0.01 and 10.0 mg/kg/day; the everolimus or sirolimus is administered at a dose of between about 0.01 and 5.0 mg/kg/day and the RTB101 is administered at a dose of between about 0.01 and 15.0 mg/kg/day; the everolimus or sirolimus is administered at a dose of between about 0.01 and 5.0 mg/kg/day and the RTB101 is administered at a dose of between about 0.01 and 20.0 mg/kg/day; the everolimus or sirolimus is administered at a dose of between about 0.01 and 5.0 mg/kg/day and the RTB101 is administered at a dose of between about 0.01 and 30.0 mg/kg/day; or the everolimus or sirolimus is administered at a dose of between about 0.01 and 10.0 mg/kg/day and the RTB101 is administered at a dose of between about 0.01 and 40.0 mg/kg/day.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of between about 0.01 and 10.0 mg/kg/day and the RTB101 is administered at a dose of between about 0.01 and 40.0 mg/kg/day.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of about 1.5 mg/kg/week and the RTB101 is administered at a dose of about 2.5 mg/kg/week.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein: the everolimus or sirolimus is administered at a dose of between about 1.4 and 1.6 mg/kg/week and the RTB101 is administered at a dose of between 2.4 and 2.6 mg/kg/week; the everolimus or sirolimus is administered at a dose of between about 1.3 and 1.7 mg/kg/week and the RTB101 is administered at a dose of between about 2.3 and 2.7 mg/kg/week; the everolimus or sirolimus is administered at a dose of between about 1.2 and 1.8 mg/kg/week and the RTB101 is administered at a dose of between about 2.2 and 2.8 mg/kg/week; the everolimus or sirolimus is administered at a dose of between about 1.1 and 1.9 mg/kg/week and the RTB101 is administered at a dose of between about 2.1 and 2.9 mg/kg/week; the everolimus or sirolimus is administered at a dose of between about 1.0 and 2.0 mg/kg/week and the RTB101 is administered at a dose of between about 2.0 and 3.0 mg/kg/week; the everolimus or sirolimus is administered at a dose of between about 0.8 and 2.2 mg/kg/week and the RTB101 is administered at a dose of between about 1.8 and 2.6 mg/kg/week; the everolimus or sirolimus is administered at a dose of between about 0.6 and 2.4 mg/kg/week and the RTB101 is administered at a dose of between about 1.6 and 2.8 mg/kg/week; the everolimus or sirolimus is administered at a dose of between about 0.4 and 2.6 mg/kg/week and the RTB101 is administered at a dose of between about 1.4 and 3.0 mg/kg/week; the everolimus or sirolimus is administered at a dose of between about 0.2 and 2.8 mg/kg/week and the RTB101 is administered at a dose of between about 1.0 and 3.5 mg/kg/day; the everolimus or sirolimus is administered at a dose of between about 0.01 and 3.0 mg/kg/week and the RTB101 is administered at a dose of between about 0.5 and 4.0 mg/kg/week; the everolimus or sirolimus is administered at a dose of between about 0.01 and 5.0 mg/kg/week and the RTB101 is administered at a dose of between about 0.01 and 5.0 mg/kg/week; the everolimus or sirolimus is administered at a dose of between about 0.01 and 5.0 mg/kg/week and the RTB101 is administered at a dose of between about 0.01 and 10.0 mg/kg/week; the everolimus or sirolimus is administered at a dose of between about 0.01 and 5.0 mg/kg/week and the RTB101 is administered at a dose of between about 0.01 and 15.0 mg/kg/week; the everolimus or sirolimus is administered at a dose of between about 0.01 and 5.0 mg/kg/week and the RTB101 is administered at a dose of between about 0.01 and 20.0 mg/kg/week; the everolimus or sirolimus is administered at a dose of between about 0.01 and 5.0 mg/kg/week and the RTB101 is administered at a dose of between about 0.01 and 30.0 mg/kg/week; or the everolimus or sirolimus is administered at a dose of between about 0.01 and 10.0 mg/kg/week and the RTB101 is administered at a dose of between about 0.01 and 40.0 mg/kg/week.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of between about 0.01 and 10.0 mg/kg/week and the RTB101 is administered at a dose of between about 0.01 and 40.0 mg/kg/week.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of about 1.5 mg/kg/week and the RTB101 is administered at a dose of about 2.5 mg/kg/day.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein: the everolimus or sirolimus is administered at a dose of between about 1.4 and 1.6 mg/kg/week and the RTB101 is administered at a dose of between 2.4 and 2.6 mg/kg/day; the everolimus or sirolimus is administered at a dose of between about 1.3 and 1.7 mg/kg/week and the RTB101 is administered at a dose of between about 2.3 and 2.7 mg/kg/day; the everolimus or sirolimus is administered at a dose of between about 1.2 and 1.8 mg/kg/week and the RTB101 is administered at a dose of between about 2.2 and 2.8 mg/kg/day; the everolimus or sirolimus is administered at a dose of between about 1.1 and 1.9 mg/kg/week and the RTB101 is administered at a dose of between about 2.1 and 2.9 mg/kg/day; the everolimus or sirolimus is administered at a dose of between about 1.0 and 2.0 mg/kg/week and the RTB101 is administered at a dose of between about 2.0 and 3.0 mg/kg/day; the everolimus or sirolimus is administered at a dose of between about 0.8 and 2.2 mg/kg/week and the RTB101 is administered at a dose of between about 1.8 and 2.6 mg/kg/day; the everolimus or sirolimus is administered at a dose of between about 0.6 and 2.4 mg/kg/week and the RTB101 is administered at a dose of between about 1.6 and 2.8 mg/kg/day; the everolimus or sirolimus is administered at a dose of between about 0.4 and 2.6 mg/kg/week and the RTB101 is administered at a dose of between about 1.4 and 3.0 mg/kg/day; the everolimus or sirolimus is administered at a dose of between about 0.2 and 2.8 mg/kg/week and the RTB101 is administered at a dose of between about 1.0 and 3.5 mg/kg/day; the everolimus or sirolimus is administered at a dose of between about 0.01 and 3.0 mg/kg/week and the RTB101 is administered at a dose of between about 0.5 and 4.0 mg/kg/day; the everolimus or sirolimus is administered at a dose of between about 0.01 and 5.0 mg/kg/week and the RTB101 is administered at a dose of between about 0.01 and 5.0 mg/kg/day; the everolimus or sirolimus is administered at a dose of between about 0.01 and 5.0 mg/kg/week and the RTB101 is administered at a dose of between about 0.01 and 10.0 mg/kg/day; the everolimus or sirolimus is administered at a dose of between about 0.01 and 5.0 mg/kg/week and the RTB101 is administered at a dose of between about 0.01 and 15.0 mg/kg/day; the everolimus or sirolimus is administered at a dose of between about 0.01 and 5.0 mg/kg/week and the RTB101 is administered at a dose of between about 0.01 and 20.0 mg/kg/day; the everolimus or sirolimus is administered at a dose of between about 0.01 and 5.0 mg/kg/week and the RTB101 is administered at a dose of between about 0.01 and 30.0 mg/kg/day; or the everolimus or sirolimus is administered at a dose of between about 0.01 and 10.0 mg/kg/week and the RTB101 is administered at a dose of between about 0.01 and 40.0 mg/kg/day.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of between about 0.01 and 10.0 mg/kg/week and the RTB101 is administered at a dose of between about 0.01 and 40.0 mg/kg/day.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of about 1.5 mg/kg/day and the RTB101 is administered at a dose of about 2.5 mg/kg/week.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein: the everolimus or sirolimus is administered at a dose of between about 1.4 and 1.6 mg/kg/day and the RTB101 is administered at a dose of between 2.4 and 2.6 mg/kg/week; the everolimus or sirolimus is administered at a dose of between about 1.3 and 1.7 mg/kg/day and the RTB101 is administered at a dose of between about 2.3 and 2.7 mg/kg/week; the everolimus or sirolimus is administered at a dose of between about 1.2 and 1.8 mg/kg/day and the RTB101 is administered at a dose of between about 2.2 and 2.8 mg/kg/week; the everolimus or sirolimus is administered at a dose of between about 1.1 and 1.9 mg/kg/day and the RTB101 is administered at a dose of between about 2.1 and 2.9 mg/kg/week; the everolimus or sirolimus is administered at a dose of between about 1.0 and 2.0 mg/kg/day and the RTB101 is administered at a dose of between about 2.0 and 3.0 mg/kg/week; the everolimus or sirolimus is administered at a dose of between about 0.8 and 2.2 mg/kg/day and the RTB101 is administered at a dose of between about 1.8 and 2.6 mg/kg/week; the everolimus or sirolimus is administered at a dose of between about 0.6 and 2.4 mg/kg/day and the RTB101 is administered at a dose of between about 1.6 and 2.8 mg/kg/week; the everolimus or sirolimus is administered at a dose of between about 0.4 and 2.6 mg/kg/day and the RTB101 is administered at a dose of between about 1.4 and 3.0 mg/kg/week; the everolimus or sirolimus is administered at a dose of between about 0.2 and 2.8 mg/kg/day and the RTB101 is administered at a dose of between about 1.0 and 3.5 mg/kg/week; the everolimus or sirolimus is administered at a dose of between about 0.01 and 3.0 mg/kg/day and the RTB101 is administered at a dose of between about 0.5 and 4.0 mg/kg/week; the everolimus or sirolimus is administered at a dose of between about 0.01 and 5.0 mg/kg/day and the RTB101 is administered at a dose of between about 0.01 and 5.0 mg/kg/week; the everolimus or sirolimus is administered at a dose of between about 0.01 and 5.0 mg/kg/day and the RTB101 is administered at a dose of between about 0.01 and 10.0 mg/kg/week; the everolimus or sirolimus is administered at a dose of between about 0.01 and 5.0 mg/kg/day and the RTB101 is administered at a dose of between about 0.01 and 15.0 mg/kg/week; the everolimus or sirolimus is administered at a dose of between about 0.01 and 5.0 mg/kg/day and the RTB101 is administered at a dose of between about 0.01 and 20.0 mg/kg/week; the everolimus or sirolimus is administered at a dose of between about 0.01 and 5.0 mg/kg/day and the RTB101 is administered at a dose of between about 0.01 and 30.0 mg/kg/week; or the everolimus or sirolimus is administered at a dose of between about 0.01 and 10.0 mg/kg/day and the RTB101 is administered at a dose of between about 0.01 and 40.0 mg/kg/week.

In some embodiments, the present invention provides a method for the treatment or prevention of a disease, disorder, or condition associated with alpha-1 antitrypsin deficiency, in a subject in need thereof, comprising administering to the subject an effective amount of a combination of everolimus or sirolimus and RTB101 wherein the everolimus or sirolimus is administered at a dose of between about 0.01 and 10.0 mg/kg/day and the RTB101 is administered at a dose of between about 0.01 and 40.0 mg/kg/week.

In some embodiments, the present invention provides a method for the treatment or prevention of a disease, disorder, or condition associated with alpha-1 antitrypsin deficiency, and the everolimus or sirolimus is administered at a dose of about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0 mg/kg/day.

In some embodiments, the present invention provides a method for the treatment or prevention of a disease, disorder, or condition associated with alpha-1 antitrypsin deficiency, and RTB101 is administered at a dose of about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, or 25.0 mg/kg/day.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor is administered weekly and the catalytic mTOR inhibitor is administered daily.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor is administered daily and the catalytic mTOR inhibitor is administered weekly.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor and the catalytic mTOR inhibitor are administered weekly.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor is administered biweekly and the catalytic mTOR inhibitor is administered daily.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor is administered daily and the catalytic mTOR inhibitor is administered biweekly.

In some embodiments, the present invention provides a method for the treatment or prevention of Parkinson's disease or a disease, disorder, or condition associated with alpha-1 antitrypsin deficiency, in a subject in need thereof, comprising administering to the subject an effective amount of a combination of an allosteric mTOR inhibitor and a catalytic mTOR inhibitor wherein the allosteric mTOR inhibitor and the catalytic mTOR inhibitor are administered biweekly.

In some embodiments, a provided method is any of those described above and herein, wherein the disease is Parkinson's disease. In some embodiments, a provided method is any of those described above and herein, wherein the disease is GBA-related Parkinson's disease. In some such embodiments, the allosteric mTOR inhibitor is everolimus. In some such embodiments, the allosteric mTOR inhibitor is sirolimus. In some such embodiments, the catalytic mTOR inhibitor is RTB101.

In some embodiments, a provided method comprises steps of administering to a subject suffering from or susceptible to Parkinson's disease an effective amount of a combination of an allosteric mTOR inhibitor and a catalytic mTOR inhibitor, such that the severity or incidence of one or more symptoms of Parkinson's disease is reduced, or its onset is delayed. In some such embodiments, the allosteric mTOR inhibitor is everolimus. In some such embodiments, the allosteric mTOR inhibitor is sirolimus. In some such embodiments, the catalytic mTOR inhibitor is RTB101. In some embodiments, the subject suffering from or susceptible to Parkinson's disease has a GBA mutation correlated with higher risk of developing Parkinson's disease.

In some embodiments, the Parkinson's disease is characterized by the presence of certain types of abnormal aggregates, for instance Lewy Bodies. Without wishing to be bound by any particular theory, use of a provided combination of an allosteric mTOR inhibitor and a catalytic mTOR inhibitor may reduce or delay the formation of such aggregates by, for instance, inducing or augmenting autophagy.

In some embodiments, the present invention provides a method for the treatment or prevention of Parkinson's disease in a patient in need thereof, wherein the patient is genotypically screened for the presence of a particular allele and/or mutation prior to treatment.

In some embodiments, the patient is genotypically screened for mutant LRKK2-related Parkinson's disease.

In some embodiments, the patient is genotypically screened for the mutant GBA-related Parkinson's disease.

In some embodiments, a provided method is any of those described above and herein, wherein the disease is a disease, disorder, or condition associated with alpha-1 antitrypsin deficiency. In some such embodiments, the allosteric mTOR inhibitor is everolimus. In some such embodiments, the allosteric mTOR inhibitor is sirolimus. In some such embodiments, the catalytic mTOR inhibitor is RTB101. In some such embodiments, the disease is a disease of the lung. In some such embodiments, the disease is a disease of the liver. In some embodiments, the disease is selected from chronic obstructive pulmonary disease, emphysema, asthma, cirrhosis, hepatitis, hepatomegaly, jaundice, and liver failure.

In some embodiments, a provided method comprises steps of administering to a subject suffering from or susceptible to the disease, disorder, or condition associated with alpha-1 antitrypsin deficiency an effective amount of a combination of an allosteric mTOR inhibitor and a catalytic mTOR inhibitor, such that the severity or incidence of one or more symptoms of the disease, disorder, or condition associated with alpha-1 antitrypsin deficiency is reduced, or its onset is delayed. In some such embodiments, the allosteric mTOR inhibitor is everolimus. In some such embodiments, the allosteric mTOR inhibitor is sirolimus. In some such embodiments, the catalytic mTOR inhibitor is RTB101.

In some embodiments, the present invention provides a method for the treatment or prevention of a disease, disorder, or condition associated with alpha-1 antitrypsin deficiency in a patient in need thereof, wherein the patient is genotypically screened for the presence of a particular allele and/or mutation prior to treatment.

In some embodiments, the patient is genotypically screened for the presence of a Z allele prior to treatment.

In some embodiments, the patient is genotypically screened for the presence of the PiZZ mutation prior to treatment.

In some embodiments, the present invention provides a combination of an allosteric mTOR inhibitor and a catalytic mTOR inhibitor for use in the treatment or prevention of Parkinson's disease or a disease, disorder, or condition associated with alpha-1 antitrypsin deficiency according to any of the methods described above and herein.

In some embodiments, the present invention provides an allosteric mTOR inhibitor and a catalytic mTOR inhibitor for use in the manufacture of a medicament for the treatment or prevention of Parkinson's disease or a disease, disorder, or condition associated with alpha-1 antitrypsin deficiency according to any of the methods described above and herein.

Provided Combination Products

In some embodiments, the present invention provides a combination product comprising an allosteric mTOR inhibitor and a catalytic mTOR inhibitor for simultaneous, separate and/or sequential administration for use in the treatment or prevention of an autophagy-related disease, disorder, or condition.

In some embodiments, the present invention provides a combination product comprising an allosteric mTOR inhibitor and a catalytic mTOR inhibitor for simultaneous, separate and/or sequential administration for use in the treatment or prevention of Parkinson's disease or a disease, disorder, or condition associated with alpha-1 antitrypsin deficiency.

In some embodiments, the present invention provides a combination product comprising an allosteric mTOR inhibitor and a catalytic mTOR inhibitor for simultaneous, separate and/or sequential administration for use in the treatment or prevention of Parkinson's disease or a disease, disorder, or condition associated with alpha-1 antitrypsin deficiency, wherein the allosteric mTOR inhibitor is selected from everolimus, sirolimus, temsirolimus, zotarolimus, umirolimus, and deforolimus; and the catalytic mTOR inhibitor is selected from RTB101, CCG168, Ku-0063794, WYE-354, and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In some embodiments, the present invention provides a combination product comprising everolimus or sirolimus and RTB101 for simultaneous, separate and/or sequential administration for use in the treatment or prevention of Parkinson's disease or a disease, disorder, or condition associated with alpha-1 antitrypsin deficiency.

In some such embodiments, the allosteric mTOR inhibitor and the catalytic mTOR inhibitor is any of those described above and herein.

In some such embodiments, the allosteric mTOR inhibitor and the catalytic mTOR inhibitor are each present in an amount as described above and herein.

In some such embodiments, the allosteric mTOR inhibitor is everolimus or sirolimus.

In some such embodiments, the allosteric mTOR inhibitor is everolimus.

In some such embodiments, the allosteric mTOR inhibitor is sirolimus.

In some such embodiments, the catalytic mTOR inhibitor is RTB101.

Pharmaceutical Compositions

In some embodiments, a pharmaceutical composition comprises: an allosteric mTOR inhibitor; a catalytic mTOR inhibitor; and a pharmaceutically acceptable carrier or diluent, for use in the treatment or prevention of an autophagy-related disease, disorder, or condition.

In some embodiments, a pharmaceutical composition comprises: an allosteric mTOR inhibitor; a catalytic mTOR inhibitor; and a pharmaceutically acceptable carrier or diluent, for use in the treatment or prevention of Parkinson's disease or a disease, disorder, or condition associated with alpha-1 antitrypsin deficiency.

In some embodiments, a pharmaceutical composition comprises: an allosteric mTOR inhibitor selected from everolimus, sirolimus, temsirolimus, zotarolimus, umirolimus, and deforolimus; a catalytic mTOR inhibitor selected from RTB101, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one; and a pharmaceutically acceptable carrier or diluent, for use in the treatment or prevention of Parkinson's disease or a disease, disorder, or condition associated with alpha-1 antitrypsin deficiency.

In some embodiments, a pharmaceutical composition comprises: everolimus or sirolimus; RTB101; and a pharmaceutically acceptable carrier or diluent, for use in the treatment or prevention of Parkinson's disease or a disease, disorder, or condition associated with alpha-1 antitrypsin deficiency.

In some embodiments, a pharmaceutical composition comprises: about 25 mg everolimus or sirolimus; about 250 mg RTB101; and a pharmaceutically acceptable carrier or diluent, for use in the treatment or prevention of Parkinson's disease.

In some embodiments, a pharmaceutical composition comprises: about 22.5 to 27.5 mg everolimus or sirolimus; about 240 to 260 mg RTB101; and a pharmaceutically acceptable carrier or diluent, for use in the treatment or prevention of Parkinson's disease.

In some embodiments, a pharmaceutical composition comprises: about 20 to 30 mg everolimus or sirolimus; about 230 to 270 mg RTB101; and a pharmaceutically acceptable carrier or diluent, for use in the treatment or prevention of Parkinson's disease.

In some embodiments, a pharmaceutical composition comprises: about 17.5 to 32.5 mg everolimus or sirolimus; about 220 to 280 mg RTB101; and a pharmaceutically acceptable carrier or diluent, for use in the treatment or prevention of Parkinson's disease.

In some embodiments, a pharmaceutical composition comprises: about 15 to 35 mg everolimus or sirolimus; about 210 to 290 mg RTB101; and a pharmaceutically acceptable carrier or diluent, for use in the treatment or prevention of Parkinson's disease.

In some embodiments, a pharmaceutical composition comprises: about 12.5 to 37.5 mg everolimus or sirolimus; about 200 to 300 mg RTB101; and a pharmaceutically acceptable carrier or diluent, for use in the treatment or prevention of Parkinson's disease.

In some embodiments, a pharmaceutical composition comprises: about 10 to 40 mg everolimus or sirolimus; about 150 to 325 mg RTB101; and a pharmaceutically acceptable carrier or diluent, for use in the treatment or prevention of Parkinson's disease.

In some embodiments, a pharmaceutical composition comprises: about 7.5 to 42.5 mg everolimus or sirolimus; about 100 to 350 mg RTB101; and a pharmaceutically acceptable carrier or diluent, for use in the treatment or prevention of Parkinson's disease.

In some embodiments, a pharmaceutical composition comprises: about 5 to 45 mg everolimus or sirolimus; about 50 to 400 mg RTB101; and a pharmaceutically acceptable carrier or diluent, for use in the treatment or prevention of Parkinson's disease.

In some embodiments, a pharmaceutical composition comprises: about 1 to 50 mg everolimus or sirolimus; about 1 to 500 mg RTB101; and a pharmaceutically acceptable carrier or diluent, for use in the treatment or prevention of Parkinson's disease.

In some embodiments, a pharmaceutical composition comprises: about 1 to 50 mg everolimus or sirolimus; about 1 to 800 mg RTB101; and a pharmaceutically acceptable carrier or diluent, for use in the treatment or prevention of Parkinson's disease.

In some embodiments, a pharmaceutical composition comprises: about 1 mg everolimus or sirolimus; about 10 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.9 to 1.1 mg everolimus or sirolimus; about 7.5 to 12.5 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.8 to 1.2 mg everolimus or sirolimus; about 5 to 15 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.7 to 1.3 mg everolimus or sirolimus; about 2.5 to 17.5 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.6 to 1.4 mg everolimus or sirolimus; about 0.1 to 20 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.5 to 1.5 mg everolimus or sirolimus; about 0.1 to 25 mg RTB101; and a pharmaceutically acceptable carrier or diluent, for use in the treatment or prevention of Parkinson's disease or a disease, disorder, or condition associated with alpha-1 antitrypsin deficiency.

In some embodiments, a pharmaceutical composition comprises: about 0.1 to 2.0 mg everolimus or sirolimus; about 0.1 to 30 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.05 to 2.5 mg everolimus or sirolimus; about 0.1 to 40 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.01 to 3 mg everolimus or sirolimus; about 0.1 to 50 mg RTB101; and a pharmaceutically acceptable carrier or diluent, for use in the treatment or prevention of a disease, disorder, or condition associated with alpha-1 antitrypsin deficiency.

In some embodiments, a pharmaceutical composition comprises: about 0.01 to 5 mg everolimus or sirolimus; about 0.1 to 50 mg RTB101; and a pharmaceutically acceptable carrier or diluent, for use in the treatment or prevention of a disease, disorder, or condition associated with alpha-1 antitrypsin deficiency.

In some embodiments of the present invention, a pharmaceutical composition as described above and herein comprising an allosteric mTOR inhibitor and a catalytic mTOR inhibitor are administered orally.

One of skill in the medical arts will appreciate that pharmaceutical compositions described above and herein are contemplated for use in any of the provided methods described above and herein.

Compounds and Definitions:

As used herein, the term "a," "an," "the" and similar terms used in the context of the present invention (especially in the context of the claims) are to be construed to cover both the singular and plural unless otherwise indicated herein or clearly contradicted by the context.

As used herein, the term "about" in connection with a particular drug dose shall have the meaning of a drug dose in the range of plus/minus 10%, preferably plus/minus 5%, more preferably plus/minus 2.5%, or more preferably still plus/minus 1%, of the nominal drug dose. By way of example, a nominal drug dose of about 100 mg active ingredient may contain from 90 to 110 mg, preferably from 95 to 105 mg, more preferably 97.5 to 102.5 mg, or more preferably still 99 to 101 mg active ingredient per dose.

The term "mTOR" (mammalian target of rapamycin), also known as mechanistic target of rapamycin and FK506 binding protein 12-rapamycin associated protein 1 (FRAP 1), refers to a serine/threonine protein kinase that regulates cell growth, cell proliferation, cell motility, cell survival, protein synthesis, and transcription. mTOR integrates the input from upstream pathways, including insulin, growth factors (such as IGF-1 and IGF-2), and mitogens. mTOR also senses cellular nutrient and energy levels and redox status. The mTOR pathway is dysregulated in human diseases, especially certain cancers. Decreased TOR activity has been found to slow aging in *S. cerevisiae, C. elegans*, and *D. melanogaster*. The mTOR inhibitor rapamycin has been confirmed to increase lifespan in mice. It has been hypothesized that dietary regimes such as caloric restriction and methionine restriction cause lifespan extension by decreasing mTOR activity. mTOR inhibitors are in use for the treatment of transplant rejection, cancer, and restenosis. mTOR inhibitors may also be useful for treating age-associated diseases.

The term "mTOR-mediated" refers to a disease, disorder, or condition that is characterized by abnormal mTOR activity or mTOR activity that, when modulated, leads to the amelioration of other abnormal biological processes. An mTOR-mediated disorder, disorder, or condition may be completely or partially mediated by modulating mTOR. In particular, an mTOR-mediated disorder, disorder, or condition is one in which inhibition of mTOR results in some effect on the underlying disorder, disorder, or condition e.g., administration of an mTOR inhibitor results in some improvement in at least some of the subjects being treated.

The term "autophagy-related" refers to a disease, disorder, or condition that is characterized by abnormal activity in a lysosomal degradation pathway or a disease, disorder, or condition in which modulation of autophagy leads to the amelioration of one of more symptoms and/or one or more abnormal biological processes associates with the disease, disorder, or condition. An autophagy-related disease, disorder, or condition may be completely or partially mediated by modulating autophagy.

The term "mTOR inhibitor" refers to the ability of a compound disclosed herein to alter the function of mTOR. An inhibitor may block or reduce the activity of mTOR by forming a reversible or irreversible covalent bond between the inhibitor and mTOR or through formation of a noncovalently bound complex. Such inhibition may be manifest only in particular cell types or may be contingent on a particular biological event. The term "inhibit" or "inhibition" also refers to altering the function of mTOR by decreasing the probability that a complex forms between mTOR and a natural substrate. In some embodiments, inhibition of mTOR may be assessed using the methods described in WO 1994/09010.

As used herein, the term "allosteric mTOR inhibitor" refers to a compound which targets, decreases or inhibits the activity/function of the mTOR kinase through binding to an allosteric binding site, for example the FKBP12-rapamycin binding site (FRB), of the mTORC1 complex. Examples of allosteric mTOR inhibitors include: O-substituted rapamycin analogs in which the hydroxyl group on the cyclohexyl ring of rapamycin is replaced by OR1 in which R1 is hydroxyalkyl, hydroxyalkoxyalkyl, acylaminoalkyl, or aminoalky (e.g., RAD001; everolimus) as described in U.S. Pat. No. 5,665,772 and WO94/09010, the contents of which are incorporated by reference; rapamycin analogs substituted at the 28- or 28-position; epimers of such rapamycin analogs as described in U.S. Pat. No. 6,015,815, WO95/14023 and WO99/15530 (e.g., zotarolimus; ABT578) or those described in U.S. Pat. No. 7,091,213, WO98/02441 and WO01/14387 (e.g., ridaforolimus/deforolimus/AP-23573/MK-8669) the contents of which are incorporated by reference; rapamycin analogs in which the hydroxyl group on the cyclohexyl ring of rapamycin and/or the hydroxy group at the 28 position is replaced with an hydroxyester group as described in U.S. RE44,768 (e.g., temsirolimus); rapamycin analogs wherein the methoxy group at the 16 position is replaced with another substituent such as, for example, alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group such as those analogs described in WO95/16691 and WO96/41807 the contents of which are incorporated by reference; rapamycin analogs wherein the hydroxy at the 40-position of rapamycin is alkylated and/or the 32-carbonyl is reduced; and rapamycin analogs as described in US 2005/0101624 (e.g., umirolimus) the contents of which are incorporated by reference. Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-

(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin. Examples of rapamycin suitable for use in the present invention from WO95/16691 include, but are not limited to, 16-demethoxy-16-(pent-2-ynyl)oxy-rapamycin, 16-demethoxy-16-(but-2-ynyl)oxy-rapamycin, 16-demethoxy-16-(propargyl)oxy-rapamycin, 16-demethoxy-16-(4-hydroxy-but-2-ynyl)oxy-rapamycin, 16-demethoxy-16-benzyloxy-40-O-(2-hydroxyethyl)-rapamycin, 16-demethoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin. Rapamycin analogs suitable for use in the present invention from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin. Reference to any particular allosteric mTOR inhibitor herein also comprises any pharmaceutically acceptable salts, stereoisomers, tautomers, solvates, hydrates and polymorphs thereof. Whether or not a particular substance is an allosteric inhibitor of mTOR can be assessed using standard enzyme kinetics analysis well known to those skilled in art, Childs et al., (1976), Fersth A. (1985) and Dixon M. (2000). Whether or not a particular substance functions as an allosteric inhibitor by binding to the FRB of the mTORC1 complex can be assessed using the Time-Resolved Fluorescence Resonance Energy Transfer (TR-FRET) assay described hereinafter.

As used herein, the term "catalytic mTOR inhibitor" refers to a compound which targets, decreases or inhibits the catalytic activity/function of mTOR by binding to its ATP binding site. The term "catalytic mTOR inhibitor" as used herein includes both dual catalytic PI3K/mTOR inhibitors and selective catalytic mTOR inhibitors. Examples of catalytic mTOR inhibitors include RTB101, 8-(6-methoxy-pyridin-3-yl)-3-methyl-1-(4-piperazin-1-yl-3-trifluoromethylphenyl)-1,3-dihydro-imidazo[4,5-c]quinolin-2-one (WO2006/122806), vistusertib (AZD2014; WO2009/153597); AZD8055 (WO2009/153597; XL388 (US2010/0305093); sapanisertib (MLN0128; INK128; WO2015/051043); DS3078; apitolisib (GDC0980; WO2008/070740); omipalisib (GSK-2126458; WO2008/14446); NVP-BGT226 (K. Y. Chang et al., Clin. Cancer Res. 17(22): 7116-26 (2011)); voxtalisib (XL765; SAR245409; WO2007044813); PF04691502 (WO2008032162); gedatolisib (PF05212384; PKI-587; WO2009/143313); SF1126 (WO2004/089925); GSK1059615 (WO2007/136940); BI-860585; OSI 027 (WO2007/061737); VS 5584 (WO2010/114484); CC-223 (WO2010/062571); DCBCI-0901 (Y. E. Lee et al., Mol. Canc. Thera. 12(11 Suppl): Abstract nr C270 (2013));); LY3023414 (WO2012/097039); P529 (WO2007/133249); panulisib (P7170; WO2012/007926); DS-7423 (T. Kashiyama et al., PLoS One 9(2): e87220 (2014)); PWT33567 mesylate (VCD-597; WO2010/110685); ME-344 (NV-128; P. Navarro et al., Cell Rep. 15(12):2705-18 (2016)); ABTL0812 (WO2010/106211); WYE-132; EXEL-3885 (Eur J Cancer Suppl. 6(12): Abst 322 (2008)); EXEL-4431 (Eur J Cancer Suppl. 6(12): Abst 322 (2008)); AR-mTOR-26 (101st Annu Meet Am Assoc Cancer Res (AACR) (April 17-21, Washington, D.C.) 2010, Abst 4484); NV-128 (A. B. Alvero et al., Mol Cancer Ther. 10(8): 1385-93 (2011)); salinomycin (VS-507; P. B. Gupta, et al., Cell 138(4): 645-59 (2009)); BN-107; BN-108; WAY-600; WYE-687; WYE-354 (K. Yu et al., Cancer Res. 69(15): 6232-40 (2009)); Ku-063794 (J. M. Garcia-Martinez et al., Biochem. J. 421(1): 29-42 (2009)); torkinib (PP242; B. Apsel et al., Nat. Chem. Biol. 4(11): 691-99 (2008)); PP30; CZ415 (REF); INK1069; EXEL-2044; EXEL-7518; SB2158; SB2280; AR-mTOR-1 (E. M. Wallace et al., Mol. Canc. Thera. 8(12 Suppl): Abst. B267 (2009)). Reference to any particular catalytic mTOR inhibitor herein also comprises any pharmaceutically acceptable salts, stereoisomers, tautomers, solvates, hydrates and polymorphs thereof. Whether or not a particular substance is a catalytic inhibitor of mTOR can be assessed using standard enzyme kinetics analysis well known to those skilled in art, Childs et al., (1976), Fersth A. (1985) and Dixon M. (2000).

As used herein, the term "RTB101" also comprises any pharmaceutically acceptable salts, stereoisomers, tautomers, solvates, hydrates and polymorphs thereof. For example, in one embodiment of the present invention, the RTB101 is provided in its monotosylate salt form.

As used herein, the term "CCG168" also comprises any pharmaceutically acceptable salts, stereoisomers, tautomers, solvates, hydrates and polymorphs thereof.

As used herein, the term "combination" refers to any combination of an allosteric mTOR inhibitor and a catalytic mTOR inhibitor useful in the treatment or prevention of a neurodegenerative disease, for example Parkinson's disease. Any such combination may be administered simultaneously or sequentially. The term "combination" also includes "combination product".

As used herein, the term "combination product" refers to any product which comprises both an allosteric mTOR inhibitor and a catalytic mTOR inhibitor, for example a combined fixed dose pharmaceutical composition which comprises an allosteric mTOR inhibitor and a catalytic mTOR inhibitor as active ingredients, or a kit of parts which comprises individual or combined preparations of an allosteric mTOR inhibitor and a catalytic mTOR inhibitor in forms suitable for simultaneous, separate or sequential administration. A combined fixed dose pharmaceutical composition comprises both an allosteric mTOR inhibitor and a catalytic mTOR inhibitor in a single pharmaceutical composition, for example a single pill or tablet comprising everolimus and RTB101 or CCG168.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "mg/kg/day" refers to mg of compound per kg bodyweight of subject per day.

As used herein, the term "preparations of an allosteric mTOR inhibitor and a catalytic mTOR inhibitor" includes pharmaceutical compositions of an allosteric mTOR inhibitor and a catalytic mTOR inhibitor. The term "individual preparations of an allosteric mTOR inhibitor and a catalytic mTOR inhibitor" refers to separate preparations of an allosteric mTOR inhibitor and a catalytic mTOR inhibitor, whereas "a combined preparation of an allosteric mTOR inhibitor and a catalytic mTOR inhibitor" refers to a single preparation comprising both an allosteric mTOR inhibitor and a catalytic mTOR inhibitor, for example a combined fixed dose pharmaceutical composition which comprises both an allosteric mTOR inhibitor and a catalytic mTOR inhibitor, for example everolimus and RTB101 or CCG168 in a single pill or tablet.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, e.g., *Remington's Pharmaceutical Sciences*, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66(1): 1-19 (1977), incorporated herein by reference. Pharmaceutically acceptable salts of the compounds of this invention include those derived from suitable inorganic and organic acids and bases. Examples of pharmaceutically acceptable, nontoxic acid addition salts include salts of an amino group (or other basic group) formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate.

As used herein, the term "RAD001" (also known as everolimus) also comprises any pharmaceutically acceptable salts, stereoisomers, tautomers, solvates, hydrates and polymorphs thereof.

As used herein, the term "RTB101" (also known as BEZ235 and dactolisib) also comprises any pharmaceutically acceptable salts, stereoisomers, tautomers, solvates, hydrates and polymorphs thereof.

As used herein, the term "sirolimus" also comprises any pharmaceutically acceptable salts, stereoisomers, tautomers, solvates, hydrates and polymorphs thereof.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In some embodiments, the subject is a human.

As used herein, a subject is "in need of" a treatment if such subject would benefit biologically, medically or in quality of life from such treatment.

As used herein, an individual who is "suffering from" a disease, disorder, or condition has been diagnosed with or displays one or more symptoms of a disease, disorder, or condition.

As used herein, an individual who is "susceptible to" a disease, disorder, or condition is one who has a higher risk of developing the disease, disorder, or condition than does a member of the general public. In some embodiments, an individual who is susceptible to a disease, disorder or condition may not have been diagnosed with the disease, disorder, or condition. In some embodiments, an individual who is susceptible to a disease, disorder, or condition may exhibit symptoms of the disease, disorder, or condition. In some embodiments, an individual who is susceptible to a disease, disorder, or condition may not exhibit symptoms of the disease, disorder, or condition. In some embodiments, an individual who is susceptible to a disease, disorder, or condition will develop the disease, disorder, or condition. In some embodiments, an individual who is susceptible to a disease, disorder, or condition will not develop the disease, disorder, or condition.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

As used herein, the term "treat", "treating" or "treatment" of any disease or disorder refers in some embodiment, to ameliorating the disease or disorder (i.e., slowing or arresting or reducing the development of the disease or at least one of the clinical symptoms thereof) in a subject by administration of a combination according to the present invention. In another embodiment "treat", "treating" or "treatment"

refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevention" of any particular disease or disorder refers to the administration of a compound of the invention to a subject before any symptoms of that disease or disorder are apparent.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

The compounds of the combinations of the present invention may be administered either simultaneously or sequentially. The compounds of the combinations of the present invention may also be administered separately, by the same or different route of administration, or together in the same pharmaceutical composition.

A kit of parts of the present invention comprises means for separately retaining individual or combined preparations of an allosteric mTOR inhibitor and a catalytic mTOR inhibitor, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

The allosteric mTOR inhibitor and catalytic mTOR inhibitor of the combinations of the invention may be brought together into a combination therapy: (i) prior to release of the combination product to physicians (e.g., in the case of a kit); (ii) by the physician themselves (or under the guidance of the physician) shortly before administration; or (iii) in the patient themselves, e.g., during sequential administration of an allosteric mTOR inhibitor and a catalytic mTOR inhibitor.

The pharmaceutical composition of the present invention can be formulated for particular routes of administration such as oral administration, parenteral administration, and rectal administration, etc. In one preferred embodiment of the present invention, the allosteric mTOR inhibitor and the catalytic mTOR inhibitor are administered orally. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Solid dosage forms for oral administration include capsules, tablets, pills, granules, powders or suppositories. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof In the case of capsules, tablets and pills, the dosage form may also comprise buffering agents.

Typically, the pharmaceutical compositions are tablets or gelatin capsules comprising the active ingredients together with: a) diluents (e.g., lactose, dextrose, sucrose, mannitol, sorbitol, cellulose and/or glycine); b) lubricants (e.g., silica, talcum, stearic acid, its magnesium or calcium salt and/or polyethyleneglycol); for tablets also: c) binders (e.g., magnesium aluminum silicate, starch paste, gelatin, tragacanth, methylcellulose, sodium carboxymethylcellulose and/or polyvinylpyrrolidone); if desired: d) disintegrants (e.g., starches, agar, alginic acid or its sodium salt, or effervescent mixtures); and/or e) absorbents, colorants, flavors, and sweeteners.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs.

Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

Tablets may contain the active ingredient(s) in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc.

The tablets are uncoated or coated by known techniques to delay disintegration and absorption in the gastrointestinal tract and thereby provide a sustained action over a longer period. For example, a time delay material such as glyceryl monostearate or glyceryl distearate can be employed.

An individual pharmaceutical composition comprising RTB101 may be provided as a hard gelatin capsule for oral administration comprising 5, 10, 25, or 100 mg of RTB101. The excipients may be: lactose, crospovidone, polyvinyl pyrrolidone K30, starch, Aerosil and magnesium stearate. The 5, 10, and 25 mg capsules may use a Size 4 size capsule shell; the 100 mg capsule may use a size 1 capsule shell.

Everolimus is an FDA approved drug and therefore suitable individual pharmaceutical compositions comprising of everolimus are commercially available. For example, everolimus can be administered in tablet form for oral administration in a tablet comprising a suitable amount of everolimus and butylated hydroxytoluene (BHT), magnesium stearate, hydroxypropyl methylcellulose, crospovidone and lactose as excipients. Everolimus can also be administered as a dispersable tablet comprising a suitable amount of everolimus and BHT, magnesium stearate, hydroxypropyl methylcellulose, crospovidone, colloidal anhydrous silica and lactose as excipients.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a "topical application" may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising an allosteric mTOR inhibitor and a catalytic mTOR inhibitor as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers,"

The dosages of an allosteric mTOR inhibitor and a catalytic mTOR inhibitor of the pharmaceutical compositions and combinations of the present invention are dependent on the species of the subject, the body weight, age and individual condition, or the severity of disease being treated. A physician, clinician or veterinarian of ordinary skill can readily determine the effective amount of each of the active ingredients necessary to prevent, treat or inhibit the progress of disease.

The above-cited dosage properties may be demonstrated in in vitro and in vivo tests using advantageously mammals, e.g., mice, rats, dogs, monkeys or isolated organs, tissues and preparations thereof. The compounds of the combinations of the present invention may be applied in vitro in the form of solutions, e.g., aqueous solutions, and in vivo either enterally, parenterally, advantageously intravenously, e.g., as a suspension or in aqueous solution. The dosage concentrations in vitro for everolimus or sirolimus may range between 0.001 to 500 nM, 0.1 to 450 nM, 1 to 400 nM, 100 to 350 nM, 200 to 200 nM, or about 250 nM, whereas the dosage concentrations in vitro for RTB101 may range between 0.01 to 300 nM, 1 to 200 nM, 1 to 100 nM, 25 to 75 nM, or about 50 nM. Dosage concentrations in vivo are provided hereinbefore.

EXEMPLIFICATION

Example 1

Method of Using RTB101 and Everolimus to Treat Parkinson's Disease by Inducing Autophagy in Dopaminergic Neurons and Decreasing Levels of Insoluble α-Synuclein Aggregates Step 1: Derivation of Dopaminergic Neurons from Patient Dermal Fibroblasts Induced pluripotent stem cells (iPSCs) are derived according to known methods (e.g., K. Takahashi et al., Cell 30(131): 861-72 (2007)). Briefly, iPSC lines are generated from adult human dermal fibroblasts (HDF) harvested from patients diagnosed with familial or idiopathic Parkinson's disease through retroviral expression of OCT4, SOX2, cMYC, and KLF4. Human Oct3/4, Sox2, Klf4 and c-Myc are introduced to HDF cultures (about $8\times10^5$ cells per 100 mm dish) by self-inactivating lentiviral vectors. After six (6) days the cells are trypsinized, harvested, and plated onto mitomycin C-treated SNL feeder cells (about $5\times10^4$ or $5\times10^4$ cells per 100 mm dish) in DMEM containing 10% FBS. The next day the medium is replaced with a medium for human embryotic stem (hES) cell culture, supplemented with 4 ng/mL basis fibroblast growth factor (bFGF).

Between eleven (11) and fourteen (14) days later, the iPSCs derived from the patient HDFs are differentiated into midbrain dopaminergic neurons according to known methods (e.g., L.F. Burbulla et al., Science 357(6357): 1255-61 (2017); S. Kriks et al., Nature 480(7378): 547-51 (2011)). Briefly, midbrain floor plate precursors are differentiated by incubating patient derived iPSCs with LD193189 (a small molecule ALK inhibitor), SB431542 (a TGF-β inhibitor), SHH C25II (Sonic Hedgehog N-terminus), BDNF, ascorbic acid, GDNF, FGF8, dbcAMP, TGFβ3, purmorphamine, and CHIR99021 (CHIR). Cells are passages en bloc between and plated on poly-d-Lysine (PDL)/laminin coated 100 mm dishes. Between day twenty-five (25) and thirty (30) the neural blocks are passed by accutase treatment onto PDL/laminin coated dishes. Neuralization growth factors are removed at about day forty (40) and neurons are maintained in neurobasal media containing Neurocult SM1. Cells are subjected to phenotypic screening to ensure the presence of midbrain markers such as, for example, LMX1A, NGN2, and DDC.

Alternatively, dopaminergic neuron cell lines such as, for example, SH-SY5Y human neuroblastoma cells (J. Kovalevich & D. Langford Methods Mol. Bio. 1078: 9-21 (2013)), and LUHMES (S. Schildknecht, et al., J. Neurochem. 110(s1): 13 (2009)); and primary neurons and astrocytes, may be used.

Step 2: Incubation of Combination Treatments with Patient Derived Midbrain Dopaminergic Neurons Mature patient derived midbrain dopaminergic neurons (24-32 days) are incubated with RTB101 and everolimus for twenty (20) to thirty (30) days at varying concentrations, such as, for example, the conditions recited in Table 1:

TABLE 1

RTB101 and Everolimus Concentration Schedule

| | Everolimus (0 nM) | Everolimus (0.5 nM) | Everolimus (5 nM) | Everolimus (50 nM) |
|---|---|---|---|---|
| RTB101 (0 nM) | | | | |
| RTB101 (2 nM) | | | | |
| RTB101 (10 nM) | | | | |
| RTB101 (50 nM) | | | | |

Alternatively, or in combination, mature patient derived midbrain dopaminergic neurons (24-32 days) are incubated with RTB101 and sirolimus for twenty (20) to thirty (30) days at varying concentrations, such as, for example, the conditions recited in Table 2:

TABLE 2

RTB101 and Sirolimus Concentration Schedule

| | Sirolimus (0 nM) | Sirolimus (0.5 nM) | Sirolimus (5 nM) | Sirolimus (50 nM) |
|---|---|---|---|---|
| RTB101 (0 nM) | | | | |
| RTB101 (2 nM) | | | | |
| RTB101 (10 nM) | | | | |
| RTB101 (50 nM) | | | | |

Step 3: Comparison of Treated Cells and Controls

Following incubation with RTB101 and everolimus or RTB101 and sirolimus, the patient derived midbrain dopaminergic neurons are evaluated for, among other things: β-Glucocerebrosidase activity, α-synuclein levels, and dopamine production.

Fluorimetric Analysis of β-Glucocerebrosidase Activity

Fluorometric analysis of β-Glucocerebrosidase (GCase) activity is performed according to known methods (e.g., K. O. Lee et al., Biochem Biophys Res. Comm. 337(2): 701-07 (2005)). Briefly, midbrain dopaminergic neurons subjected to treatment as described hereinabove are harvested and washed with phosphate-buffered saline (PBS), and extracted in citric acid/potassium phosphate buffer (pH 6.0) containing 0.02% (w/v) Triton X-100 and 1.0% (w/v) sodium taurocholate. The cells are lysed by sonication followed by centrifugation to remove cellular debris. Cell extract (15-20 μL) is added to GC assay buffer containing 100 mM potassium phosphate (pH 6.0), 15 mM 4-methylumbelliferylglucopyranoside (4-MUG), 0.15% (w/v) Triton X-100, 0.0125% (w/v) sodium taurocholate, and 0.1% (w/v) bovine serum albumin (BSA), for a final volume of 200 μL. The reaction is incubated for fifteen (15) minutes to one (1) hour at 37° C. and stopped by the addition of 800 μL of solution containing 100 mM glycine and 100 mM sodium hydroxide. Fluorescence is measures using a fluorometer or a microtiter plate fluorometer. One GC activity unit (U) liberates 1 nmol of 4-methylunbelliferone per hour.

Western Blot Analysis of Levels of Soluble and Insoluble α-Synuclein

Western blot analysis of soluble and insoluble α-synuclein is performed according to known methods (e.g., C. M. Woodward et al., Cell Rep. 9(4): 1173-82 (2014)). Briefly, midbrain dopaminergic neurons subjected to treatment as described hereinabove are harvested in Pierce RIPA lysis and extraction buffer ("RIPA") with 1.0% protease and 1.0% phosphatase inhibitors (about 5-10×10⁶ cells/mL). The harvested cells are sonicated for one (1) min followed by centrifugation for ten (10) minutes. The resulting pellets and supernatant are separated and the pellets are solubilized in by sonication in a minimal amount of tris buffered saline (TBS) containing sodium dodecyl sulfate (SDS) and urea. The pellet samples are then diluted with RIPA and analyzed in the same manner as the supernatant. Protein concentrations are calculated using a protein standard (e.g., Pierce BSA Protein Assay) and a plate reader per the manufacturer's instructions. Protein concentration are standardized to 20 ng protein/16.6 μL RIPA. Six fold (6×) loading buffer is added to each sample and boiled at 100° C. for five (5) minutes. Then 20 μL are loaded into each well of a 4-12% Bis-Tris polyacrylamide gel. Samples and standard (e.g., SeeBlue Pre-stained Protein Standard) are run for thirty-five (35) minutes at 200 volts.

Following gel electrophoresis, proteins are transferred to nitrocellulose membranes with a transfer kit (e.g., iBlot Nitrocellulose transfer kit). Protein-bound membranes are blocked for thirty (30) minutes with 5% non-fat dry milk in 0.1% TBS with tween (TBST).

Protein-bound, blocked membranes are then incubated with primary antibody (e.g., anti-α-synuclein AB1903 (Abcam) and anti-α-synuclein #2642S (Cell Signaling Tech)), diluted according to manufacturer recommendations, in blocking buffer overnight at 4° C. with shaking. Membranes are then washed three (3) times with TBST with HRP-conjugated secondary antibodies diluted 1:3000 in blocking buffer for two (2) hours. Membranes are then washed three (3) times with TBST, one (1) time with tris-buffered saline (TBS), then rinsed with 2 mL chemiluminescent solution. Membranes are immediately scanned and protein levels are quantified with software, using β-actin or α-tubulin for loading controls.

HPLC Analysis of Dopamine Production

HPLC analysis of dopamine production is performed according to known methods (e.g., C. M. Woodward et al., Cell Rep. 9(4): 1173-82 (2014)). Briefly, neuronal differentiation cultures are FACS sorted between 32-45 days after differentiation for obtain mature dopaminergic neurons. These cells are kept in culture on Poly-L-ornithine solution and Matrigel matrix in 24-well plates (~50-200 thousand neurons per well) for about one (1) week before harvesting. Approximately five (5) to thirty (30) minutes prior to harvesting, cells in individual wells are treated as described hereinabove. Cells are then collected in 1.2 M perchloric acid and frozen. Both the media and the lysate samples are collected separately for each treatment condition. Dopamine levels are then determined using an HPLC system (e.g., ESA Coulochem II Multi-Electrode Detector).

Example 2

Method of Using RTB101 and Everolimus to Treat Parkinson's Disease by Inducing Autophagy in Human DJ-1 KO Dopaminergic Neurons and Decreasing Levels of Insoluble α-Synuclein Aggregates Step 1: Human DJ-1 KO Isogenic Lines Human DJ-1 KO isogenic lines are derived using known methods. Briefly, CRISPR guides are designed using the Zhang Lab CRISPR Design Tool (crispr.mit.edu). Guides are selected that have high predicted activity and have off-targets with at least 3-bp mismatches in coding regions and at least 2-bp mismatches in non-coding regions. Guides are cloned into pSpCas9(BB)-2A-GFP (pX458, Addgene #48138) using standard protocols. Control iPSC (see supra Example 1) are grown to confluence in 10 cm plates. Once confluent, cells are dissociated using TrypLE Express (Life Technologies). Five million cells are transfected with 3 μg of three (3) unique CRISPR plasmids all targeting within the first coding exon of PARK7 (~1 μg of each CRISPR plasmid). The transfection is done using the NEON Transfection System (Invitrogen) using a single 1400 V, 20 ms pulse. Cells are plated in mTeSR+10 μM ROCK inhibitor (DNSK International). Forty-eight (48) hours later, cells are sorted on a BD FacsAria SORP and the top 30% GFP+cells are collected and plated for expansion. Once confluent, the cells are re-plated at clonal density in a 10 cm plate (about 10,000-20,000 cells per well) and grown until individual colonies are visible to the naked eye. Individual colonies are picked into single wells of a 48-well plate. These cells are grown to confluence and the plates are then duplicated. One of the plates is used for extraction of genomic DNA and a PCR-based approach is employed to identify cells containing indels. PCR products from clones of interest are then TOPO TA subcloned and sequenced to a depth of 10× to identify the exact nature of the mutations. The second plate is used for expansion of clones of interest upon PCR genotyping and sequencing.

Off target gene editing is assessed by using a T7 endonuclease I (T7E1) assay in the regions of highest homology to the targeted DNA sequence in DJ-1. Genomic DNA from both control and targeted cell lines is amplified by PCR using specific sets of primers for the DNA elements with the highest homology to DJ-1. PCR products are then denatured and re-annealed leading to the formation of homo and heteroduplexes, detectable by digestion with T7E1 that recognizes and cleaves mismatched DNA. The resulting cleaved and full-length PCR products are visualized by gel electrophoresis.

Differentiation of human iPSCs and DJ-1 KO iPSCs into midbrain dopaminergic neurons is done according to published protocols (supra Example 1) Cells are passaged en bloc (size of 1-2 mm) between day eleven (11) and day fourteen (14), followed by plating onto poly-d-lysine (PDL)/laminin coated 10cm dishes. Between day twenty-five (25) and day thirty (30), neural blocks are passed by accutase treatment onto PDL/laminin coated culture dishes. Neuralization growth factors are withdrawn at day 40 and neurons are maintained in Neurobasal media (Life Technologies) containing Neurocult SM1 (Stemcell technologies). Immunocytochemistry is used to verify neutralization efficiency using neural (β-III-tubulin) and midbrain (TH, FOXA2, LMX1a) specific markers.

Step 2: Incubation of Combination Treatments with DJ-1 KO Neurons

Mature DJ-KO or patient derived midbrain dopaminergic neurons (supra Example 1) are incubated with RTB101 and everolimus for forty-eight (48) hours at varying concentrations, such as, for example, the conditions recited in Table 3.

TABLE 3

RTB101 and Everolimus Concentration Schedule

| | Everolimus (0 nM) | Everolimus (0.5 nM) | Everolimus (5 nM) | Everolimus (50 nM) |
|---|---|---|---|---|
| RTB101 (0 nM) | | | | |
| RTB101 (2 nM) | | | | |

TABLE 3-continued

RTB101 and Everolimus Concentration Schedule

|  | Everolimus (0 nM) | Everolimus (0.5 nM) | Everolimus (5 nM) | Everolimus (50 nM) |
|---|---|---|---|---|
| RTB101 (10 nM) |  |  |  |  |
| RTB101 (50 nM) |  |  |  |  |

Alternatively, or in combination, mature DJ-1 KO or patient derived midbrain dopaminergic neurons (supra Example 1) are incubated with RTB101 and sirolimus for forty-eight (48) hours at varying concentrations, such as, for example, the conditions recited in Table 4.

TABLE 4

RTB101 and Sirolimus Concentration Schedule

|  | Sirolimus (0 nM) | Sirolimus (0.5 nM) | Sirolimus (5 nM) | Sirolimus (50 nM) |
|---|---|---|---|---|
| RTB101 (0 nM) |  |  |  |  |
| RTB101 (2 nM) |  |  |  |  |
| RTB101 (10 nM) |  |  |  |  |
| RTB101 (50 nM) |  |  |  |  |

Step 3: Comparison of Treated Cells and Controls

Following incubation with RTB101 and everolimus or RTB101 and sirolimus, the DJ-1 KO or patient derived midbrain dopaminergic neurons are evaluated for, among other things: relative oxidation by mitochondrial roGFP imaging, near-infrared fluorescence (nIRF) detection of oxidized dopamine, oxygen consumption rates, general oxidative stress using CM-H$_2$DCCFDA probe, electron microscopy visualization, lysosomal proteolysis and lysosomal enzyme activity, calcineurin activity, electrophysiological recording, Western blot, immunofluorescence, and dopamine and dopamine metabolites by HPLC.

Mitochondrial roGFP Imaging

Neuron mitochondria are imaged with reduction-oxidation sensitive green fluorescent protin (roGFP) using known methods (J. N. Guzman et al., Nature 468(7324): 696-700 (2010)). Briefly, neurons are transduced with AAV containing the mitochondrial roGFP construct with a CMV promoter and a mitochondrial-matrix-targeting sequence (mito-roGFP) at MOI 10 and experiments are preformed five (5) days post infection. Neurons expressing mito-roGFP are visualized using epifluorescence microscopy (excitation wavelength 410 and 470 nm, emission is monitored at 535 nm) as recently described (see, e.g., D. I. Dryanovski et al., J. Neurosci. 33(24):10154-64 (2013)).

Relative oxidation is determined from fluorescence measurements after reducing mitochondria with dithiothreitol (DTT) and then oxidizing with Aldrithiol (ALD).

The relative oxidation is calculated as $1-[(F-F_{Ald})/(F_{DTT}-F_{Ald})]$.

nIRF Detection of Oxidized Dopamine

Oxidized dopamine is detected in treated neurons according to known methods (L. F. Burbulla et al., Science 357(6357): Supp. (2017)). Briefly, neurons are scrapped in cold PBS and centrifuged at 400 g for five (5) minutes. The cell pellet is homogenized in 1% Triton X-100 lysis buffer (containing 10% glycerol, 150 mM NaCl, 25 mM Hepes pH 7.4, 1 mM EDTA, 1.5 mM MgCl$_2$, proteinase inhibitor cocktail). To ensure complete solubilization, the solution is again sonicated or vortexed depending on the amount and maturity of the dopamine quinone (DAQ)-protein adducts and neuromelanin. The solution is lyophilized until the pellet is completely dry then washed with Nanopure H$_2$O. The pellet is lyophilized again before the dried pellet is taken up in Nanopure H$_2$O and analyzed.

The standard is made from a 10 mM oxidized dopamine (DA) stock. For preparation of oxidized DA, 10 mM DA (in D-PBS) is mixed with 20 mM NaIO$_4$ (in D-PBS), vortexed briefly, and incubated for five (5) minutes at room temperature. The solution is then handled in the same way as the cell samples including centrifugation, sonication and lyophilization steps. The final pellet is taken up in Nanopure H$_2$O and standard dilution prepared.

Ten (10) μL of each sample or standard dilution is dropped onto a Biodyne Nylon Transfer Membrane (Pall, #Pall-60209) and membranes are scanned using an Odyssey infrared imaging system (Li-Cor) with the 700 channel. Samples are quantified by obtaining integrated spot intensities using Odyssey infrared imaging software, version 3.1 (Li-Cor). For in-gel nIRF detection, loading buffer is added and protein samples are heated at 95° C. for five (5) minutes before loading onto NuPAGE Tris-glycine gels (Life Technologies). After completion of the run, gels are scanned for detection of protein modified by oxidized catechols. Gels are then stained with Coomassie to visualize total protein.

Determination of Oxygen Consumption Rates

Mitochondrial oxygen consumption rates (OCR) are determined according to known methods using the XF24 Extracellular Flux Analyzer (Seahorse Bioscience) (O. Cooper et al., Sci. Transl. Med. 4(141): 141ra90 (2012)). Briefly, on the day of experiment, culture media is replaced with fresh media prior to plate pre-incubated in a CO$_2$—-free incubator at 37° C. for one (1) hour for equilibration before processing in the XF24 Extracellular Flux Analyzer.

For baseline measurements, a twenty (20) minute equilibration step is followed by three cycles of two (2) minute mix, three (3) minute wait, and two (2) minute measurement time.

For analysis of drug response, three cycles of two (2) minute mix, three (3) minute wait, and two (2) minute measurement are used per condition.

After three (3) baseline measurements, oligomycin (1 μM), CCCP (1 μM), and antimycin A (1 μM) are added sequentially, with three (3) measurements per condition. For normalization of cell number, cells are harvested after the experiment in RIPA buffer and protein concentration are measured.

General Oxidative Stress Assay using CM-H$_2$DCCFDA Probe

CM-H$_2$DCFDA (2',7'-dichlorodihydrofluorescein diacetate) (Thermo Fisher Scientific) is used in cultured cells as a general organelle-nonspecific cell-permeant indicator of reactive oxygen species (ROS) (e.g., hydrogen peroxide, hydroxyl radical, carbonate radical, and nitrogen dioxide) according to manufacturer's instructions. Approximately 5 μM of CM-H$_2$DCFDA is used with an incubation time of about ten (10) minutes.

Electron Microscopy

Neurons are fixed with 2.5% glutaraldehyde in 0.1 M sodium cacodylate buffer, pH 7.3 for one (1) hour, rinsed several times with PBS, followed by post fixation with 1% osmium tetroxide in PBS for one (1) hour. Specimens are rinsed again with PBS for fifteen (15) minutes and then dehydrated through a series of graded ethyl alcohols from 50 to 100%. Specimens are embedded, resin blocks are sectioned, and samples are imaged.

Lysosomal proteolysis in Live Neurons and Lysosomal Enzyme Activity Assays

Long-lived protein degradation assays are performed by radioactive pulse-chase using tritium-labeled leucine (Perkin-Elmer, #NET460A001MC) according to known methods (S. Kaushik & M. Cuervo, Methods Enzymol. 452: 297-324 (2009)). Briefly, proteins are labeled with radioactive leucine for thirty-six (36) hours (pulse period), followed by a chasing period of twenty-eight (28) hours. Short-lived proteins are excluded from the analysis by replacing the media after one (1) hour of chasing period with fresh chasing media.

For lysosomal inhibition, 100 mM of leupeptin is added to the initial medium (pulse period) and 100 mM of leupeptin and 5 mM of $NH_4Cl$ are added to the chasing medium. Aliquots of culture media are sampled after eight (8), twenty (20) and twenty-eight (28) hours during chasing period and precipitated with 20% (v/v) trichloroacetic acid with 0.5 mg/mL BSA for a minimum of eight (8) hours at 4° C. followed by centrifugation at 20,000 g for twenty (20) minutes at 4° C. Pellets are resuspended in 0.1 N NaOH/0.1% sodium dexoycholate. After the last time point, cells are scrapped and harvested in 0.1 N NaOH/0.1% sodium dexoycholate.

Radioactive counts of cell lysates and secreted proteins are measured using a liquid scintillation analyzer (TriCarb 2800TR, Perkin Elmer). Percentage of secreted proteins are determined by dividing the radioactive signal obtained from the media by the total radioactive counts obtained from the cell lysate. Lysosomal proteolysis is calculated as the difference between control and inhibited conditions.

Enzyme activity assays are performed using the artificial enzyme substrates 4MU-glucopyranoside (for GCase) and 4MU-sulfate potassium salt (for $\alpha$-i-2-sulf) as previously described (J. R. Mazzulli et al., Cell 146(1): 37-52 (2011)). Five (5) µg cell lysate is added to 10 µL of 10% BSA (in activity assay buffer: 0.25% (v/v) Triton X-100 (Sigma-Aldrich #T-8787)) and to 20 µL of 5 mM artificial enzyme substrate (in activity assay buffer). The mixture is added up to 100 µL total with activity assay buffer, 0.25% (w/v) taurocholic acid (Sigma-Aldrich, #T9034), 1 mM EDTA, in citrate/phosphate buffer (pH 5.4). Samples are mixed and incubated at 37° C. for thirty (30) minutes. The reaction is stopped by adding 100 µL of stop solution (1 M glycine, pH 12.5) to each sample. Samples are loaded into a 96-well fluoro plate (F16 Black Maxisorb Plate, Nunc #475515) and fluorescence is recorded using a plate reader (Ex=365 nm, Em=445 nm; top read).

Calcineurin Activity Assay

Calcineurin Cellular Activity Assay Kit (Enzo, #BML-AK816) is used in cultured cells to measure cellular calcineurin phosphatase activity according to manufacturer's instructions. Briefly, neurons are scrapped in cold PBS and centrifuged at 400 g for five (5) minutes. Immediately before use, a protease inhibitor tablet is added to the lysis buffer (50 mM Tris pH 7.5, 0.1 mM EdTa, 0.1 mM EGTA, 1 mM DTT, 0.2% (v/v) NP-40). The neuron cell pellet is first washed with cold TBS buffer (20 mM Tris pH 7.2, 150 mM NaCl) and any excess buffer is blotted. The cell mass is weighed and lysis buffer is added (~0.33-0.5 mL/g tissue). Cells are broken up by passing the mixture through a sixteen (16) gauge needle. Free phosphates are optionally removed using a desalting resin. The neuron lysates are immediately frozen at −70° C. until used.

For the calcineurin assay, cell lysates are thawed and protein levels are quantified. Controls and phosphate standards are prepared according to manufacturer's instructions. Approximately 2 µg of total protein are used for sample wells. Following reaction initiation the assay plate is incubated at ~30° C. for thirty (30) minutes then 100 µL of BIMOL GREEN reagent is added to all sample and phosphate standard wells. Reactions are allowed to develop for twenty (20) to thirty (30) minutes and $OD_{620\ nm}$ is read on a microplate reader.

Electrophysiological Recordings

For patch-clamp recordings, coverslips are transferred to a chamber perfused by gravity at 2 mL/min with ACSF containing: 125 mM NaCl, 25 mM $NaHCO_3$, 2.5 mM KCl, 1.25 mM $NaH_2PO_4$, 2 mM $CaCl_2$, 1 mM $MgCl_2$, and 25 mM glucose, bubbled with a mixture of 95% $O_2$ and 5% $CO_2$ at 33-34° C. Patch pipettes (3-3.5 M$\Omega$) pulled from borosilicate glass are filled with internal solution containing: 135 mM K—$MeSO_4$, 5 mM KCl, 5 mM HEPES, 0.05 mM EGTA, 10 mM phosphocreatine-di(tris), pH 7.3 (290-300 mOsm). The patch pipette is tip-filled with internal solution and back-filled with internal solution containing gramicidin (Sigma-Aldrich, working concentration ~20 µg/mL). Cells are visualized by infrared differential interference contrast video microscopy and electrophysiological recordings are filtered at 1-4 kHz and digitized at 5-20 kHz, and collected.

Western Blot Analysis

Neuronal proteins are analyzed according to known methods (J. R. Mazzulli et al., Cell 146(1): 37-52 (2011)). Briefly, neurons are scrapped in cold PBS and centrifuged at 400 g for five (5) minutes. PBS is removed and the cell pellet is homogenized in 1% Triton X-100 lysis buffer (containing 10% glycerol, 150 mM NaCl, 25 mM Hepes (pH 7.4), 1 mM EDTA, 1.5 mM $MgCl_2$, and proteinase inhibitor cocktail) as previously described. Lysates are analyzed by Western blot using Odyssey Blocking Buffer (LI-COR Biosciences, #927-50100), and incubated with the following primary antibodies:

α-synuclein (Life Technologies LB509, 1:500);
syn211 (Sigma-Aldrich, #S5566, 1:1000);
C-20 (Santa Cruz #SC-7011-R, 1:1000);
syn303 (BioLegend, #MMS- 5085, 1:500);
syn202 (#MMS-529R, 1:1000);
DJ-1 (abcam, #ab18257, 1:1000);
oxidized DJ-1 (abcam, #ab169520, 1:500);
synapsin (Santa Cruz, #sc-398849, 1:1000);
calcineurin (abcam, #ab3673, 1:1000);
tyrosine hydroxylase (TH) (EMD Millipore, #657012, 1:1000);
β-III-tubulin (Covance, 1:5000);
GAPDH (Millipore, #MAB374, 1:5000);
β-actin (abcam, #ab11003, 1:5000);
vimentin (1:5000);
α-tubulin (Sigma, #t5168, 1:5000); and
neural specific enolase (Pierce, #PA5-12374, 1:1000).

Syn303 antibody is used to detect oxidized forms of α-synuclein, as previously described (J. E. Duda et al., Ann. Neurol. 52(2): 205-10 (2002)).

Immunofluorescence

Neurons are fixed in 4% paraformaldehyde and permeabilized with 0.3% Triton X-100 in PBS. Cells were blocked in 1-2% BSA, 5% normal goat serum in PBS-Triton for thirty (30) minutes and the following primary antibodies are used:

anti β-III-tubulin (Covance, #MMS- 435P, 1:1000 or Covance, #MRB-435P, 1:1000);
tyrosine hydroxylase (EMD Millipore, #657012, 1:1000);
HNF-3 beta (FOXA2) (Santa Cruz, #sc-101060, 1:100);
LMX1A (EMD Millipore, #AB10533, 1:1000);
NANOG (Abeam, #ab80892, 1:1000);

OCT4 (Abcam, #ab19857, 1:300);
SSEA4 (Merck KGaA, #MAB4304, 1:100);
TRA-1-81 (Merck KGaA, #MAB4381, 1:50);
AFP (Sigma Aldrich, #A8452, 1:100);
SMA (Dako, #M0851, 1:100).

Primary antibodies are incubated overnight, washed in PBS, and incubated with Alexa-conjugated anti-rabbit or anti-mouse antibodies at 1:500. Images are analyzed and captured at equal exposure times. For quantification, the number of cells is normalized to total cells in the field of view (calculated by nuclear DAPI stain). At least three (3) fields of view are analyzed per coverslip.

Determination of Dopamine and Metabolites by HPLC

Measurement of levels of dopamine, L-DOPA and DOPAC is performed using reversed-phase HPLC with electrochemical detection. Neurons are harvested in 50 µL of 0.1 M perchloric acid containing 100 nM 3,4 dihydroxybenzylamine (DHBA). Cell lysates are homogenized and centrifuged at 16,000 g for ten (10) minutes at 4° C. Supernatants are filtered through 0.22 µm membranes, and 40 µL per sample is injected on the HPLC for analysis of dopamine levels and metabolites using an Agilent (Palo Alto, Calif.) 1200 series HPLC controlled by ChemStation software (Agilent). Catechols are resolved on a reverse-phase C18 ZORBAX Eclipse XDB column (150 mm×4.6 mm, 5 µm; Agilent, Santa Clara, Calif.) at a flow rate of 1 mL/min in a mobile phase consisting of 66 mM citric acid, 34 mM sodium phosphate, 2% methanol, and 0.04% sodium azide, pH 2.0, and using a Coularray detector (Thermo Scientific) with the following working potentials (in mV): −200, +200, +300, and +400. Quantification of dopamine and metabolites is done by comparing the peak areas of a known amount of standards and using CoulArray Data Station software (version 3.00). Normalization is based on concentration of total protein.

Example 3

Method of Using RTB101 and Everolimus to Treat Parkinson's Disease by Inducing Autophagy in Mouse Derived Dopaminergic Neurons and Decreasing Levels of Insoluble α-Synuclein Aggregates Step 1: Derivation of Mouse iPSC Dopaminergic Neuron Cultures Mouse iPSC lines are generated from WT and DJ-1 KO mouse embryonic fibroblasts through Sendai virus reprogramming vectors OCT4, SOX2, cMYC and KLF4 according to known methods. Both mouse iPSC lines express pluripotency markers. Differentiation of mouse iPSCs into midbrain dopaminergic neurons is accomplished according to known methods (S. H. Lee et al., Nat. Biotechnol. 18(6): 675-9 (2000)). Briefly, undifferentiated iPSCs are grown on gelatin-coated tissue culture plates in stem cell media containing leukemia inhibitory factor (LIF). To induce embryoid body (EB) formation, the cells are washed and dissociated into a single-cell suspension by incubating in trypsin/EDTA (0.05%/0.53 mM) and plated onto ultra-low attachment flasks. The EBs are formed in stem cell medium for four (4) days and then plated onto fibronectin-coated tissue culture surfaces in stem cell medium. After twenty-four (24) hours, the medium is replaced with serum-free medium containing insulin, transferrin and selenium. After sic (6) to eight (8) days cells are dissociated by trypsin/EDTA (0.05%/0.53 mM) and plated onto PDL/laminin-coated tissue culture plates or glass coverslips in serum-free medium containing insulin, transferrin, selenium, putrescine and progesterone supplemented with 10 ng/mL of bFGF in the presence of murine N-terminal fragment of SHH and murine FGF8. Cells are then expanded for four (4) to six (6) days. Final differentiation is induced by removal of bFGF, SHH and FGF8. The final differentiation medium contains insulin, transferrin, selenium, putrescine and progesterone supplemented with cAMP and AA. The cells are cultured under differentiation conditions until about day twenty-five (25) of differentiation, when the neutralization factors were withdrawn.

Step 2: Incubation of Combination Treatments with Mouse iPSCs

Mature mouse derived WT or DJ-1 KO neurons are incubated with RTB101 and everolimus for forty-eight (48) hours at varying concentrations, such as, for example, the conditions recited in Table 5.

TABLE 5

RTB101 and Everolimus Concentration Schedule

| | Everolimus (0 nM) | Everolimus (0.5 nM) | Everolimus (5 nM) | Everolimus (50 nM) |
|---|---|---|---|---|
| RTB101 (0 nM) | | | | |
| RTB101 (2 nM) | | | | |
| RTB101 (10 nM) | | | | |
| RTB101 (50 nM) | | | | |

Alternatively, or in combination, mature mouse derived WT or DJ-1 KO neurons are incubated with RTB101 and sirolimus for forty-eight (48) hours at varying concentrations, such as, for example, the conditions recited in Table 6.

TABLE 6

RTB101 and Sirolimus Concentration Schedule

| | Sirolimus (0 nM) | Sirolimus (0.5 nM) | Sirolimus (5 nM) | Sirolimus (50 nM) |
|---|---|---|---|---|
| RTB101 (0 nM) | | | | |
| RTB101 (2 nM) | | | | |
| RTB101 (10 nM) | | | | |
| RTB101 (50 nM) | | | | |

Step 3: Comparison of Treated Cells and Controls

Following incubation with RTB101 and everolimus or RTB101 and sirolimus, WT or DJ-1 KO mouse derived midbrain neurons are evaluated for, among other things: mitochondrial roGFP imaging, near-infrared fluorescence (nIRF) detection of oxidized dopamine, oxygen consumption rates, general oxidative stress using CM-H2DCCFDA probe, electron microscopy visualization, lysosomal proteolysis and lysosomal enzyme activity, calcineurin activity, electrophysiological recording, Western blot, immunofluorescence, and dopamine and dopamine metabolites by HPLC. Methods and procedures utilized are comparable to those previously described (supra Examples 1 and 2).

Example 4

Method of Using RTB101 and Everolimus to Treat Parkinson's Disease in In Vivo Mouse Models Step 1: Generation of Transgenic Mice Wildtype C57BL/6 mice (Charles River) and DJ-1$^{-/-}$ (T. Dawson) mice back-crossed onto the C57BL/6 line are bred and handled in accordance with the US National Institutes of Health Guide to the Care and Use of Laboratory Animals and Society for Neuroscience guidelines.

DJ-1 KO mice are produced according to known methods (L. Chen et al.,J. Biol. Chem. 280(22): 21418-26 (2005)). These mice are then crossed with DASYN53 double-transgenic mice (L. Chen et al., J. Neurosci. 35(3): 890-905 (2015))) to generate DASYN53×DJ-1 KO triple-transgenic mice. Briefly, a tetracycline inducible system-based "PF" strategy with amplified expression limited to dopamine (DA) neurons is used. The Tet operator (tetO)—tetracycline responsive transactivator (tTAt) "PF" cassette is inserted between the DA transporter (DAT) gene promoter and the coding sequence via gene targeting. With this "PF" design, the tetO promoter directs the expression of tTA, which in turn activates the tetO promoter. An additional tTA is inserted right downstream of the DATpromoter and upstream of the "PF" cassette. The gene targeting construct also contains a transcriptional "stop" and a floxed PGK-neo cassette for selection during embryonic stem (ES) cell culture.

Primogenix PRX-129/S6 ES cells are used for targeting. Male chimeras are crossed with a germ line deleter, Meox2-cre (The Jackson Laboratory), to remove the PGK-neo cassette. The resulting DAT-PF-tTA line is crossed with the Tg(tetO-SNCA_A53T)E2Cai/J line obtained from The Jackson Laboratory (X. Lin et al., Neuron 64(6): 807-27 (2009))) to generate DASYN53 double-transgenic mice.

Step 2: Treatment of Wildtype and DJ-1 KO Mice with Combination Treatments

Wildtype and DJ-1 KO mice are administered RTB101 and everolimus, or RTB101 and sirolimus for up to fourteen (14) months) at varying concentrations. RTB101 is administered between 0-400 mg/kg/day. Everolimus or sirolimus are administered between 0-40 mg/kg/week. Negative control animals are not treated with catalytic nor allosteric mTOR inhibitors.

Step 3: Comparison of Treated Cells and Controls

Following administration of RTB101 and everolimus or RTB101 and sirolimus, combination WT or DJ-1 KO mouse brain tissue is evaluated for, among other things: nIFR detection of oxidized dopamine, Western blot, and homocysteine levels.

Near-infrared Fluorescence Detection of Oxidized Dopamine

Freshly dissected tissue from different regions of DJ-1 KO and wildtype mice is homogenized in 1% Triton X-100 lysis buffer according to tissue weight. Insoluble pellets from a 100,000 g spin (~30 min, 4° C.) is extracted in 2% SDS/50 mM Tris pH 7.4 by boiling and sonication. SDS buffer volume per sample is normalized according to protein concentration of the T-soluble fraction. Leftover insoluble pellets from a 150,000 g spin (~30 min, 4° C.) is further extracted in 1N NaOH (half the volume of the SDS buffer volume) and incubated at 55° C. overnight. The volume of NaOH for extraction is calculated depending on the protein concentration of the soluble fraction. To ensure complete solubilization, the solution is again sonicated or vortexed depending on the amount and maturity of the dopamine quinone (DAQ)-protein adducts and neuromelanin. Samples are then treated as previously described for cell culture neurons (supra Example 2).

Western Blot Analysis

Freshly dissected brain tissue from DJ-1 KO and wildtype mice is homogenized in 1% Triton X-100 lysis buffer according to tissue weight. Insoluble pellets from a 100,000 g spin are further extracted in 2% SDS/50 mM Tris pH 7.4 by boiling and sonication. Lysates are then analyzed as previously described for cell culture neurons (supra Examples 1 and 2)

Quantitative Determination of Homocysteine Levels

Supernatants of homogenates derived from nigral tissue of WT and DJ-1 KO mice administered combinations of RTB101 and everolimus, RTB101 and sirolimus, or vehicle are analyzed for homocysteine levels using an immunoassay kit with a detection range of 0.78-50 ng/mL according to manufacturer's instructions (amsbio, #AMS.E0772Ge). Approximately 50 µg is used per sample.

Example 5

Method of Using RTB101 and Everolimus to Treat Alpha-1 Antitrypsin (AAT) Deficiency-Related Liver Disease by Inducing Autophagy in Hepatocytes and Decreasing Levels of Mutant AAT Polymers Step 1: Derivation of Hepatocytes from Patient Dermal Fibroblasts Induced pluripotent stem cells were derived according to known methods (e.g., A. Somers et al., Stem Cells. 28(10): 1728-40 (2010)). Briefly, iPSC lines were generated from adult HDFs harvested from patients with alpha-1 antitrypsin deficiency due to the inheritance of two Z alleles of the AAT protease inhibitor (PiZZ). Samples were digested overnight at 37° C. with 0.25% collagenase I and 0.05% DNase I in high-glucose Dulbecco's modified Eagle's medium (DMEM) containing 20% fetal bovine serum (FBS). Cell suspensions were cultured in T75 plates to obtain outgrowth of dermal fibroblasts.

After three (3) to four (4) passages the patient derived dermal fibroblasts were plated in DMEM with 10% FBS on gelatin-coated tissue culture dishes (about $1\times10^5$ cells per plate). The next day polybrene was added to the media (5 µg/mL), and the cells were infected with hSTEMCCA-loxP lentiviruses. The next day the media was changed to serum-free "iPSC" media containing DMEM F12 with 20% KnockOut Serum Replacement, 1 mM non-animal L-glutamine, 0.1 mM β-mercaptoethanol, 1% nonessential amino acid solution, and FGF2 (10 ng/mL). On day six (6) the plate well was trypsinized and passed at a 1:16 split by plating onto 100 mm gelatin coated culture dishes that were pre-seeded with mitomycin C-inactivated mouse embryonic fibroblast (MEF) feeders in iPSC media.

iPSC colonies were mechanically isolated thirty (30) days post transduction and colonies with one (1) copy of hSTEM-CCA were expanded on MEF feeder plates in iPSC media. The single copy lentiviral cassette in each colony was removed via Cre-mediated hSTEMCCA excision. iPSC colonies were then differentiated into hepatocytes. First, iPSC cells were plated on Matrigel-coated dishes and differentiated in a step-wise protocol as previously described (e.g., X. Cheng et al., Cell Stem Cell. 10(4):371-84 (2012), and summarized in Table 7.

TABLE 7

Media Schedule for Hepatocyte Differentiation

| | Day(s) | | | | | |
|---|---|---|---|---|---|---|
| | $T_0$ | $T_{1-2}$ | $T_{3-4}$ | $T_{7-12}$ | $T_{13-18}$ | $T_{19-24}$ |
| Media | A | B | C | D | E | F |

Media A consists of RPMI-based serum-free medium with Chir 99021 (2 µg/mL), Activin A (100 ng/mL), L-glutamine (2 mM), and MTG ($4.5\times10^{-4}$ M).

Media B consists of RPMI-based serum-free medium with BMP4 (0.5 ng/mL), FGF2 (10 ng/mL), Activin A (100 ng/mL), VEGF (10 ng/mL), L-glutamine (2 mM), and MTG ($4.5 \times 10^{-4}$ M).

Media C consists of SFD media with BMP4 (0.5 ng/mL), FGF2 (10 ng/mL), Activin A (100 ng/mL), VEGF (10 ng/mL), L-glutamine (2 mM), and MTG ($4.5 \times 10^{-4}$ M).

Media D consists of SFD media with ascorbic acid (50 mcg/mL), MTG ($4.5 \times 10^{-4}$ M), BMP4 (50 ng/mL), FGF2 (10 ng/mL), VEGF (10 ng/mL), EGF (10 ng/mL), TGFα (20 ng/mL), HGF (100 ng/mL), and dexamethasone (0.1 μM).

Media E consists of SFD media with ascorbic acid (50 mcg/mL), MTG ($4.5 \times 10^{-4}$ M), FGF2 (10 ng/mL), VEGF (10 ng/mL), EGF (10 ng/mL), TGFα (20 ng/mL), HGF (100 ng/mL), Oncostatin M (20 ng/mL), vitamin K (6 μg/mL), y-secretase inhibitor (1.5 μM), dexamethasone (0.1 μM), and DMSO (1%).

Media F consists of SFD media with ascorbic acid (50 mcg/mL), MTG ($4.5 \times 10^{-4}$ M), HGF (100 ng/mL), Oncostatin M (20 ng/mL), vitamin K (6 μg/mL), and dexamethasone (0.1 μM).

Step 2: Incubation of Combination Treatments with Patient Derived Hepatocytes

Mature patient derived hepatocytes (20 days) were incubated with RTB101 and everolimus for forty-eight (48) hours at varying concentrations, such as, for example, the conditions recited in Table 8.

TABLE 8

RTB101 and Everolimus Concentration Schedule

|  | Everolimus (0 nM) | Everolimus (0.5 nM) | Everolimus (5 nM) | Everolimus (50 nM) |
|---|---|---|---|---|
| RTB101 (0 nM) |  |  |  |  |
| RTB101 (2 nM) |  |  |  |  |
| RTB101 (10 nM) |  |  |  |  |
| RTB101 (50 nM) |  |  |  |  |

Alternatively, or in combination, mature patient derived hepatocytes (20 days) were incubated with RTB101 and sirolimus for forty-eight (48) hours at varying concentrations, such as, for example, the conditions recited in Table 9.

TABLE 9

RTB101 and Sirolimus Concentration Schedule

|  | Sirolimus (0 nM) | Sirolimus (0.5 nM) | Sirolimus (5 nM) | Sirolimus (50 nM) |
|---|---|---|---|---|
| RTB101 (0 nM) |  |  |  |  |
| RTB101 (2 nM) |  |  |  |  |
| RTB101 (10 nM) |  |  |  |  |
| RTB101 (50 nM) |  |  |  |  |

Step 3: Comparison of Treated Cells and Controls

Following incubation with RTB101 and everolimus or RTB and sirolimus, the patient derived hepatocytes were evaluated for, among other things: intracellular AAT, secretion of AAT and albumin, AAT (Serpinal) expression, and drug-induced toxicity resistance.

Flow Cytometry Analysis of Intracellular AAT

Flow cytometry analysis of intracellular AAT was performed according to known methods (e.g., A. A. Wilson et al., Stem Cell Reports. 4(5): 873-85 (2015)). Briefly, the patient derived hepatocytes subjected to treatment as described hereinabove were fixed in 1.6% paraformaldehyde for twenty (20) minutes at 37° C. and then permeabilized in saponin buffer. Fixed cells were stained with antibodies against human AAT (e.g., Santa Cruz; #sc-101058). Gating is based on the isotype-stained controls. Staining was quantified using a FACS flow cytometer and analyzed with software (e.g., FlowJo).

Figure 2:
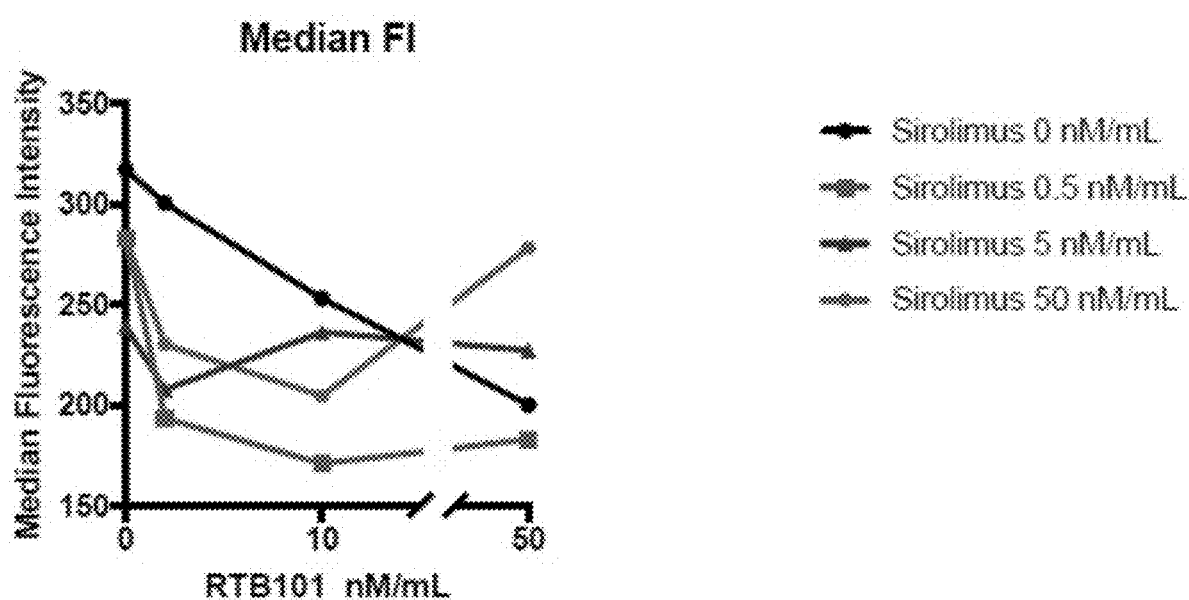
FIG. 2 shows the median fluorescence of patient derived human alpha-1 anti-trypsin deficient (Pizz) hepatocytes treated with combinations of RTB101 and sirolimus in a FACS assay for intracellular AAT.

Results for the FACS analysis of intracellular alpha-1 anti-trypsin in patient derived AAT deficient (Pizz) hepatocytes treated with combinations of RTB101 and sirolimus are summarized in FIG. 1 and FIG. 2. It can be seen that the combination of RTB101 and sirolimus decreases intracellular AAT, as measured by fluorescence, to a greater degree than either treatment alone.

Figure 3:
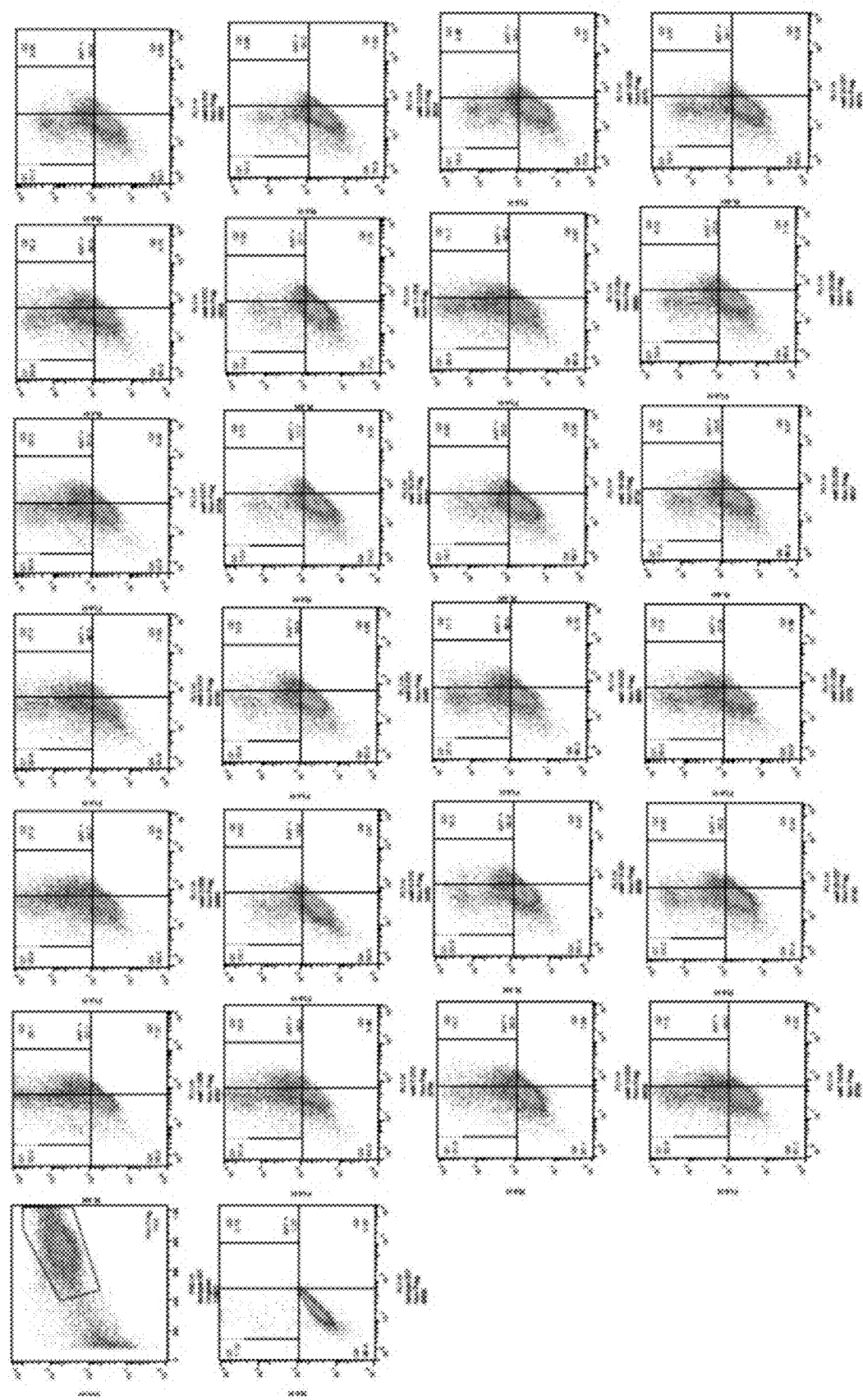
FIG. 3 shows the gating in the FACS assay for intracellular AAT in patient derived human alpha-1 anti-trypsin deficient (Pizz) hepatocytes treated with combinations of RTB101 and sirolimus.

Images of the FACS gating are shown in FIG. 3.

ELISA Analysis of Secreted AAT and Albumin

ELISA measurement of hAAT secretion is performed according to known methods (e.g., A. A. Wilson et al., Am. J. Respire. Cell Mol. Biol. 39(2): 133-41 (2008)). Briefly, the hAAT secreted by hepatocytes subjected to treatment as described hereinabove is measures by dual antibody, sandwich enzyme-linked immunosorbent assay (ELISA). Rabbit anti-human alpha-1 antitrypsin antibody (capture antibody) is used to coat 96-well microtiter plates. Following antibody fixing, the plates are blocked with 3% bovine serum albumin (BSA) in phosphate buffered saline (PBS). Standards are generated by serial dilution of human alpha-1 antitrypsin in PBS with 0.5% (w/v) BSA and 0.05% (v/v) Tween 20. Samples and standards are plated in duplicate and incubated at 4° C. overnight, followed by peroxidase conjugated goat anti-human AAT antibody (EY Labs; #PA-2115-1). Human AAT is quantified by optical densitometry after incubation with ABTS peroxidase substrate solution.

ELISA measurement of albumin secretion is performed according to known methods (e.g., Albumin Human ELISA kit (Abcam)).

Quantification of AAT (Serpinal) Expression

AAT expression is quantified according to known methods such as qPCT, Nanostring, and digital PCR (e.g., A. A. Wilson et al., Stem Cell Reports. 4(5): 873-85 (2015)). Briefly, total RNA and miRNA is isolated from patient derived hepatocytes subjected to treatment as described hereinabove using a miRNA isolation kit (e.g., miRNAeasy (Qiagen). Approximately 200-1000 ng of RNA is then reverse transcribed into cDNA using random hexamers. Real-time, qualitative PCR (qPCR) is performed for all samples using primer mixes (e.g., SYBR Green QPCR master mix and TaqMan primers and master mix) and a PCR system (e.g., Light Cycler 48011 qPCR (Roche) and StepOne Real Time PCR (Applied Biosystems).

MTT Viability Analysis of Drug-Induced Toxicity Resistance

MTT viability analysis of drug induced toxicity resistance is performed according to known methods using an MTT assay kit (e.g., MTT Assay Kit and Protocol (Abcam)). Briefly, patient derived hepatocytes are cultured in a 96 well plate. When the hepatocytes are mature (~20 days) the media is carefully aspirated and 50 μL of serum free media and 50 μL of MTT solution is added to each well. The plate is then incubated at 37° C. for three (3) hours, followed by the addition of 150 μL of MTT solvent into each well. The plate is wrapped in foil and gently shaken to fifteen (15) minutes and the absorbance is measured at OD=590 within one (1) hour. Each sample is run in duplicate and the medium background is subtracted from the assay reading. The percent cytotoxicity is determined by subtracting the corrected absorbance for the samples from the corrected absorbance for the control and multiplying by 100.

Example 6

Combination of Sirolimus and RTB101 for Treatment of Patients with Glucocerebrosidase Gene Mutations-associated Parkinson's Disease A total of approximately sixty (60) persons who are heterozygous or homozygous carriers of a glucocerebrosidase gene (GBA) mutation associated with Parkinson's disease (PD) will be enrolled in a multicenter, double blind, placebo-controlled trial to assess the safety, tolerability, and central nervous system (CNS) exposure of oral RTB101 and sirolimus, alone or in combination, as compared to placebo. The study will be comprised of adult males and females who exhibit mild-moderate GBA-PD, i.e., modified Hoehn and Yahr (mH&Y) stage≤3.

Patients will be randomly assigned to one of five (5) cohorts to assess the safety, tolerability, and efficacy of sirolimus and RTB101, alone on in combination. The dosing regiments include: placebo, RTB101 (300 mg weekly), sirolimus (2 mg weekly), and combination RTB101 and sirolmus (300 mg weekly plus 2, 4, or 6 mg weekly, respectively).

All patients who received at least part of one dose of study drug will be considered as "treated" will be included in the Full Analysis Set (FAS) for assessment of efficacy and safety.

Safety and Tolerability

Continuous safety data will be summarized with descriptive statistics (arithmetic mean, SD, median, minimum, and maximum) by dose level. Categorical safety data will be summarized with frequency counts and percentages by dose level. Adverse events will be coded using the most current Medical Dictionary for Regulatory Activities (MedDRA®) available. A by-participant AE data listing, including verbatim term, preferred term, system organ class, treatment, severity, and relationship to study drug will be provided. The number of participants experiencing treatment emergent AEs (TEAEs) and number of individual TEAEs will be summarized by treatment group, system organ class, and preferred term. TEAE's will also be summarized by severity and by relationship to study drug.

Laboratory evaluations and vital signs assessments will be summarized by Cohort and protocol specified collection time point. A summary of change-from-baseline at each protocol specified time point by Cohort will also be presented.

Pharmacokinetic Evaluations

The analysis will be conducted with mixed-effects (population) methods. A dataset suitable for the analysis will be constructing using R (r-project.org, version 3.3.2 or later). The analysis will be conducted using the NONMEM system (Icon Development Solutions, Hanover, MD, version 7.3 or later) and PLT Tools (pltsoft.com; version 5.3.0 or later). One- and two-compartment linear models with first-order absorption and first-order elimination will be evaluated initially. If diagnostic graphics suggest that these models are not appropriate, other models will be considered. A systemic search will then be applied to determine the impact of covariates (age, body size, gender, race, drug-drug interactions, organ function) on the pharmacokinetic parameters, focusing on apparent clearance and absorption rate. Once a final model is determined, model validation will include some combination of visual predictive check (with and without prediction-correct), likelihood profiles, and bootstrap analyses.

Patient Selection

Patients will be subjected to extensive screening prior to inclusion in the study. To be eligible for inclusion in the study, a patient must fulfill all of the following:

Inclusion Criteria:

1. Patient must be able to communicate well with the investigator, and to understand and comply with the requirements of the study.
2. Signed informed consent must be obtained before any study assessment is performed.
3. Male and female adults 18 years of age and older at the time of informed consent signing
4. Patients must weigh ≥40 kg and ≤150 kg
5. Diagnosis of Parkinson's Disease with a Modified Hoehn and Yahr stage of ≤3 at screening
6. Heterozygous or homozygous carriers of a GBA mutation associated with PD.
7. Stable medication regimen of PD drugs for at least 30 days (at least 60 days for rasagiline) prior to randomization.
8. At screening and baseline, vital signs (systolic and diastolic blood pressure, pulse rate and respiratory rate) will be assessed in a sitting position after the patient has rested for at least three (3) minutes. Sitting vital signs should be within the following ranges:
   a. Oral or tympanic body temperature between 35.0-37.5° C.
   b. Systolic blood pressure, 90-160 mm Hg
   c. Diastolic blood pressure, 50-95 mm Hg
   d. Pulse rate, 40-95 bpm If vital signs are outside these ranges, the Investigator may obtain up to two additional readings, so that up to 3 consecutive assessments are made. At least the last set of readings must be within the ranges provided above at the baseline visit in order for the patient to qualify.

Otherwise eligible patient will be excluded from the study for any of the following:

Exclusion Criteria:

1. Parkinsonism due to drug(s) or toxin(s) or with history of a prior brain MRI without contrast showing a structural abnormality that is a possible cause of their PD signs or symptoms
2. Patients with prior surgical history of deep brain stimulation (DBS).
3. A Montreal Cognitive Assessment score <20 at baseline visit.
4. If female, pregnancy (defined as positive beta-human chorionic gonadotrophin [Beta-hCG] blood test) or lactating or breast-feeding.
5. Women of childbearing potential (any woman physiologically capable of becoming pregnant) unless they remain on highly effective methods of contraception throughout the study and for 12 weeks following discontinuation of the study drug. The study drug may impact the effectiveness of hormonal contraceptives therefore hormonal contraceptives should not be relied on as an effective method of contraception. Highly effective contraception methods include:
   a. Total abstinence (when this is in line with the preferred and usual lifestyle of the patient. Periodic abstinence (i.e., calendar, ovulation, symptothermal, postovulation methods) and withdrawal are not acceptable methods of contraception.

b. Female sterilization (have had surgical bilateral oophorectomy (with or without hysterectomy), total hysterectomy or tubal ligation at least six weeks before taking study treatment. In case of oophorectomy alone, only when the reproductive status of the woman has been confirmed by follow up hormone level assessment.
c. Male sterilization (at least 6 months prior to screening). The vasectomized male partner should be the sole partner for that patient.
d. Placement of an intrauterine device (IUD) or intrauterine system (IUS).

6. Sexually active male patients with a partner of childbearing potential must be willing to wear a condom while on study drug and for 12 weeks after stopping study drug and should not father a child in this period. A condom is required to be used also by vasectomized men with a partner of child-bearing potential in order to prevent delivery of the drug via seminal fluid.
7. Use of other investigational drugs within 5 half-lives of randomization, or within 30 days, whichever is longer; or longer if required by local regulations.
8. History of hypersensitivity or allergy to sirolimus, RTB101 or their excipients or to other mTOR inhibitor drugs.
9. Concomitant use of any of the drugs (including strong CYP3A4 inhibitors or inducers) or other treatments (including live vaccines) listed in the Table below.
10. Any one of the following hematologic or coagulation abnormalities at screening: hemoglobin <10.0 g/dL for males and <9.0 g/dL for females; white blood cell (WBC) count <3,500/mm3; neutrophil count <2,000/mm3; platelet count <125,000/mm3; international normalized ratio (INR) >1.2; or, partial prothromboplastin time (PTT) >35 seconds.
11. Patients receiving immunosuppressive therapy including chronic prednisone >10 mg daily.
12. Patients with active or chronic infection other than fungal skin or nail infection or local herpes simplex infection including:
a. History of immunodeficiency diseases, including a positive human immunodeficiency virus (HIV)* (ELISA and Western blot) test result;
b. Chronic infection with Hepatitis B (HBV)* or Hepatitis C (HCV)*. *(These will be tested during the screening period.)
13. Recent surgery (involving entry into a body cavity or requiring sutures) within 2 months of the screening visit or any evidence of unhealed surgical wound or lack of significant recovery from the surgery. (Minor skin surgery is allowed within 2 months of screening provided the surgical wound has healed.)
14. Any surgical or medical condition which might significantly alter the absorption, distribution, metabolism, or excretion of drugs, or which may jeopardize the patient in case of participation in the study. The Investigator should make this determination in consideration of the patient's medical history and/or clinical or laboratory evidence of any of the following:
a. Inflammatory bowel disease, Major gastrointestinal tract surgery such as gastrectomy;
b. Liver disease or liver injury as indicated by abnormal liver function tests defined as: ALT (SGPT) or AST (SGOT) or >2.5× upper limit of normal (ULN); or alkaline phosphatase >2× ULN; or serum bilirubin >2× ULN.

15. History or presence of impaired renal function as indicated by eGFR <60 ml/min/1.73 m2
16. Patients with insulin-dependent diabetes mellitus (Type 1 or 2) or baseline HbA1c>9.0 mg/dL
17. Patients with baseline severe uncontrolled hypercholesterolemia (>350 mg/dL) or hypertriglyceridemia (>500 mg/dL)
18. History of malignancy in any organ system, treated or untreated, within the past 3 years, regardless if there is evidence of local recurrence or metastases, except for localized basal cell or squamous cell carcinoma of the skin.
19. Patients with clinically significant underlying pulmonary disease other than asthma.
20. The following cardiac conditions:
a. Unstable angina pectoris or acute ischemic changes on ECG at screening.
b. History of myocardial infarction, coronary bypass surgery, or any percutaneous coronary intervention (PCI) within 6 months prior to screening.
c. Ventricular arrhythmias except for benign premature ventricular contractions.
d. New York Heart Association functional classification III-IV congestive heart failure.
21. Any other medical condition, as judged by the investigator, that is likely to interfere with the patient's participation in the study, or likely to cause serious adverse events during the study. This includes:
a. Condition(s) that preclude the safe performance of routine lumbar punctures, such as prohibitive spinal diseases, bleeding diathesis, or clinically significant coagulopathy or thrombocytopenia (see exclusion criteria 10 for coagulation parameters and Table 1 for details regarding anti-coagulant and anti-platelet use);
b. A recent (past 12 months) or current history of drug or alcohol abuse.

Further, otherwise eligible patient who met all the above inclusion criteria and are not excluded based on any of the above exclusion criteria will still be excluded from the study based on prohibited concomitant medications, such as:

CYP3A4 or Pgp inducers
rifampin, rifabutin, carbamazepine, phenobarbital, phenytoin, rifapentine CYP3A4 or Pgp inhibitors
ketoconazole, voriconazole, itraconazole, erythromycin, telithromycin, clarithromycin, bromocriptine, cimetidine, cisapride, clotrimazole, diltiazem, danazol, fluconazole, protease inhibitors, metoclopramide, nicardipine, troleandomycine, verapamil Anti-coagulants
e.g., coumadin, warfarin, heparin and new oral anticoagulants (NOACS, e.g., dabigatran, rivaroxaban, apixaban; Patients on NOACS may be included only if the investigator and patient agree that the NOAC medication can be safely withheld for 1 day prior to and on the day of the performance of the lumbar puncture procedures at visits XX and YY)

Anti-platelet agents
e.g., clopidogrel, ticlodipine (Patients on aspirin may be included. Patients on other anti-platelet agents may be included only if the investigator and patient agree that the anti-platelet agent can be safely withheld for 1 week prior to and on the day of performance of the lumbar puncture procedures at visits XX and YY)

Foods or supplements e.g., grapefruit or seville oranges or their juices, St. John's Wort (hypericum perforatum)

Other agents/treatments

Live vaccines (e.g., measles, mumps, rubella, oral polio, BCG, yellow fever, varicella, and TY21a typhoid)

The assessment schedule for the study are summarized in Table 10, below.

| Objectives and Related Endpoints | |
|---|---|
| Objectives | Endpoints |
| Primary Objective | Endpoint for Primary Objective |
| To determine the safety and tolerability of orally-administered RTB101 or sirolimus alone or in combination as compared to placebo in patients with GBA PD. | Physical exam, body weight, respiratory rate, body temperature, blood pressure, pulse rate, ECG evaluation, hematology, blood chemistry, urinalysis, coagulation, lipid profile, glucose (serum), HbA1c, adverse events, serious adverse events, etc. |
| Secondary Objectives | Endpoints for Secondary Objectives |
| To assess the blood and plasma pharmacokinetic (PK) profile of oral dosing of RTB101 or sirolimus alone or in combination when administered once weekly to GBA-PD patients. | PK draw |
| To assess cerebrospinal fluid (CSF) concentrations of RTB101 and sirolimus given alone or in combination after oral administration once weekly in GBA-PD patients. | CSF draw |
| Exploratory Objectives | Endpoints for Exploratory Objectives |
| Changes from baseline to Week 12 in plasma and CSF levels of lyso-glucosylceramide (GL1).<br>Changes from baseline to Week 12 in plasma and CSF levels of α-synuclein (α-syn).<br>Changes from baseline to Week 12 in plasma and CSF levels of neurofilament light chain (NfL), neurofilament heavy chain (NfH), phosphor tau, and beta amyloid.<br>Change from baseline to Week 12 in Timed Up and Go Test.<br>Changes from baseline to Week 12 in Modified Hoehn & Yahr stage<br>Change from baseline to Week 12 in Montreal Cognitive Assessment.<br>Change from baseline to Week 12 in the Unified Parkinson's Disease Rating Scale (UPDRS, Part 1-4, total score) for those patients who are in "ON state" at baseline and week 12 visits.<br>Change from baseline to Week 12 in Parkinson's Disease Quality of Life-39 (PDQ-39) score<br>Change in measures of sleep from baseline to Week 12 in Epworth Sleepiness Scale (ESS)<br>Change from baseline to Week 12 in total levodopa equivalent dose (LED) for those patients on dopaminergic therapies<br>Change from baseline to Week 12 in motor function and sleep function (e.g., bradykinesia, dyskinesia, tremor) assessed with a wearable device (e.g., PKG™ System, Global Kinetics Corp) | Confirmation of safety and tolerability over longer periods of treatment and more chronic PK and efficacy. |

Study Design

This multicenter, randomized, double-blind, placebo-controlled study will be to determine the safety and tolerability of RTB101 and sirolimus, alone or in combination, when administered once weekly to GBA-PD patients. The study will be composed of up to about a four (4) week screening period (i.e., twenty-eight (28) days), a baseline assessment, up to about twelve (12) weeks of treatment, and about a one (1) week follow-up period. The assessment schedule for the study is summarized in FIG. 4, FIG. 5A and FIG. 5B.

Study Period: The total planned duration of the study for each subject is up to twelve (12) weeks.

Screening Period: Screening may occur prior to investigational product being available onsite. During the screening, patients will be assessed for eligibility to participate in the study based on inclusion/exclusion criteria.

Figure 6:
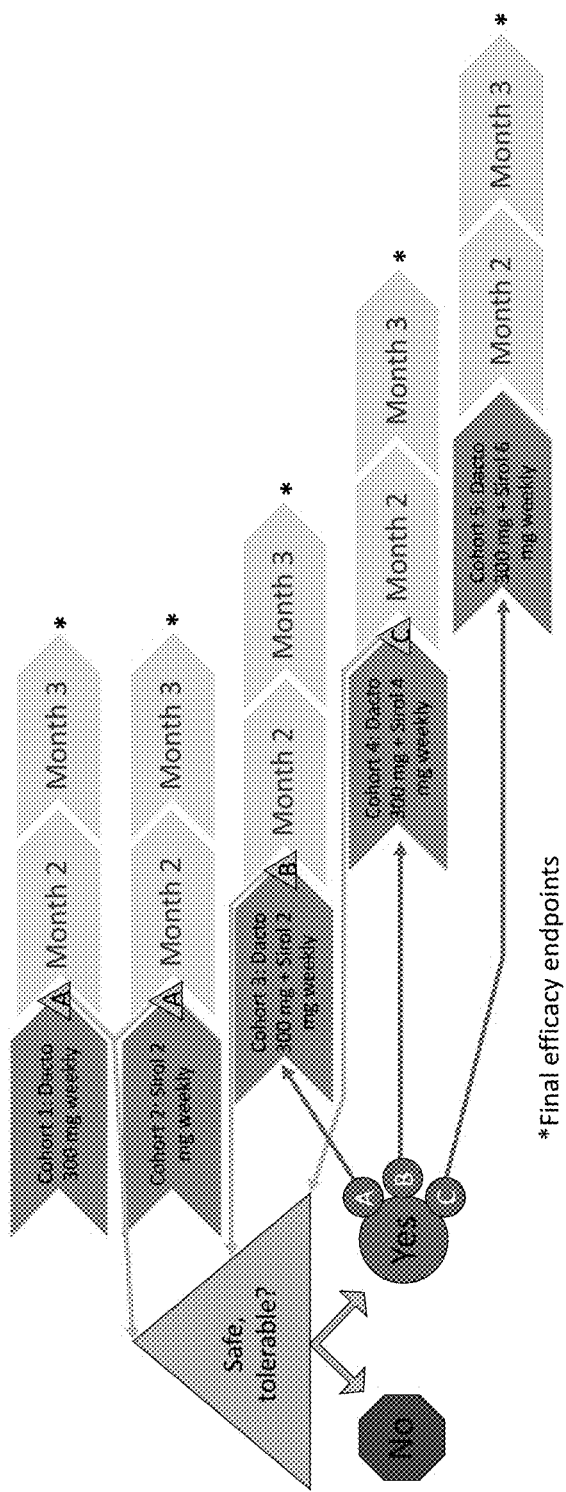
FIG. 6 shows the Example 6 clinical study design for RTB101 in combination with sirolimus for treatment of patients with glucocerebrosidase gene mutation-associated Parkinson's disease.
Figure 7:
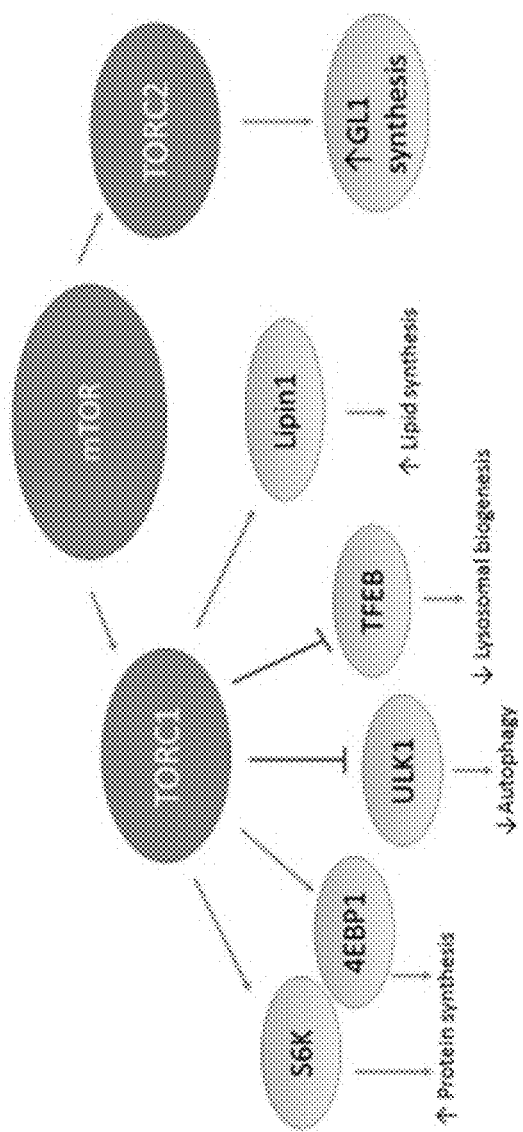
FIG. 7 shows the downstream targets of the mTOR pathway and the impact on Parkinson's disease pathogenesis.
Figure 8:
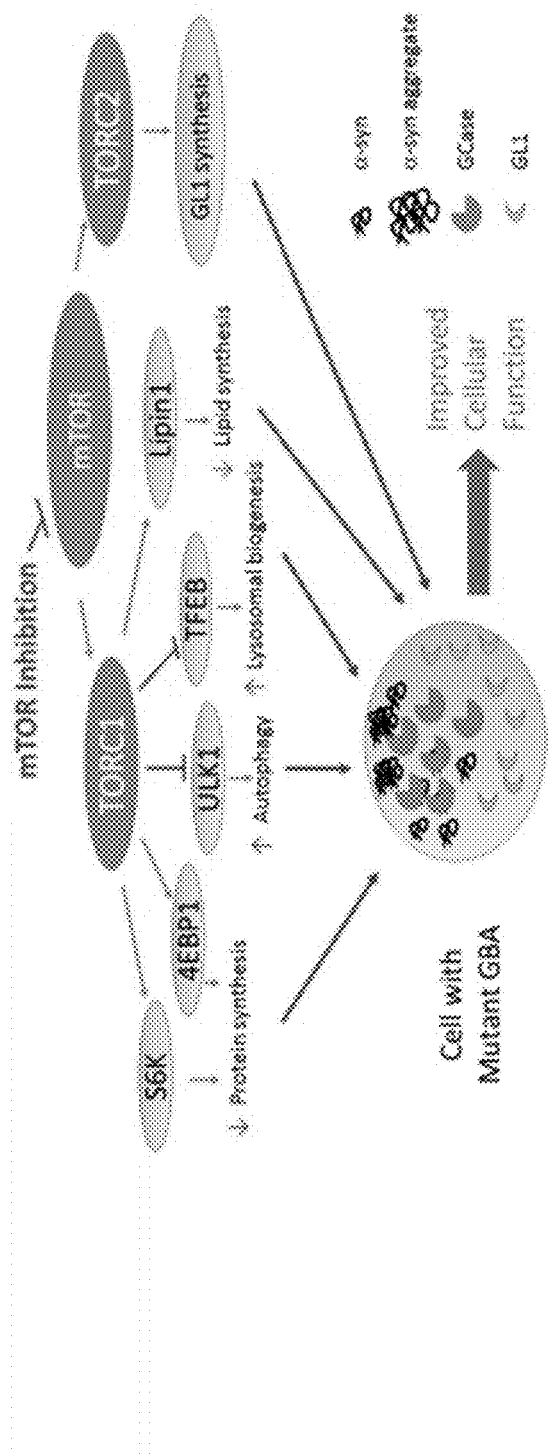
FIG. 8 shows the potential benefits of broad mTOR inhibition in GBA-PD.

Treatment Period: Patients will be randomized into one (1) or five (5) cohorts. Approximately sixty (60) persons will be enrolled in the study. Each cohort will comprise nine (9) patients, allowing the replacement of up to fifteen (15) persons. Cohorts 1 and 2 will be enrolled in parallel. Dose escalation cohorts will be enrolled sequentially. Prior to escalation to the next cohort, safety and PK will be assessed when six (6) patients in the active treatment arm cohort have completed twenty-eight (28) days of dosing. RTB101 drug substance will be administered as 100 mg hard gelatin capsules; sirolimus drug substance will be administered as the commercially available 2 mg tablets (e.g., available from Dr. Reddy's Lab). The study design is summarized in FIG. 6.

Cohort 1: RTB101 monotherapy—patients will be randomized 2:1 to RTB101 300 mg or placebo equivalent given orally once per week for up to 12 weeks.

Cohort 2: sirolimus monotherapy—patients will be randomized 2:1 to sirolimus 2 mg or placebo equivalent given orally once per week for up to 12 weeks.

Cohort 3: RTB101+sirolimus combination Dose 1—patients will be randomized 2:1 to RTB101 300 mg+sirolimus 2 mg or placebo equivalent given orally once per week for up to 12 weeks.

Cohort 4: RTB101+sirolimus combination Dose 2—patients will be randomized 2:1 to RTB101 300 mg+sirolimus 4 mg or placebo equivalent given orally once per week for up to 12 weeks.

Cohort 5: RTB101+sirolimus combination Dose 3—patients will be randomized 2:1 to RTB101 300 mg+sirolimus 6 mg or placebo equivalent given orally once per week for up to 12 weeks.

Rationale for Study Design: The design of this study addresses the primary objective of determining the safety and tolerability of RTB101 and sirolimus, alone or in combination, in patients with GBA PD. The study is a randomized, double-blinded placebo-controlled, study to obtain efficacy, tolerability and safety data in an unbiased fashion.

Study Population: The study will enroll adults with GBA PD, who are not otherwise excluded from eligibility.

Primary Endpoint: The primary endpoint of the study is to determine the safety and tolerability of orally-administered RTB101 and sirolimus, alone or in combination, as compared to placebo in patients with GBA PD.

Secondary and Exploratory Endpoints: The secondary and exploratory endpoints are to confirm the safety and tolerability of RTB101 and sirolimus, alone or in combination, over longer periods of treatment and to obtain PK and other exploratory efficacy data.

Rationale for Dose/regimen, Route of Administration, and Duration of Treatment: The dosages and administration schedule for RTB101 and sirolimus are selected to maintain efficacious concentrations while reducing chronic exposure. A single dose level (300 mg weekly) of RTB101 is chosen based on 1) the minimum dose predicted to consistently give efficacious brain exposures, 2) a ≥2-fold safety margin below the weekly cumulative MTD of RTB101 administered with another rapalog, everolimus, and 3) weekly dosing based on targeted biology and maximizing safety. Dose escalation of sirolimus will allow assessment of safety and tolerability across the range of currently approved doses of sirolimus (2-6 mg) when sirolimus is combined with RTB101.

Example 7

Figure 10:
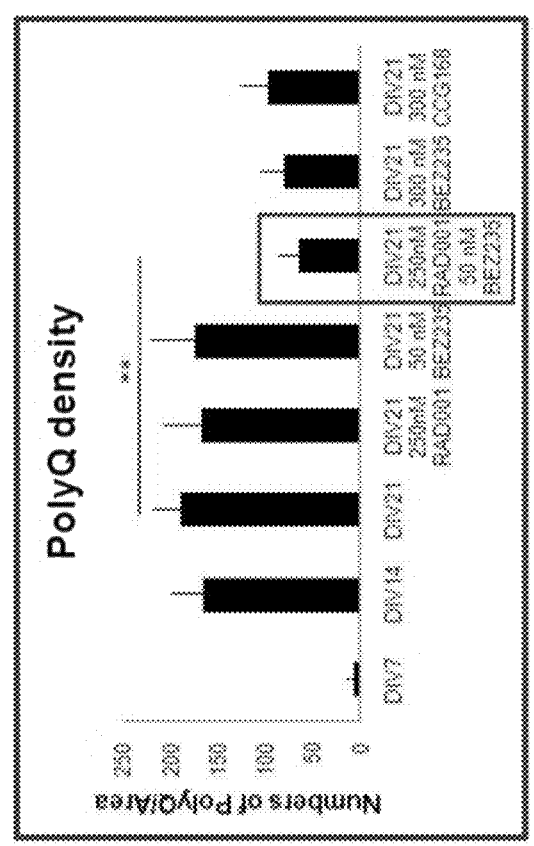
FIG. 10 shows that everolimus/RTB101 or CCG168 combination reduces polyQ inclusions in R6/2 brain slices. Quantification of the polyQ density from DIV7 to DIV21 and under different treatments at DIV21. The combination of everolimus/RTB101 reduced the polyQ density compared to the DIV21 R6/2 DMSO treated slices, whereas 250 nM everolimus and 50 nM RTB101 single concentrations showed no effect. The combination of everolimus/CCG168 also reduced the polyQ density compared to the DIV21 R6/2 DMSO treated slices.

Low-dose Combination of Everolimus and RTB101 or CCG168 Induces Autophagy in R6/2 Brain Slices To investigate whether the combination of everolimus/RTB101 could work synergistically in reducing polyQ inclusions, the polyQ density of treated R6/2 slices at DIV21 was measured by comparing the immunohistochemical detection of PolyQ inclusions and nuclei in R6/2 slices. Slices treated with 250 nM everolimus or 50 nM RTB101 exhibited a similar polyQ distribution compared to control R6/2, whereas the combination of everolimus/RTB101 reduced the polyQ density. It was observed that single low-concentrations of everolimus and RTB101 did not reduce polyQ inclusions, whereas the combination had a significant effect and reduced the polyQ density compared to R6/2 slices. In addition, the effective single concentration of 300 nM RTB101 lead to a similar decrease, suggesting that RTB101 together with everolimus worked synergistically in reducing polyQ density. FIG. 10.

Figure 11:
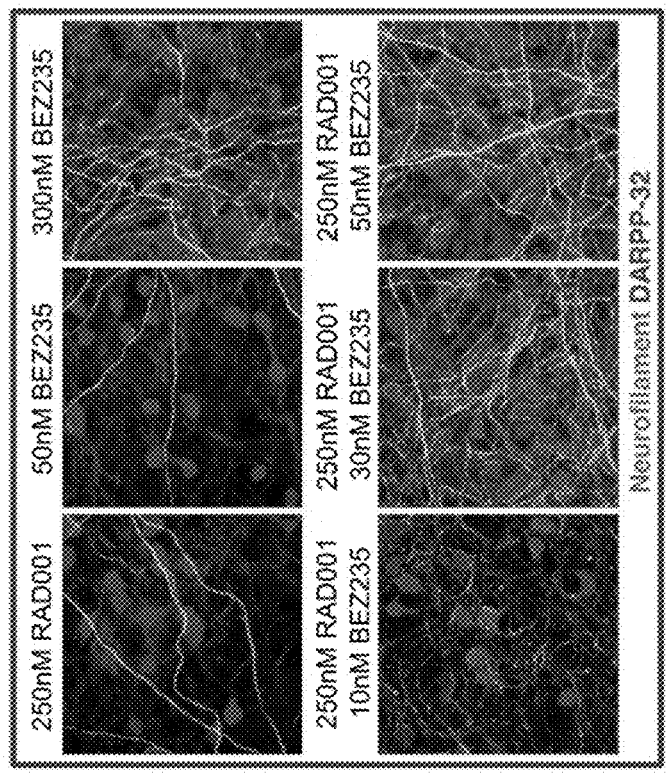
FIG. 11 shows that the everolimus/RTB101 combination prevents striatal degeneration in R6/2 brain slices as assessed by quantitative analysis of DARPP-32 intensity and neurofilament levels. The combination of everolimus/RTB101 preserved the DARPP-32 level compared to control R6/2 slices. The combination of everolimus/RTB101 preserved the neurofilament level compared to control R6/2 slices.

To assess whether the combination of everolimus/RTB101 could preserve synergistically the ongoing striatal degeneration, DARPP-32 and neurofilament stainings at DIV21 were analyzed by immunohistochemical detection of DARPP-32 and neurofilament in WT and R6/2 slices. Single low-concentrations of everolimus and RTB101 were ineffective in preserving DARPP-32 and neurofilament levels. However, the combination preserved the neurofilament level and the DARPP-32 level. 250 nM everolimus/30 nM RTB101 was the lowest effective combinatorial concentration. FIG. 11.

Slice cultures were established according to described procedures. (L. Stoppini et al., J. Neurosci. Methods 37(2): 173-82 (1991) and N. Gogolla et al., Nat. Protoc. 1(3): 1165-71 (2006)). A particular cutting angle was utilized to produce brain slices with a preserved cortico-striatal pathway. Finally, slices were selected, placed on Millicel (Millipore, PICM03050) and cultured in 6-well dishes at 35° C. and 5% $CO_2$ in the presence of 1 ml of culture medium.

Slices were treated with different mTOR inhibitors from DIV14 to DIV21. The culture medium was exchanged every second day, and drugs were added in the fresh culture medium. We used this protocol to evaluate the action of the following mTOR inhibitors: RTB101 (50 and 300 nM in DMSO), everolimus (250 nM in DMSO), CCG168 (300 nM in DMSO), and everolimus+RTB101 (250 and 10, 250and 30 and 250 and 50 nM in DMSO).

Slices were washed in PBS and lysed in 1% Triton X-100/PBS containing Complete Mini (Roche, #04693124001) and PhosSTOP (Roche, #04906837001). Lysates were ultrasonicated and analyzed by Western blotting for B-actin (Sigma, #A5441), pS6 Ser 240/244 (Cell Signalling, #2215), and LC3B (Cell Signalling, #2775). Immunoblots were developed with ECL detection reagent (Amersham Biosciences).

Slices were fixed for 10 minutes in 4% PFA, washed in PBS and blocked for 4 hr at room temperature in 0.3% Triton X-100 20% Horse Serum/PBS (blocking solution). Antibodies for DARPP-32 (Cell Signaling, #2306S, 1:200), neurofilament (NeuF, Developmental Studies Hybridoma Bank, University of Iowa; #2H3, 1:200) and EM48 (Millipore, #MAB5374, 1:200) were incubated for 48 hr at 4° C. in the blocking solution. Afterwards, slices were washed in PBS, incubated for 2 hrs in 0.3% Triton X-100/PBS with Alexa 488 (Invitrogen, 1:500) and Alexa 555 (Invitrogen, 1:500)

conjugated secondary antibodies. Finally, slices were washed in PBS, incubated 10 minutes with DAPI (Invitrogen, #D1306 1:10000) and embedded on glass dishes using ProLong (Invitrogen, #P36934).

High resolution images were acquired on an upright Zeiss LSM700 confocal microscope, using a Plan-Neofluar 40x/1.3 oil immersion objective. For the quantification of the PolyQ density and DARPP-32/NeuF signal intensity, at least three confocal 3D stacks/slice were acquired in striatum for each experiment (five slices per condition), and analyzed using Imaris 4.2 (BitplaneAG) and Image J softwares. All data are expressed as mean±SEM. Statistical analysis was performed by analysis of variance (ANOVA) followed by a Student's t Test (Excel, Microsoft, USA). The significance level was set at p<0.05.

Example 8

Combination of Sirolimus and RTB101 for Treatment of Patients with Parkinson's Disease A total of approximately sixty (60) persons having mild Parkinson's disease (PD) will be enrolled in a multicenter, double blind, placebo-controlled trial to assess the safety, tolerability, and central nervous system (CNS) exposure of oral RTB101 and sirolimus, alone or in combination, as compared to placebo. The study will be comprised of adult males and females who exhibit mild PD, i.e., modified Hoehn and Yahr (mH&Y) stage ≤2.

Patients will be randomly assigned to one of five (5) cohorts to assess the safety, tolerability, and efficacy of sirolimus and RTB101, alone on in combination. The treatment arms in each cohort are as follows:

Cohort 1: Randomized 2:1(RTB101: Placebo)
  RTB101 300 mg (3 capsules of 100 mg)
  Matching Placebo (3 capsules of 100 mg RTB101 matching placebo)
Cohort 2: Randomized 2:1(sirolimus: Placebo)
  sirolimus 2 mg (1 tablet of 2 mg)
  Matching Placebo (1 tablet of 2 mg sirolimus matching placebo)
Cohort 3: Randomized 2:1(RTB101 300 mg+sirolimus 2 mg: Placebo)
  RTB101 300 mg (3 capsules of 100 mg) AND sirolimus 2 mg (1 tablet of 2 mg)
  Matching Placebos (3 capsules of 100 mg RTB101 matching placebo AND 1 tablet of 2 mg sirolimus matching placebo)
Cohort 4: Randomized 2:1(RTB101 300 mg+sirolimus 4 mg: Placebo)
  RTB101 300 mg (3 capsules of 100 mg) AND sirolimus 2 mg (2 tablets of 2 mg)
  Matching Placebos (3 capsules of 100 mg RTB101 matching placebo AND 2 tablets of 2 mg sirolimus matching placebo)
Cohort 5: Randomized 2:1(RTB101 300 mg+sirolimus 6 mg: Placebo)
  RTB101 300 mg (3 capsules of 100 mg) AND sirolimus 2 mg (3 tablets of 2 mg)
  Matching Placebos (3 capsules of 100 mg RTB101 matching placebo AND 3 tablets of 2 mg sirolimus matching placebo)

The RTB101 and sirolimus monotherapy cohorts (Cohorts 1 and 2) may be dosed in parallel. The combination cohorts (Cohorts 3-5) will be dosed in a sequential fashion (see FIG. 3). After a minimum of 7 patients within a cohort complete one month of dosing, safety and tolerability will be assessed before dosing will commence in the subsequent cohorts (Cohorts 3-5).

Safety and Tolerability

Continuous safety data will be summarized with descriptive statistics (arithmetic mean, SD, median, minimum, and maximum) by dose level. Categorical safety data will be summarized with frequency counts and percentages by dose level. Adverse events (AE) will be coded using the most current Medical Dictionary for Regulatory Activities (MedDRA®) available. A by-participant AE data listing, including verbatim term, preferred term, system organ class, treatment, severity, and relationship to study drug will be provided. The number of participants experiencing treatment emergent AEs (TEAEs) and number of individual TEAEs will be summarized by treatment group, system organ class, and preferred term. TEAE's will also be summarized by severity and by relationship to study drug.

Laboratory evaluations and vital signs assessments will be summarized by Cohort and protocol specified collection time point. A summary of change-from-baseline at each protocol specified time point by Cohort will also be presented.

Pharmacokinetic Evaluations

The analysis will be conducted with mixed-effects (population) methods. A dataset suitable for the analysis will be constructing using R (r-project.org, version 3.3.2 or later). One- and two-compartment linear models with first-order absorption and first-order elimination will be evaluated initially. A systemic search will then be applied to determine the impact of covariates (age, body size, gender, race, drug-drug interactions, organ function) on the pharmacokinetic parameters, focusing on apparent clearance and absorption rate. Once a final model is determined, model validation will include some combination of visual predictive check (with and without prediction-correct), likelihood profiles, and bootstrap analyses.

Patient Selection

Patients will be subjected to extensive screening prior to inclusion in the study. To be eligible for inclusion in the study, a patient must fulfill all of the following:

Inclusion Criteria:
 1. Patient must be able to communicate well with the investigator, and to understand and comply with the requirements of the study.
 2. Signed informed consent must be obtained before any study assessment is performed.
 3. Male and female adults ≥18 years of age at the time of informed consent signing.
 4. Patients must weigh ≥40 kg and ≤150 kg at the Baseline Visit.
 5. Diagnosis of Parkinson's Disease with a Modified Hoehn and Yahr stage of ≤2 at screening.
 6. Stable medication regimen of PD drugs for at least 30 days (at least 60 days for rasagiline) prior to first dose (Day 0, Visit 3).
 7. At screening and baseline, vital signs (systolic and diastolic blood pressure, pulse rate and respiratory rate) will be assessed in a sitting position after the patient has rested for at least three (3) minutes. Sitting vital signs should be within the following ranges:
   a. Oral or tympanic body temperature between 35.0-37.5° C.
   b. Systolic blood pressure, 90-160 mm Hg
   c. Diastolic blood pressure, 50-95 mm Hg
   d. Heart Rate, 40-95 bpm If vital signs are outside these ranges, the Investigator may obtain up to two additional readings, so that up to 3 consecutive assessments are made. Patients must be within the ranges provides above at the Baseline Bisit in order for the patient to be eligible for the study.

Otherwise eligible patient will be excluded from the study for any of the following:

Exclusion Criteria:
1. Parkinsonism due to drug(s) or toxin(s); or those patients with a history of a prior brain MRI showing a structural abnormality that is a possible cause of their PD signs or symptoms; patients with previously diagnosed Gaucher's disease (with homozygous glucocerebrosidase (GBA) mutations) are excluded; patients with previously diagnosed heterozygous GBA mutations are NOT excluded.
2. Patients with prior surgical history of deep brain stimulation (DBS).
3. If female, pregnancy (defined as positive beta-human chorionic gonadotrophin [Beta-hCG] blood test) or lactating or breast-feeding.
4. Women of childbearing potential (any woman physiologically capable of becoming pregnant) unless they remain on highly effective methods of contraception (see below) throughout the study and for 12 weeks following discontinuation of the study drug.
   Women are considered post-menopausal and not of child bearing potential if:
   a. They have had 12 months of natural (spontaneous) amenorrhea with an appropriate clinical profile (e.g., age appropriate, history of vasomotor symptoms) or;
   b. They have had surgical bilateral oophorectomy (with or without hysterectomy), total hysterectomy or tubal ligation at least six weeks ago. In the case of oophorectomy alone, only when the reproductive status of the woman has been confirmed by follow-up hormone level assessment is she considered not of child bearing potential
   This study drug may impact the effectiveness of hormonal contraceptives therefore hormonal contraceptives should not be relied on as an effective method of contraception. Highly effective contraception methods include:
   a. Total abstinence (when this is in line with the preferred and usual lifestyle of the patient. Periodic abstinence (i.e., calendar, ovulation, symptothermal, postovulation methods) and withdrawal are not acceptable methods of contraception.
   b. Female sterilization (have had surgical bilateral oophorectomy (with or without hysterectomy), total hysterectomy or tubal ligation at least six weeks prior to the first dose (Day 0)). In case of oophorectomy alone, only when the reproductive status of the woman has been confirmed by follow up hormone level assessment.
5. Male condoms: sexually active male patients with a partner of child-bearing potential must be willing to wear a condom while on study drug and for 12 weeks after stopping study drug and should not father a child in this period. A condom is required to be used also by vasectomized men with a partner of child-bearing potential to prevent delivery of the drug via seminal fluid.
6. Use of other investigational drugs within 5 half-lives of randomization, or within 30 days, whichever is longer; or longer if required by local regulations.
7. History of hypersensitivity or allergy to sirolimus, RTB101 or their excipients or to other mTOR inhibitor drugs.
8. Concomitant use of any of the drugs (including strong cytochrome P450 enzyme (CYP)3A4 inhibitors or inducers), angiotensin converting enzyme inhibitors, and anti-coagulants) or other treatments (including live vaccines).
9. Any one of the following hematologic or coagulation abnormalities at screening:
   hemoglobin <10.0 g/dL for males and <9.0 g/dL for females;
   white blood cell (WBC) count <3,500/mm3;
   neutrophil count <2,000/mm3;
   platelet count <125,000/mm3;
   international normalized ratio (INR) >1.2; or,
   partial prothromboplastin time (PTT) >35 seconds.
10. Patients receiving immunosuppressive therapy including chronic prednisone >10 mg daily.
11. Patients with active or chronic infection other than fungal skin or nail infection or local herpes simplex infection.
12. Immunodeficiency diseases, including a positive human immunodeficiency virus (HIV)* test result; or chronic infection with Hepatitis B virus (HBV)* or Hepatitis C (HCV)*.
   *(These will be tested during the screening period.)
13. Recent surgery (involving entry into a body cavity or requiring sutures) within 2 months of the Screening Visit or any evidence of unhealed surgical wound or lack of significant recovery from the surgery. (Minor skin surgery is allowed within 2 months of screening provided the surgical wound has healed.)
13. Any surgical or medical condition which might significantly alter the absorption, distribution, metabolism, or excretion of drugs, or which may jeopardize the patient in case of participation in the study. This includes clinical or laboratory evidence of:
   a. Inflammatory bowel disease, Major gastrointestinal (GI) tract surgery such as gastrectomy;
   b. Liver disease or liver injury as indicated by abnormal liver function tests defined as:
      alanine aminotransferase (ALT) (SGPT) or aspartate aminotransferase (AST) (SGOT) or >2.5× upper limit of normal (ULN); or
      alkaline phosphatase (ALP) >2× ULN; or
      serum bilirubin >2× ULN.
14. History or presence of impaired renal function as indicated by estimated glomerular filtration rate (eGFR) <60 ml/min/1.73 m$^2$
15. Patients with insulin-dependent diabetes mellitus (Type 1 or 2) or screening hemoglobin A1C (HbA1c) >9.0 mg/dL
16. Patients with baseline severe uncontrolled hypercholesterolemia (fasting low-density lipoprotein [LDL] cholesterol >150 mg/dL) or hypertriglyceridemia (fasting triglycerides (TG) >500 mg/dL) at screening. Note: If initial screening values are from a blood sample drawn when the patient was not fasting, test may be repeated, and fasting values may be used for eligibility if they do not meet this exclusion criteria.
17. History of malignancy in any organ system, treated or untreated, within the past 3 years, regardless if there is evidence of local recurrence or metastases, except for: treated localized basal cell carcinoma of the skin;
   prostate cancer confined to the gland (AJCC Stage T2N0M0 or better);

treated cervical carcinoma in situ;
treated breast cancer localized to the breast.
18. Patients with clinically significant underlying pulmonary disease other than asthma.
19. The following cardiac conditions:
   a. Unstable angina pectoris or acute ischemic changes on electrocardiogram (ECG) at Screening.
   b. History of myocardial infarction, coronary bypass surgery, or any percutaneous coronary intervention (PCI) within 6 months prior to Screening.
   c. Ventricular arrhythmias except for benign premature ventricular contractions.
   d. New York Heart Association functional classification III-IV congestive heart failure.
20. Any other medical condition, as judged by the investigator, that is likely to interfere with the patient's participation in the study, or likely to cause serious adverse events during the study. This includes: condition(s) that preclude the safe performance of routine lumbar punctures, such as prohibitive spinal diseases, bleeding diathesis, or clinically significant coagulopathy (includeing being required to take anticoagulents) or thrombocytopenia Further, otherwise eligible patient who met all the above inclusion criteria and are not excluded based on any of the above exclusion criteria will still be excluded from the study based on prohibited concomitant medications, such as those in Table 10, below. The period for which the prohibited medications are prohibited are summarized in Table 11, below.

TABLE 10

Prohibited Concomitant Medications

| Mechanism | Drugs with Strong Effects | Drugs with Moderate Effects |
|---|---|---|
| CYP3A4 or P-gp inducers | avasimibe<br>carbamazipine<br>phenobarbital<br>phenytoin<br>rifabutin<br>rifampin<br>rifapentine | bosentan<br>modafinil<br>nafcillin<br>pioglitazone |

TABLE 10-continued

Prohibited Concomitant Medications

| Mechanism | Drugs with Strong Effects | Drugs with Moderate Effects |
|---|---|---|
| CYP3A4 or P-gp inhibitors | bromocriptine<br>cisapride<br>clarithromycin<br>clotrimazole<br>conivaptan<br>danazol<br>itraconazole<br>ketoconazole<br>metoclopramide<br>nefazodone<br>nicardipine<br>pozaconazole<br>protease inhibitors†<br>telithromycin<br>voriconazole | aprepitant<br>cimetidine<br>ciprofloxacin<br>diltiazem<br>erythromycin<br>fluconazole<br>tofisopam<br>verapamil<br>"statins"¶ |
| Anti-coagulants | including coumadin, warfarin, heparin and new oral anti-coagulants (‡NOACS, e.g. dabigatran, rivaroxaban, apixaban) | |
| Anti-platelet agents§ | including clopidogrel, ticlodipine | |
| Foods or supplements | grapefruit or grapefruit juice<br>St. John's Wort (*hypericum perforatum*)<br>Shisandra (Chinese "five-flavor fruit") | |
| Other agents/treatments | Angiotensin converting enzyme (ACE) inhibitors, live vaccines (including but not limited to: measles, mumps, rubella, oral polio, BCG, yellow fever, varicella, and TY21a typhoid) | |

ACE = angiotensin converting enzyme;
CYP = cytochrome P450 enzyme;
NOACS = new oral anti-coagulants;
P-gp = P-glycoprotein;
†Protease inhibitors include: boceprevir, indinavir, lopinavir, nelfinavir, ritonavir, saquinavir, ritonavir, tipranavir, atazanavir, darunavir, fosamprinivir, tipranivir;
‡Patients on NOACS may be included only if the Investigator and patient agree that the NOAC medication can be safely withheld for 3 days prior to and 1 day following the performance of the lumbar puncture procedures at Baseline Visit and Week 3;
§Patients on aspirin may be included. Patients on other anti-platelet agents may be included only if the Investigator and patient agree that the anti-platelet agent can be safely withheld for 2 weeks prior to and 1 day following the performance of the lumbar puncture procedures at Baseline Visit and Week 3;
¶Patients on "statins" (HMG-CoA reductase inhibitors) other than rosuvastatin should be switched to rosuvastatin if possible. If this is not possible, the patient may only be included if the investigator and patient agree that the statin medication may be safely withheld for ≥2 weeks prior to the first dose of study drug (Day 0 Visit) and throughout the remainder of the study (through End of Study Visit).

TABLE 11

Prohibited Medication Instructions

| Medication* | Prohibition Period | Action to be Taken if Prohibited Medication is Required During Study |
|---|---|---|
| Moderate-strong inhibitors or inducers of CYP3A4 or P-gp | From 1 week prior to Baseline Visit through End of Study Visit (Week 4) | Discontinue study treatment and contact sponsor. |
| Grapefruit or Seville oranges or their juices | From 1 week prior to Baseline Visit through End of Study Visit (Week 4) | Discontinue study treatment and contact sponsor. |
| Live vaccines (including but not limited to: measles, mumps, rubella, oral polio, BCG, yellow fever, varicella, and TY21a typhoid) | From 1 week prior to Baseline visit through End of Study Visit (Week 4) | Discontinue study treatment and contact sponsor. |
| Anti-coagulants: NOACS† | 3 days prior to and 1 day following the day of the lumbar puncture at Baseline Visit and Week 3 Visit. | Do not perform lumbar puncture. Patient is excluded from study if medication is required at time of Baseline Visit. Contact sponsor if patient requires medication after the Baseline Visit through the Week 3 Visit. |
| Anti-coagulants: Warfarin and other vitamin K antagonists | Not permitted within 30 days before or 3 days following lumbar | Do not perform lumbar puncture. Patient is excluded from study if medication is required at time of Baseline Visit. Contact |

TABLE 11-continued

Prohibited Medication Instructions

| Medication* | Prohibition Period | Action to be Taken if Prohibited Medication is Required During Study |
|---|---|---|
| | punctures at the Baseline Visit and Week 3 Visit. | sponsor if patient requires medication after the Baseline Visit through the Week 3 Visit. |
| Anti-coagulants (injectable) including: heparin, enoxaparin, fondaparinux | Not permitted within 2 days prior to and 1 day following lumbar punctures at the Baseline Visit and Week 3 Visit. | Do not perform lumbar puncture. Patient is excluded from study if medication is required at time of the Baseline Visit. Contact sponsor if patient requires medication after the Baseline Visit through the Week 3 Visit. |
| Anti-platelet agents‡ | Not permitted within 2 days prior to and 1 day following lumbar punctures at the Baseline Visit and Week 3 Visit. | Do not perform lumbar puncture. Patient is excluded from study if medication is required at time of the Baseline Visit. Contact sponsor if patient requires medication after the Baseline Visit through the Week 3 Visit. |
| Aspirin | None | N/A |

CYP = cytochrome P450 enzyme;
N/A = not applicable'
NOACS = new oral anti-coagulants;
P-gp = P-glycoprotein;
*Additional information and recommendations regarding use of anti-coagulants and anti-platelet agents in the setting of lumbar puncture may be found in R. Domingues et al. "Lumbar puncture in patients using anticoagulants and antiplatelet agents." *Arq Neuropsiquiatr 74*, pp. 679-86 (2016);
†NOACS include: rivaroxaban, dabigatran, edoxaban, apixaban;
‡Anti-platelet agents (not including aspirin, see separate listing above) include: clopidogrel, ticagrelor, prasugrel, dipyridamole, ticlodipine, eptifibatide (and other glycoprotein IIb/IIIa receptor antagonists).

| Objectives and Related Endpoints | |
|---|---|
| Objectives | Endpoints |
| Primary Objective | Endpoint for Primary Objective |
| To determine the safety and tolerability of orally-administered RTB101 or sirolimus alone or in combination as compared to placebo in patients with PD. | Percentage of patent experiencing one of more TEAEs in the treatment arms compared to the placebo arms. Any significant relationship between PK exposure of RTB101 and/or sirolimus and clinically significant changes in clinical laboratory values or other clinical parameters (e.g., vital signs) from the Baseline value. |
| Secondary Objectives | Endpoints for Secondary Objectives |
| To assess the blood and plasma pharmacokinetic (PK) profile of oral dosing of RTB101 or sirolimus alone or in combination when administered once weekly to PD patients. To assess cerebrospinal fluid (CSF) concentrations of RTB101 and sirolimus given alone or in combination after oral administration once weekly in PD patients. | AUCs and $C_{max}$ will be assessed in each cohort in blood and plasma. Single time point drug concentrations at one month of weekly exposure will be assessed in CSF and compared to blood and plasma collected contemporaneously at $T_{max}$. The relationship between covariates (e.g., body size, age, gender, race, organ function) and systemic or CSF exposure of RTB101 and sirolimus will be assessed. |
| Exploratory Objectives | Endpoints for Exploratory Objectives |
| To assess effects of RTB101 and sirolimus alone or in combination on biomarkers (clinical and laboratory) of clinical disease status in PD patients, | Changes from baseline to Week 3 in plasma and CSF levels of lyso-glucosylceramide (GL1). Changes from baseline to Week 3 in plasma and CSF levels of α-synuclein (α-syn). Changes from baseline to Week 3 in plasma and CSF levels of neurofilament light chain (NfL), neurofilament heavy chain (NfH), phosphor tau, and beta amyloid. Change from baseline to Week 4 in the Unified Parkinson's Disease Rating Scale (UPDRS, Part 1-4, total score) for those patients who are in "ON state" at baseline |

| Objectives and Related Endpoints | |
| --- | --- |
| Objectives | Endpoints |
| | and week 4 visits. Change from baseline to Week 4 in Parkinson's Disease Quality of Life-39 (PDQ-39) score Change in measures of sleep from baseline to Week 4 in Epworth Sleepiness Scale (ESS) Change from baseline to Week 4 in total levodopa equivalent dose (LED) for those patients on dopaminergic therapies Change from baseline to Week 4 in motor function and sleep function (e.g., bradykinesia, dyskinesia, tremor) assessed with a wearable device (e.g., PKGTM System, Global Kinetics Corp) |

An overview of the biomarker strategy is summarized in Table 12, below.

TABLE 12

Overview of Biomarker Strategy

| Assessment/Biomarker | Type | Putative meaning/comments |
| --- | --- | --- |
| Lyso-glucosylceramide (lyso-GL1) | Plasma & CSF | Biomarkers in patients with Gaucher's disease (homozygous GBA mutation); preclinical data supports changes predict neurologic improvement |
| α-Synuclein (α-syn) | Plasma & CSF | Putative causal toxic protein may be cleared by mTOR inhibition and activation of autophagy, mixed results correlating with PD clinical parameters |
| Neurofilament light and heavy chains (NfL, NfH) | Plasma & CSF | Elevated in other neurodegenerative diseases, mixed results in PD |
| Total and phosphorylated Tau & β-amyloid proteins | Plasma & CSF | Studied extensively in Alzheimer's disease, may serve as correlative negative biomarker in PD |
| Modified Hoehn & Yahr stage (mH&Y) | Clinical assessment | Most commonly used clinical disease staging tool |
| Unified Parkinson's Disease Rating Scale (UPDRS) | Clinical assessment | More global assessment of disease status |
| Parkinson's disease quality of life questionnaire (PDQ-39) | Clinical assessment | Most commonly used metric for patient-reported health status across multiple dimensions |
| Epworth sleepiness scale (ESS) | Clinical assessment | Recommended assessment of clinically relevant sleep disorders |
| Outpatient assessment of motor and sleep function | Wearable device | Assessment of outpatient function over 5-10 days |

Study Design

This multicenter, randomized, double-blind, placebo-controlled study will be to determine the safety and tolerability of RTB101 and sirolimus, alone or in combination, when administered once weekly to PD patients. The study will be composed of up to about a three (3) week screening period (i.e., twenty-one (21) days), a baseline assessment, up to about four (4) weeks of treatment, and about a one (1) week follow-up period. The assessment schedule for the study is summarized in FIG. 12A, FIG. 12B, and FIG. 12C.

Study Period: The total planned duration of the study for each subject is up to four (4) weeks.

Screening Period: Screening may occur prior to investigational product being available onsite. During the screening, patients will be assessed for eligibility to participate in the study based on inclusion/exclusion criteria.

Figure 13:
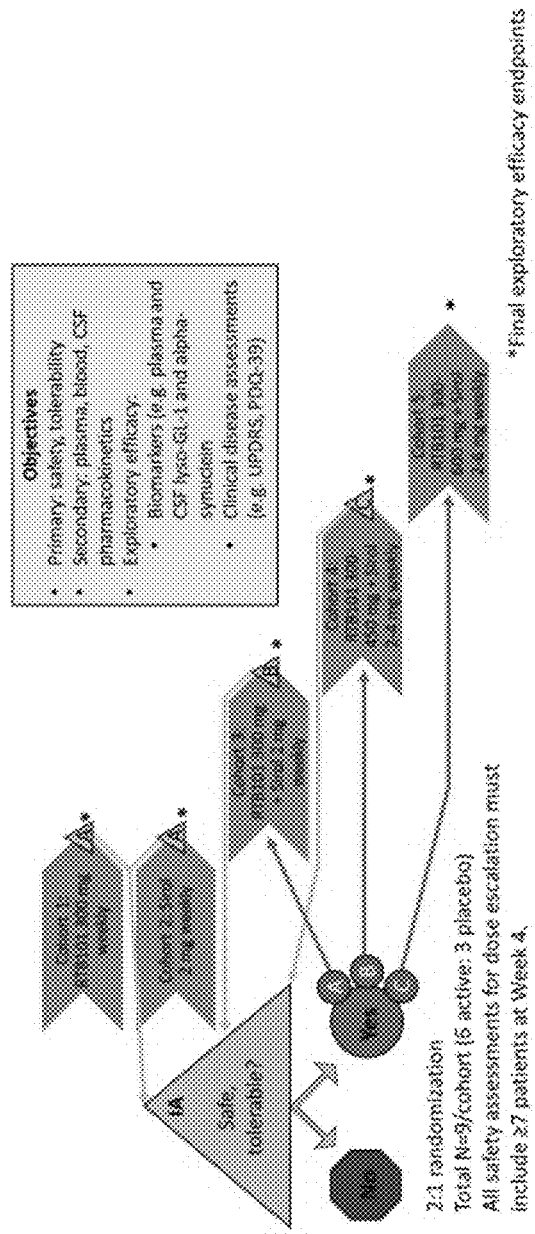
FIG. 13 shows the Example 8 clinical study design for RTB101 in combination with sirolimus for treatment of patients with Parkinson's disease.

Treatment Period: Patients will be randomized into one (1) or five (5) cohorts. Approximately sixty (60) persons will be enrolled in the study. Each cohort will comprise nine (9) patients, allowing the replacement of up to fifteen (15) persons. Cohorts 1 and 2 will be enrolled in parallel. Dose escalation cohorts will be enrolled sequentially. Prior to escalation to the next cohort, safety and PK will be assessed when six (6) patients in the active treatment arm cohort have completed twenty-eight (28) days of dosing. RTB101 drug substance will be administered as 100 mg hard gelatin capsules; sirolimus drug substance will be administered as the commercially available 2 mg tablets (e.g., available from Dr. Reddy's Lab). The study design is summarized in FIG. 13.

Cohort 1: RTB101 monotherapy—patients will be randomized 2:1 to RTB101 300 mg or placebo equivalent given orally once per week for up to 12 weeks.

Cohort 2: sirolimus monotherapy - patients will be randomized 2:1 to sirolimus 2 mg or placebo equivalent given orally once per week for up to 12 weeks.

Cohort 3: RTB101+sirolimus combination Dose 1—patients will be randomized 2:1 to RTB101 300 mg+sirolimus 2 mg or placebo equivalent given orally once per week for up to 12 weeks.

Cohort 4: RTB101+sirolimus combination Dose 2—patients will be randomized 2:1 to RTB101 300 mg+sirolimus 4 mg or placebo equivalent given orally once per week for up to 12 weeks.

Cohort 5: RTB101+sirolimus combination Dose 3—patients will be randomized 2:1 to RTB101 300 mg+sirolimus 6 mg or placebo equivalent given orally once per week for up to 12 weeks.

Rationale for Study Design: The design of this study addresses the primary objective of determining the safety and tolerability of RTB101 and sirolimus, alone or in combination, in patients with PD. The study is a randomized, double-blinded placebo-controlled, study to obtain efficacy, tolerability and safety data in an unbiased fashion.

Study Population: The study will enroll adults with PD, who are not otherwise excluded from eligibility.

Primary Endpoint: The primary endpoint of the study is to determine the safety and tolerability of orally-administered RTB101 and sirolimus, alone or in combination, as compared to placebo in patients with PD.

Secondary and Exploratory Endpoints: The secondary and exploratory endpoints are to confirm the safety and tolerability of RTB101 and sirolimus, alone or in combination, over longer periods of treatment and to obtain PK and other exploratory efficacy data.

Rationale for Dose/regimen, Route of Administration, and Duration of Treatment: The dosages and administration schedule for RTB101 and sirolimus are selected to maintain efficacious concentrations while reducing chronic exposure. A single dose level (300 mg weekly) of RTB101 is chosen based on 1) the minimum dose predicted to consistently give efficacious brain exposures, 2) a ≥2-fold safety margin below the weekly cumulative MTD of RTB101 administered with another rapalog, everolimus, and 3) weekly dosing based on targeted biology and maximizing safety. Dose escalation of sirolimus will allow assessment of safety and tolerability across the range of currently approved doses of sirolimus (2-6 mg) when sirolimus is combined with RTB101.

LIST OF COMMON ABBREVIATIONS USED IN THE EXPERIMENTAL SECTION mol=mole
M=molar
μM=micromolar
nM=nanomolar
g=gram
mg=milligram
mcg=μg=microgram
ng=ng
L=liter
mL=milliliter
μL=microliter
cm=centimeter
mm=millimeter
nm=nanometer
° C.=degrees Celsius
% (w/v)=percent weight-volume
% (w/w)=percent weight-weight
% (v/v)=percent volume-volume
OD=optical density
AAT=alpha-1 antitrypsin
BDNF=brain-derived neutropic factor
BMP4=bone morphogenetic protein 4
EGF=epidermal growth factor
FBS=fetal bovine serum
FGF2=basic fibroblast growth factor
FGF8=fibroblast growth factor 8
GDNF=glial cell-derived neutropic factor
HGF=hepatocyte growth factor
MTG=monothioglycerol
TGFα=transforming growth factor alpha
TGFβ=transforming growth factor beta
TGFβ3=transforming growth factor β3)
VEGF=vascular endothelial growth factor
Bis-Tris=bis-tris methane
dbcAMP=$N^6$,2'-O-Dibutyryladenosine 3',5'-cyclic monophosphate sodium salt
DMEM=Dulbecco's modified Eagle medium
miRNA=micro ribonucleic acid
MTT=3-(4,5-dimethylthiazol-2-yl)-2,5-diphenyltetrazolium bromide
PBS=phosphate buffered saline
SDS=sodium dodecyl sulfate
TBS=tris buffered saline
RNA=ribonucleic acid
ELISA=enzyme-linked immunosorbent assay
FACS=fluorescence activated cell sorting
qPCR=real-time polymerase chain reaction

We claim:

1. A method for the treatment of Parkinson's disease or a disease, disorder, or condition associated with alpha-1 antitrypsin deficiency in a subject in need thereof, comprising administering to the subject an effective amount of a combination of an allosteric mTOR inhibitor and a catalytic mTOR inhibitor.

2. The method according to claim 1, wherein the allosteric mTOR inhibitor is selected from everolimus, sirolimus, temsirolimus, zotarolimus, umirolimus and deforolimus, and wherein the catalytic mTOR inhibitor is selected from RTB101, CCG168, Ku-0063794, WYE-354, and 8-(6-methoxy-pyridin-3-yl)-3-methyl-1-(4-piperazin-1-yl-3-trifluoromethyl-phenyl)-1,3-dihydroimidazo[4,5-c]quinolin-2-one.

3. The method according to claim 2, wherein the allosteric mTOR inhibitor is everolimus or sirolimus and the catalytic mTOR inhibitor is RTB101.

4. The method according to claim 3 for the treatment of Parkinson's disease,
wherein:
the everolimus or sirolimus is administered at a dose of between about 0.01 and 10.0 mg/kg/week and the RTB101 is administered at a dose of between about 0.01 and 10.0 mg/kg/day;
the everolimus or sirolimus is administered at a dose of between about 0.01 and 20.0 mg/kg/week and the RTB101 is administered at a dose of between about 0.01 and 100.0 mg/kg/day;
the everolimus or sirolimus is administered at a dose of between about 0.01 and 30.0 mg/kg/week and the RTB101 is administered at a dose of between about 0.01 and 200.0 mg/kg/day;
the everolimus or sirolimus is administered at a dose of between about 0.01 and 40.0 mg/kg/week and the RTB101 is administered at a dose of between about 0.01 and 300.0 mg/kg/day; or
the everolimus or sirolimus is administered at a dose of between about 0.01 and 50.0 mg/kg/week and the RTB101 is administered at a dose of between about 0.01 and 400.0 mg/kg/day.

5. The method according to claim 4, wherein the everolimus or sirolimus is administered at a dose of between about 5 and 40.0 mg/kg/week and the RTB101 is administered at a dose of between about 25 and 400.0 mg/kg/day.

6. The method according to claim 3 for the treatment of Parkinson's disease, wherein, the everolimus or sirolimus is administered at a dose of between about 2 to about 6 mg/week and the RTB101 is administered at a dose of about 300 mg/week.

7. The method according to claim 4, wherein the Parkinson's Disease is GBA-related Parkinson's disease.

8. The method according to claim 3, wherein the allosteric mTOR inhibitor is everolimus.

9. The method according to claim 3, wherein the allosteric mTOR inhibitor is sirolimus.

10. The method according to claim 3 for the treatment of a disease, disorder, or condition associated with alpha-1 antitrypsin deficiency, wherein: the everolimus or sirolimus is administered at a dose of between about 0.01 to 1 mg/kg/day and the RTB101 is administered at a dose of between 2.5 and 20 mg/kg/day.

11. The method according to claim 10, wherein the everolimus or sirolimus is administered at a dose of about 1.5 mg/kg/week and the RTB101 is administered at a dose of about 2.5 mg/kg/day.

12. The method according to claim 10, wherein the disease, disorder, or condition associated with alpha-1 antitrypsin deficiency is a disease of the liver.

13. The method according to claim 12, wherein the liver disease is selected from cirrhosis, hepatitis, hepatomegaly, jaundice, and liver failure.

14. The method according to claim 10, wherein the allosteric mTOR inhibitor is everolimus.

15. The method according to claim 10, wherein the allosteric mTOR inhibitor is sirolimus.

16. The method according to claim 1, wherein the allosteric mTOR inhibitor and the catalytic mTOR inhibitor are administered orally.

* * * * *